(12) United States Patent
Vodnick et al.

(10) Patent No.: US 8,770,036 B2
(45) Date of Patent: Jul. 8, 2014

(54) NANOMECHANICAL TESTING SYSTEM

(71) Applicant: Hysitron, Inc., Eden Prairie, MN (US)

(72) Inventors: David James Vodnick, Prior Lake, MN (US); Arpit Dwivedi, Chanhassen, MN (US); Lucas Paul Keranen, Hutchinson, MN (US); Michael David Okerlund, Minneapolis, MN (US); Roger William Schmitz, Hutchinson, MN (US); Oden Lee Warren, New Brighton, MN (US); Christopher David Young, Excelsior, MN (US)

(73) Assignee: Hysitron, Inc., Eden Prairie, MN (US)

( * ) Notice: Subject to any disclaimer, the term of this patent is extended or adjusted under 35 U.S.C. 154(b) by 0 days.

(21) Appl. No.: 13/962,865

(22) Filed: Aug. 8, 2013

(65) Prior Publication Data

US 2013/0319127 A1 Dec. 5, 2013

Related U.S. Application Data

(63) Continuation of application No. PCT/US2012/024712, filed on Feb. 10, 2012.

(60) Provisional application No. 61/551,394, filed on Oct. 25, 2011, provisional application No. 61/441,511, filed on Feb. 10, 2011.

(51) Int. Cl.
*G01N 3/00* (2006.01)
(52) U.S. Cl.
USPC .......................................................... 73/788
(58) Field of Classification Search
USPC ........................................ 73/760, 788, 866.5
See application file for complete search history.

(56) References Cited

U.S. PATENT DOCUMENTS

| 4,074,554 A | 2/1978 | Summerlin |
| 4,693,110 A * | 9/1987 | Juengel .......................... 73/1.81 |

(Continued)

FOREIGN PATENT DOCUMENTS

| JP | 62079923 A | 4/1987 |
| JP | 05113308 A | 5/1993 |

(Continued)

OTHER PUBLICATIONS

"International Application Serial No. PCT/US2012/024712, International Preliminary Report on Patentability mailed Feb. 22, 2013", 6 pgs.

(Continued)

*Primary Examiner* — Max Noori
(74) *Attorney, Agent, or Firm* — Schwegman, Lundberg & Woessner, P.A.

(57) ABSTRACT

An automated testing system includes systems and methods to facilitate inline production testing of samples at a micro (multiple microns) or less scale with a mechanical testing instrument. In an example, the system includes a probe changing assembly for coupling and decoupling a probe of the instrument. The probe changing assembly includes a probe change unit configured to grasp one of a plurality of probes in a probe magazine and couple one of the probes with an instrument probe receptacle. An actuator is coupled with the probe change unit, and the actuator is configured to move and align the probe change unit with the probe magazine and the instrument probe receptacle. In another example, the automated testing system includes a multiple degree of freedom stage for aligning a sample testing location with the instrument. The stage includes a sample stage and a stage actuator assembly including translational and rotational actuators.

20 Claims, 40 Drawing Sheets

(56) References Cited

U.S. PATENT DOCUMENTS

| | | | |
|---|---|---|---|
| 4,750,141 A | 6/1988 | Judell et al. | |
| 4,864,227 A | 9/1989 | Sato | |
| 5,058,816 A | 10/1991 | Schreiber | |
| 5,340,261 A | 8/1994 | Oosawa et al. | |
| 5,642,298 A | 6/1997 | Mallory et al. | |
| 5,729,394 A | 3/1998 | Sevier et al. | |
| 5,773,951 A | 6/1998 | Markowski et al. | |
| 5,825,666 A | 10/1998 | Freifeld | |
| 6,731,104 B1 * | 5/2004 | Yang | 324/110 |
| 6,747,746 B2 | 6/2004 | Chizhov et al. | |
| 7,167,011 B2 * | 1/2007 | Yang | 324/754.07 |
| 7,242,173 B2 * | 7/2007 | Cavoretto | 324/72.5 |
| 7,884,326 B2 | 2/2011 | van de Water et al. | |
| 2002/0184975 A1 | 12/2002 | Ono et al. | |
| 2005/0204868 A1 | 9/2005 | Liu | |
| 2006/0043809 A1 | 3/2006 | Lau et al. | |
| 2006/0131696 A1 | 6/2006 | Arikado et al. | |
| 2006/0212248 A1 | 9/2006 | Kiesewetter et al. | |
| 2007/0068232 A1 | 3/2007 | Tolzer et al. | |
| 2007/0148792 A1 | 6/2007 | Marx et al. | |
| 2007/0227236 A1 | 10/2007 | Bonilla et al. | |
| 2008/0047749 A1 | 2/2008 | Kothan et al. | |
| 2008/0105063 A1 | 5/2008 | Laughham, Jr. et al. | |
| 2008/0255608 A1 | 10/2008 | Hinman et al. | |
| 2008/0307662 A1 | 12/2008 | Fuchs et al. | |
| 2009/0056427 A1 * | 3/2009 | Hansma et al. | 73/82 |
| 2009/0115437 A1 * | 5/2009 | Young et al. | 324/754 |
| 2010/0088788 A1 | 4/2010 | Chasiotis et al. | |

FOREIGN PATENT DOCUMENTS

| | | | |
|---|---|---|---|
| JP | 2000171472 A | 6/2000 | |
| JP | 2001208670 A | 8/2001 | |
| JP | 2005010502 A | 1/2005 | |
| JP | 2008139220 A | 6/2008 | |
| JP | 2010038543 A | 2/2010 | |
| SG | 195579 A | 12/2013 | |
| SG | 195580 A | 12/2013 | |
| WO | WO-2012109577 A2 | 8/2012 | |

OTHER PUBLICATIONS

"International Application Serial No. PCT/US2012/024712, Search Report mailed Sep. 24, 2012", 5 pgs.

"International Application Serial No. PCT/US2012/024712, Written Opinion mailed Sep. 24, 2012", 16 pgs.

"International Application Serial No. PCT/US2012/24712, Invitation to Pay Additional Fees mailed Jun. 7, 2012", 2 pgs.

Bhushan, Bharat, et al., "Nanomechanical characterisation of solid surfaces and thin films", Retrieved from the Internet: <http://www.micronano.ethz.ch/education/Lecture_4_Paper_IMR_Nanoiden_Li_03.PDF>, (Dec. 2003), 40 pgs.

Niehe, Stefan, "A New Force Measuring Facility for the Range of 10mN to 10N", Retrieved from the Internet: <http://www.imeko.org/publications/wc-2003/PWC-2003-TC3-019.pdf>, (Jun. 2003), 6 pgs.

Vanlandingham, Mark R, et al., "Nanoidentation of Polymers: Overview", Retrieved from the Internet: <http://fire.nist.gov/bfrlpubs/build00/PDF/b00063.pdf>, (Dec. 2000), 3 pgs.

Japanese Application Serial No. 2013-213290, Office Action mailed Feb. 4, 2014, with English translation of claims, 11 pgs.

Japanese Application Serial No. 2013-213291, Office Action mailed Feb. 4, 2014, with English translation of claims, 9 pgs.

Japanese Application Serial No. 2013-553607, Office Action mailed Feb. 4, 2014, with English translation of claims, 7 pgs.

Korean Application Serial No. 10-2013-7024188, Office Action mailed Feb. 28, 2014, with English translation of claims, 6 pgs.

* cited by examiner

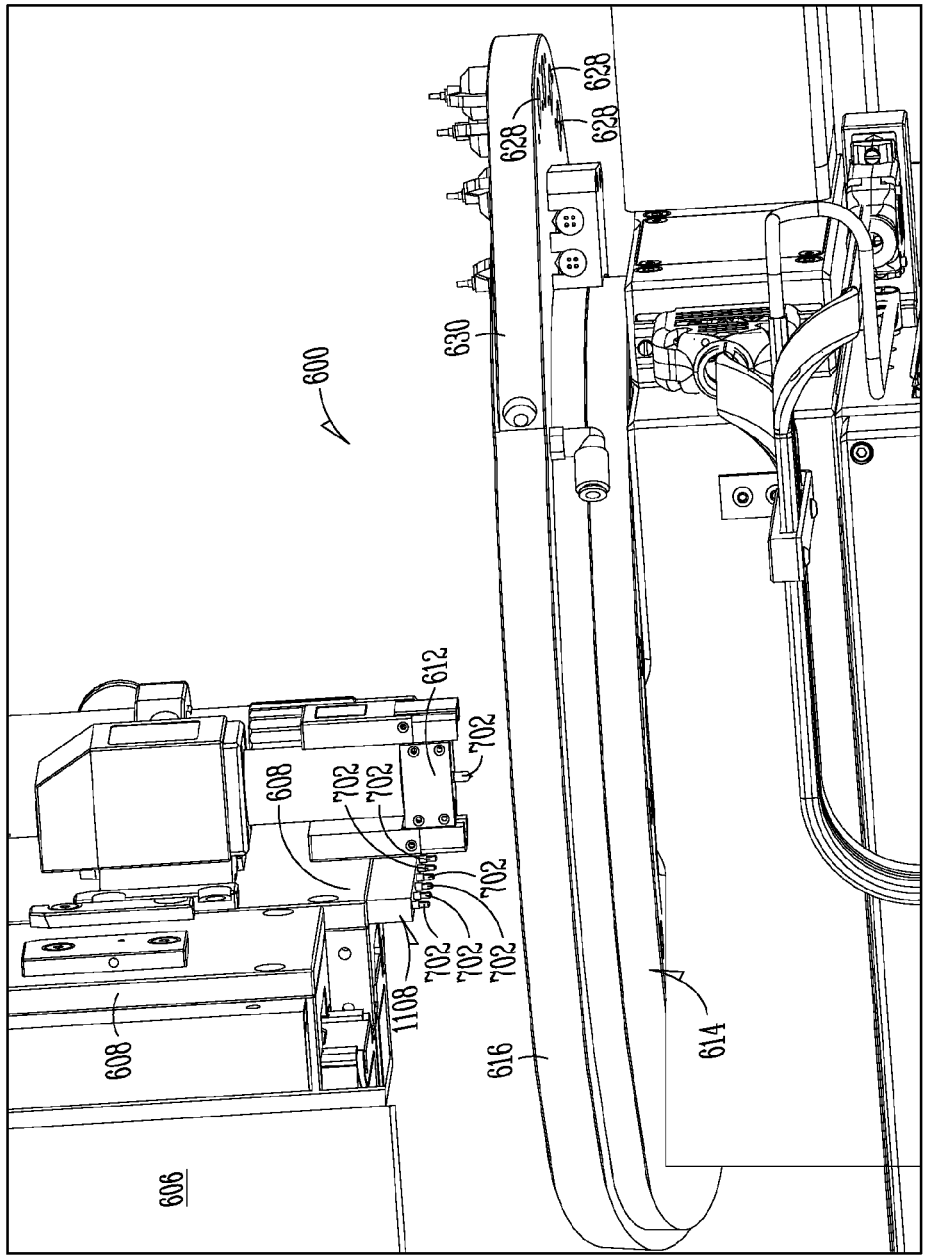

NANOMECHANICAL TESTING SYSTEM

RELATED APPLICATIONS

This application is a continuation under 35 U.S.C. 111(a) from International Patent Application Serial No. PCT/US2012/024712, filed Feb. 10, 2012, and published on Aug. 16, 2012 as WO 2012/109577, which claims priority benefit of U.S. Provisional Application Ser. No. 61/441,511, filed Feb. 10, 2011, and U.S. Provisional Application Ser. No. 61/551,394, filed Oct. 25, 2011, all of which are incorporated herein by reference in their entirety.

STATEMENT REGARDING FEDERALLY SPONSORED RESEARCH OR DEVELOPMENT

This invention was made with government support under award number DE-SC0002722 awarded by the US Department of Energy. The government has certain rights in this invention.

TECHNICAL FIELD

Nano and micron scale material testing.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright Hysitron, Inc. All Rights Reserved.

BACKGROUND

Nanomechanical test instruments are used in R&D facilities around the world for quantitative mechanical and tribological measurements. Nanoindentation is a method to quantitatively measure a sample's mechanical properties, such as elastic modulus and hardness, for example, using a small force and a high resolution displacement sensor. Typically, a force employed in nanoindentation is less than 10 mN, with a typical displacement range being smaller than 10 µm, and with a noise level typically being better than 1 nm rms. The force and displacement data are used to determine a sample's mechanical properties, and to determine if the properties are within acceptable performance limits for a particular product or application.

In some examples a probe with a well-known shape is pressed into a material in a predetermined manner and removed therefrom while continuously measuring the probe position and applied probe/sample contact force. Nanomechanical characterization employs one or more actuators and sensors to perform one or more of control or measurement of the applied force that the probe exerts on the material and the relative displacement of the probe during the test. Sensors and actuators are applied along a single axis, in one example, as is the case with standard instrumented depth sensing indentation, or in two to three dimensional space for tribological measurements. Probe-based nanomechanical testing techniques are used for the determination of mechanical properties such as hardness, modulus, fracture toughness and tribological characteristics such as scratch/mar resistance, friction coefficient measurement and interfacial adhesion assessment.

Critical technological advances in nanomechanical test instruments have been mandated by the ability to control processes and structures to nanometer length scales and have required the development of higher sensitivity force and displacement actuators/sensors. Due to combined advances in actuator/sensor and control electronics technologies, nanomechanical testing systems can control and measure forces to within several nano-Newtons (nN) and control and measure displacements within several Angstroms (Å). These developments have permitted quantitative nanomechanical characterization of ultra-small volumes of material, including thin films used in the semiconductor and data storage industries; nano-composite polymers, ceramics, metals; and nanostructures including nanoparticles, nanowires, nanopillars, and nanotubes.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 11B is a perspective view of the tip changing assembly including a tip magazine and the stage receptacle flange.

DESCRIPTION OF THE EMBODIMENTS

Figure 1:
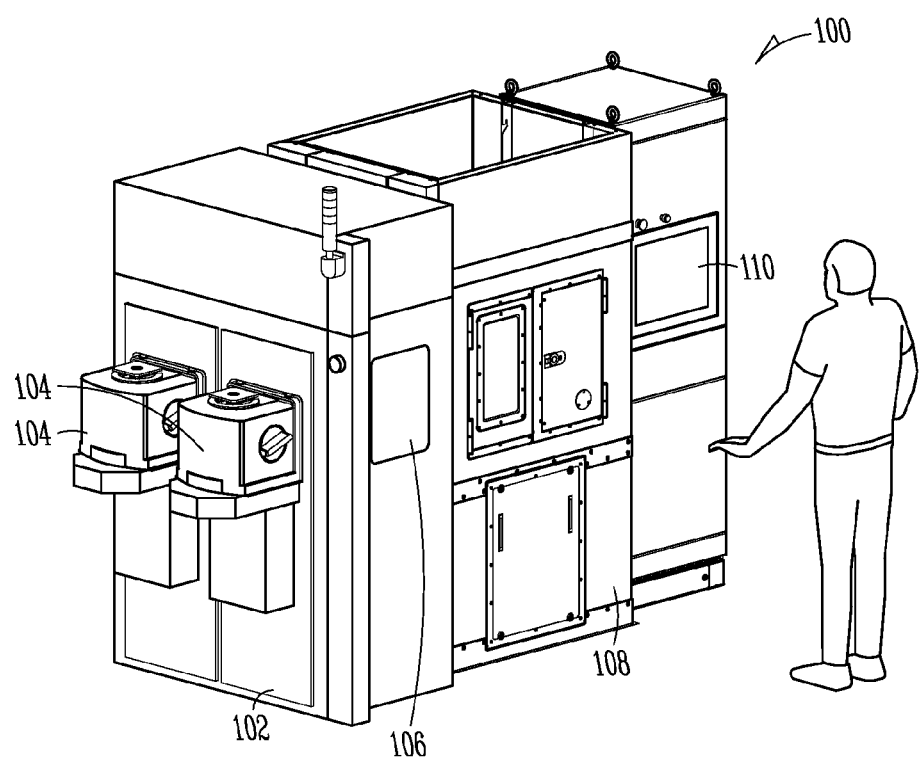
FIG. 1 is a perspective view of one example of an automated testing assembly.

In the following detailed description, reference is made to the accompanying drawings which form a part hereof, and in which is shown by way of illustration how specific embodiments of the present disclosure may be practiced. In this regard, directional terminology, such as "top," "bottom," "front," "back," "leading," "trailing," etc., is used with reference to the orientation of the Figure(s) being described. Because components of embodiments of the present apparatus can be positioned in a number of different orientations, the directional terminology is used for purposes of illustration and is in no way limiting. These embodiments are described in sufficient detail to enable those skilled in the art to practice aspects of this disclosure, and it is to be understood that other embodiments may be utilized and that structural changes may be made without departing from the scope of the present disclosure. Therefore, the following detailed description is not to be taken in a limiting sense, and the scope of the present disclosure is defined by the appended claims and their equivalents.

OVERVIEW

The systems described herein provide a series of capabilities beyond those of previous devices. Reference is made in this overview to an automated testing assembly 100 as described herein including its components. Multiple measurements of multiple samples are performed without time and labor intensive reloading and corresponding repositioning of a sample for a single measurement. High throughput of samples with rapid measurements of one or more samples are achieved with the systems described below. Sample handling, positioning, testing and observation of one or more samples 202 (e.g., 10, 100, 1000 or more samples) are performed by the system while the system is adaptively able to: prepare the one or more samples, execute testing routines, configure and calibrate the instruments, selectively operate the instruments as needed (to test, verify data, calibrate the instruments and the like), configure the instruments, identify testing locations, execute measurements and analyze data. Because the system 100 is configured to conduct testing and measurement of a large number of samples, technician error, for instance, from individual handling (of instruments and samples), positioning and testing of discrete samples is substantially avoided.

In contrast, other systems require labor and time intensive effort by technicians having substantial technical aptitude to properly prepare individual discrete samples, calibrate the system, set up the appropriate testing routines and execute measurements.

Furthermore, the systems described herein ensure rapid, accurate and consistent testing of a plurality of samples within environmental conditions that cause distortion and inaccuracy of measurements taken on the sub-micron scale (i.e., micron scale; one or more microns and below, such as the nano scale). The systems isolate the automated testing system 600 and correspondingly minimize the effects of disturbances including, but not limited to, acoustical, air flow, temperature variability, vibratory disturbances and the like. Testing and measurement with the systems are performed with inherent and uncontrollable disturbances present in these exterior environments (e.g., manufacturing), making in-line and near-line nanomechanical testing possible. Stated another way, the systems 100 described herein are configured for use within production environments and thereby capable of rapidly and accurately testing and measuring mechanical properties at micron, sub-micron and nano scales. Remote and discrete testing of a sample relative to the production environment is thereby avoided.

Moreover, the systems described herein facilitate the testing and measurement of large quantities of samples in the production environment while at the same time minimizing material contamination, material breakage and system downtime.

The apparatus provides systems and methods for testing a series of material samples 202, 310 (e.g., plurality of 10, 100, 1000 or more) utilizing a micro- and nanomechanical testing instrument 612. The apparatus and method includes:

delivering a plurality of material samples 202 to a micro and/or nanomechanical testing instrument 612 of an automated testing system;

positioning at least one of the plurality of material samples 202 in a substantially pre-determined position relative to at least one probe having a substantially known tip geometry. In one example, the system 100 is configured to not, per-se, place samples in a pre-determined location, but rather place the sample 202 on a sample stage 614, and then through an automated process, bring the stage 614 carrying the sample 202 to the probe 702 of the mechanical testing instrument 612 for testing;

applying a force with a probe 702 in one or more of a normal direction (e.g., the Z axis/direction, which may be substantially perpendicular to the sample surface) and/or lateral direction(s) (e.g., substantially in-plane with the sample surface, otherwise generally known as the x- and y-axis/directions) relative to the surface of the positioned sample 202;

collecting data relative to the interaction or interactions between the probe 702 and a positioned sample (such as force-displacement data);

disengagement of the probe 702 from the sample 202, followed by the apparatus (e.g., by a robotic handling system 200) unloading the tested material sample 702 before loading and testing the next sample.

Materials Capable of Being Tested by One or More Examples of These Systems and Methods In the course of the following description reference is made to a variety of materials that will undergo nanomechanical testing as "materials" or "samples." As detailed herein, the terms "material(s)" or "sample(s)" broadly cover a wide variety of substances capable of being tested nanomechanically. These materials are virtually any composition, and include, but are not limited to, such substances as: ceramics, metals, polymers, wood, biological materials (such as red blood cells, cartilage, bone), liquids, viscous materials, MEMS devices and the like. While the materials tested are virtually unlimited, one of ordinary skill in the art will recognize that the critical and necessary aspects of an automated nanomechanical testing system will be relatively uniform, regardless of the actual materials tested. For illustrative purposes only, the following system 100 and methods will describe an example of such a system wherein the materials tested are semiconducting materials deposited on wafers. The disclosure herein is intended to broadly cover the testing of other samples and sample materials beyond semiconductor wafers and materials. Throughout this specification, reference may be made to one semiconductor wafer (or one other material) as the "sample" indicating it is one sample in a larger set of samples that collectively are referred to as a "material" or "materials". For example, broadly speaking, the nanomechanical testing instruments 612 conduct tests on materials (e.g., semiconductors), but individual "samples" of those materials are loaded into the instrument and tested.

Storage Modules Suitable for Storing Material to Tested

Materials are delivered to and removed from the nanomechanical testing instrument (e.g., the automated testing system 600). One or more of a plurality of devices are configured to deliver and/or remove the materials. One example, described further below, stores materials prior to testing in an appropriate container or storage module 104. The type of storage module is dependent on the nature of the materials tested. Other examples of material handling devices, prior to testing, serially deliver material samples to the nanoindentation apparatus using automated means, such as a conveyer belt-type apparatus, robotic assemblies and the like. Other options are considered as well.

Storage Module

One option for a storage module is the material storage module ("SM"), wherein a number of similar materials are arranged and stored prior to nanomechanical testing of said materials. The specific type of storage module will depend upon a number of factors, such as the size of the sample and the number of samples tested in a testing sequence.

Small Samples: Where the samples to be tested are relatively small, as is the case with, for example, certain MEMS devices (i.e., Microelectromechanical Systems) or numerous liquid samples, the material storage module is optionally relatively small, and is accommodated entirely within the testing enclosure without needing opening of the testing chamber to serially place and remove test samples. Examples of such storage modules include a microplate having a series of sample wells (such as 6, 12, 24, 96, 384 or 1536 sample wells arranged in a 2:3 rectangular matrix), such as the sample module 308 shown in FIG. 3B. Another such example of a storage module includes a pallet an array of, for example, MEMS devices or other small samples positioned or fixed on the pallet.

Larger Samples: Where multiple samples are not readily accommodated within the confines of a testing enclosure 108 the nanomechanical testing system 100 employs, in one example, a storage module 104 for containing test samples outside of the enclosure. In some embodiments, said external material storage module 104 acts as a magazine and contains multiple smaller material storage modules (such as, for example, palletized MEMS devices, the aforementioned microplate, and the like) for individual loading into the enclosure for testing. In another embodiment, in the semiconductor industry, the storage module is a FOUP, or Front Open Unified Pod, which stores and transports 13, 25 or another number of individual wafers, such as a plurality of samples 302 (See FIG. 3A). As one of ordinary skill in the art will readily appreciate, a FOUP is an example of a storage module. Many other non-FOUP storage modules exist, but are referred to by other names or acronyms depending on the relevant industry and the specific material housed.

Delivery Mechanism

In another embodiment, samples tested are not transported and stored in a Material Storage System prior to testing, but are instead serially delivered via a mechanical apparatus, such as a conveyer belt, to or near the testing site. While those of ordinary skill in the art will recognize that such delivery apparatuses can take many forms (the conveyer belt being one such form) we will refer to delivery apparatuses collectively as "delivery mechanisms."

In one embodiment of the delivery mechanism, the physical location of the individual materials with respect to the delivery mechanism or storage module is known or predetermined. The handling system (addressed below) is able to ascertain the position of the transported material to be tested in order to engage the samples prior to positioning the samples for nanomechanical testing. The storage module, such as the storage module 104, will house the materials in a uniform and predetermined arrangement (such as in a FOUP). Alternatively, the handling system will be capable of interacting with the materials in the storage module or on the delivery mechanism in such a way that the handling system can reliably locate and engage each individual sample prior to testing.

In one example, there is uniform spacing between the individual samples, for instance a plurality of samples 302 or 310 are arrange in a uniform manner. In certain embodiments, sensing devices are employed to reliably identify the location of a material prior to the handling system interaction with the same where the spacing of each material is not substantially uniform. Such sensing devices include, but are not limited to, pattern and shape recognition sensors, acoustical sensors, thermographic sensors, tactile sensors, RF sensors, electrical contacts and the like.

Regardless of the actual means employed, the materials are stored and/or delivered to or proximate to the nanomechanical testing instrument (such as the instrument 612 of the automated testing system 600) in such a manner that in one example, a handling system (such as the robotic handling system 200 shown in FIG. 2) is able to releasably and selectively engage said samples 202 (e.g., picking them up, repositioning them, moving them, etc.) to deliver them to the nanomechanical testing instrument. In another example, the materials are automatically delivered to a nanomechanical testing system 600 without the intervening handling system. Aspects of the handling system are addressed in more detail below.

Handling System

Figure 6A:
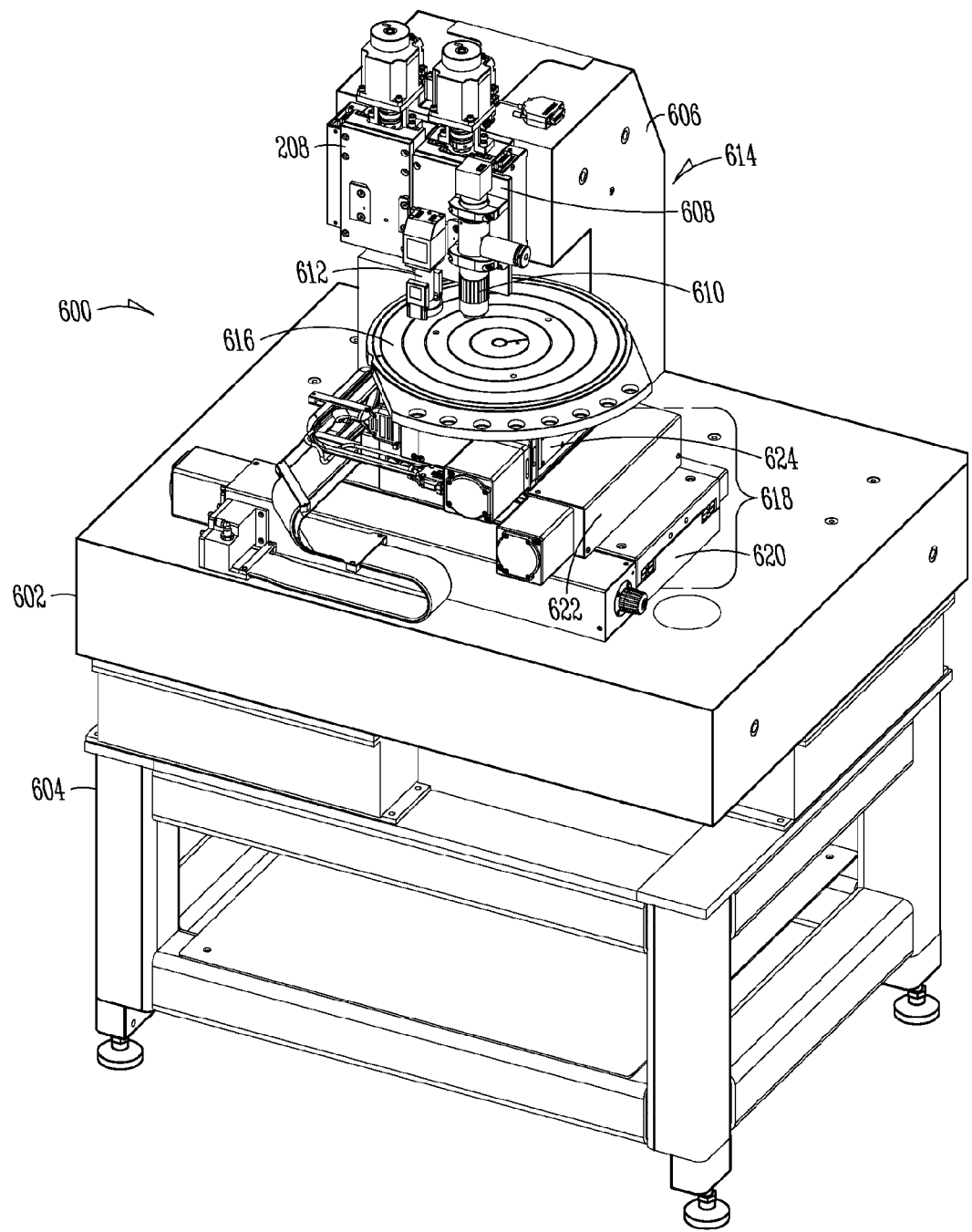
FIG. 6A is a perspective view of one example of an automated testing system.

The handling system, which can take numerous forms, is responsible for serially engaging multiple samples 202 (materials) and moving said material either from the storage module 104 or the delivery mechanism (e.g., a chute, bin, belt conveyor or the like). In one embodiment, the handling system, such as the robotic handling system 200 shown in FIG. 2, engages a material and mechanically positions that material on a support structure, such as a mechanical testing stage 614 as shown in FIGS. 6A, B (e.g., a wafer chuck) that is located inside a nanomechanical testing instrument. Handling systems take many forms, each appropriate to the material being tested. For the purposes of explaining the apparatus, one example of a handling system (in this instance, an EFEM) is used in one embodiment.

An EFEM is employed to transport material (in this case silicon wafers or quartz photo-masks) between storage carriers (e.g., modules 104, such as FOUPs) and the nanomechanical testing instrument 612 of the system 600 (described below). In an embodiment, an EFEM is configured to unload material, such as a 300 mm wafer sample 202, and deliver that wafer to a nanomechanical testing instrument (e.g., instrument 612 of the automated testing system 600) for testing, imaging, or other analysis, and then return the material to its carrier, such as the storage module 104, upon completion of said process or test. While an EFEM is an example of a system and apparatus for handling materials, we will refer to any system for handling materials as a handling system. Examples of non-EFEM handling systems in other industries include dedicated robotics systems that act as an intermediate mechanism to "bridge the gap" between two or more systems/processes. Such handling systems with various configurations are employed in numerous industries, including (by way of example and not of limitation): the pharmaceutical and biotech, semiconductor, nano-technology, photovoltaics (PV) solar cell, fuel cell, data storage, opto-electronics, and liquid crystal display/light emitting diode industries.

Opener

Where material samples are contained in a material storage module 104, the handling system is configured, in one example, with an opener to render accessible the samples or materials stored in the module. In the semiconductor industry, wafers stored in a FOUP (a FOUP is one example of a material storage module) are delivered to a FOUP opener (one kind of opener) that is attached to the Equipment Front End Module (EFEM) (the sample handling module 106 in FIG. 1) employing robotic means for manipulating wafers as well as, in some instances, a wafer realignment device (see below).

Figure 4A:
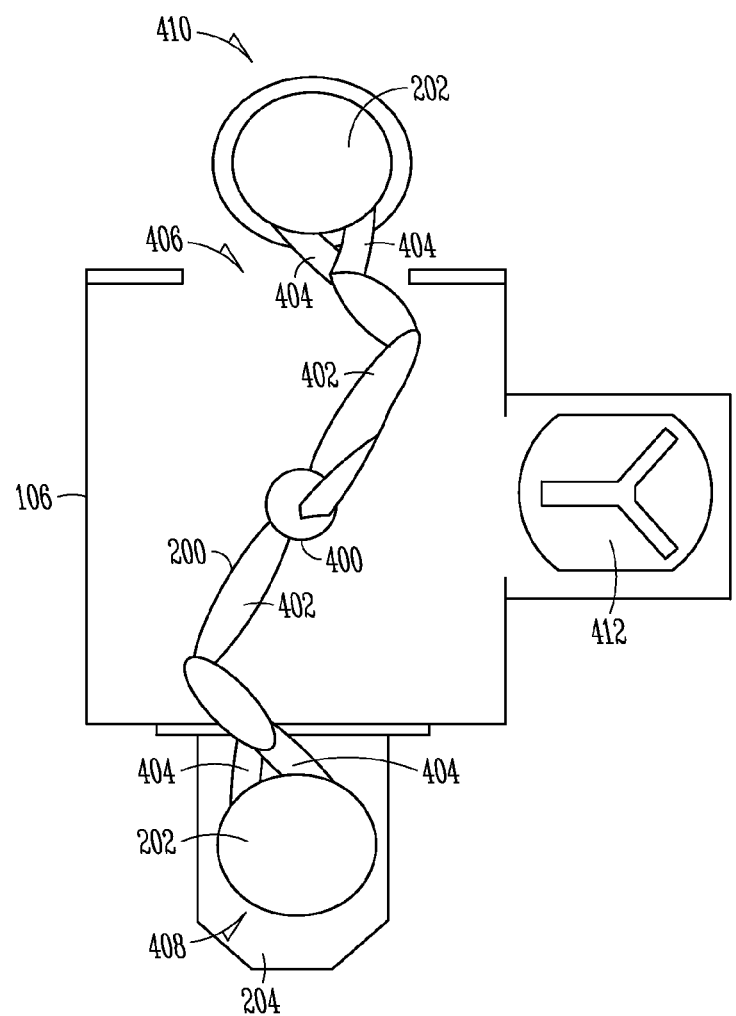
FIG. 4A is a plan view of one example of a robotic handling system in a plurality of orientations with a sample within the sample handling module of FIG. 2.

In an exemplary system, the EFEM is configured to insert and withdraw 200 and 300 mm wafers from the nanomechanical test instrument. More specifically, the front of the EFEM will contain one or more Front Opening Unified Pod (FOUP) openers for 13 and 25 wafer FOUPs (cassettes). For instance, the sample handling module in FIG. 1 includes one or more storage module loading racks 204 configured to receive and facilitate the opening of the storage modules 104 (See FIG. 2). In another embodiment, a robotic arm provides the transfer functionality between the cassette, a pre-aligner, and the nanomechanical test instrument. For instance a robotic handling system 200, shown in FIG. 2, includes in one example an articulating arm 402 and one or more handling forks 404 as shown in FIG. 4A. Means of sample transfer other than a robotic arm may also be used without departing from the scope of this disclosure (e.g., mechanical linkage assemblies, vacuum assemblies, electrostatic actuators, magnetic actuators, high pressure gas jets and the like).

Pre-Aligner

In one system, the handling system (e.g., the EFEM) incorporates a pre-aligner 412 (FIGS. 4A, B) which includes approximately ±0.05° accuracy to position the sample 202, such as the wafer (or any other material), in the desired orientation prior to placement within the nanomechanical test instrument (e.g., on a sample stage 614 as shown in FIG. 6A). In other embodiments, sample alignment and re-alignment is handled inside the nanomechanical test instrument by, for example, a stage or wafer chuck 614 capable of one or more of rotational and translational movement.

Ionizer

In an embodiment, the EFEM units also contains an ionizer and +1 Pa environment module (FFU).

Nanomechanical Testing Instrument (NTI)

The system 100 and methods for using the same include a nanomechanical testing instrument. One nanomechanical testing instrument includes, but is not limited to, the Hysitron TI950 TriboIndenter. Nanomechanical testing instruments, such as the TI950 are configured with computer, software and controller means for conducting automated nanomechanical testing. In other embodiments, and as explained further below, the NTI is an automated, high throughput instrument (e.g., the automated testing system 600) capable of supporting numerous nanomechanical characterization techniques and is coupled to a control module, such as the control station 110 shown in FIG. 1, and enables precise, feedback-controlled nanomechanical testing of a large number of samples. A plurality of various NTIs may be utilized with the automated testing assembly 100, depending upon the nature of the samples to be tested. One such example is outlined below.

Automated Mechanical Test Apparatus for Micron and Nano-Scale Testing

The automated testing system 600 includes a mechanical testing instrument 612 having the testing probe 702 (See FIGS. 6A, B and 7A-C). The automated testing system 600 is configured for one or more of indentation, scratching and other testing operations including, but not limited to, tension, compression, fracture, tribological testing and the like.

The actuator/sensor, such as the transducer assembly 700, is configured to provide force and displacement in one or more of the normal, lateral and arcuate directions with one or more testing heads (e.g., probes or tips 702) configured for any combination of normal, lateral and arcuate movement directions.

Translation staging, including one or more of the sample stage 614 including the stage actuator assembly 618, or an instrument stage 608 are configured, in one example, for any combination of XYZ translation for material and/or testing head translation. In another example, the sample stage 614 is configured for material positioning of the sample 202 relative to the testing head, such as the probe 702, for instance with X-axis, Y-axis and rotational positioning (e.g., theta positioning).

The automated testing system 600 is configured for receiving samples from the automated material handling system, such as the sample handling module 106, shown in FIG. 1. The automated testing system 600 further includes a fixture mechanism for affixing or anchoring samples 202 to the staging. In one example, vacuum ports 632 affix the samples 202 to the staging.

The automated testing system 100 includes, in one example, a support frame that mechanically couples various hardware components of the test apparatus. For instance, the support frame includes the automated testing enclosure 108. In another example, the support frame includes a granite base 602 and a system support table 604, as shown in FIG. 6A. In some examples, the support frame mechanically couples the test apparatus (automated testing system 600) to the automated material handling systems, such as the sample handling module 106, shown in FIG. 1.

In another example, the automated testing system 600 includes an optics column, such as an observation column using one or more of optical, infrared, and other observation techniques for observation of the samples. The optics column includes an optical instrument, such as the optical instrument 610 shown in FIG. 6A. The optical instrument 610 is configured to view test placement location. In another example, the optical instrument 610 provides machine vision for automated recognition of testing sites, rotational and translation deskewing of the sample and the like.

In still other examples, the automated testing assembly 100 includes an anti-vibration system.

The automated testing assembly 100 further includes a control station 110, shown in FIG. 1, including control software, memory, hardwired controls, a user interface and the like configured for one or more of the selection of testing sites, acquisition of force—displacement data, data analysis, automated system calibration routines and automated tip shape validation routines.

The control system, such as the control station 110, coordinates the communication between the components of the automated testing assembly 100 as well as peripheral machines and systems having a relationship with the assembly 100, such as production devices upstream or downstream from the assembly.

The above outline is an example of one such system including options for use with the system. Numerous other configurations are possible without departing from the systems described herein. Some configurations include all of the above described features, a portion of the described features, and in some examples include other features in addition to those listed.

The following is a sequence of steps for implementing an embodiment of system, wherein the interaction between the material handling system (e.g., the sample handling module 106) and the NTI (e.g., the automated testing enclosure 108 including the automated testing system 600) is outlined and wafers comprise the materials tested. The system is configured with a staging system and a wafer chuck (e.g., a stage 614) for securing the wafers prior to testing. The example steps for implementation include one or more of the following:

i) A sample 202 is engaged by the handling system (e.g., the robotic handling system 200);
ii) The elevation pins 634 (see FIGS. 10A, B) are raised if not already raised;
iii) A door to the enclosure is opened (if not already open) permitting access to the interior of the NTI (the automated testing enclosure 108);
iv) The handling system 200 transports the wafer 202, through the door and into the interior chamber of the NTI;
v) The wafer 202 is placed onto the raised pins 634 and released;
vi) The handling system 200 withdraws from the chamber and the door to the enclosure is closed;
vii) Vacuum (e.g., at the vacuum ports 632) is provided and the pins 634 are lowered, with the vacuum securing the wafer 202;
viii) The nanomechanical testing and/or imaging sequences and/or data acquisition are performed with the automated testing system 600;
ix) The vacuum is released at the vacuum ports 632;
x) The pins 634 are raised;
xi) The door to the enclosure 108 is opened;
xii) The material handling system 200 retrieves the sample from the NTI, and places it in a predetermined location, for instance in the sample storage module 104;
xiii) Return to step 1) where a sample is engaged by the handling system and the steps are repeated or performed in another permutation.

As will be readily recognized, a number of these steps are conducted simultaneously or out of the specific sequence represented above, in one example, without departing from the exemplary apparatuses and methods described herein. For example, steps i, ii, and iii are performed in a different order or performed simultaneously, in one option. Additionally, several of these steps include sub-steps. For example, step viii wherein the system conducts nanomechanical testing and/or imaging and/or data acquisition includes many (in one example, nearly infinite permutations) depending upon the specific configuration of the instrument in various examples.

As is detailed further below, the system optionally incorporates a staging system and damping technology. The system also incorporates one or more of the following capabilities.

Staging System

Regardless of the specific nature of the NTI, the system is configured with a support structure, such as a sample stage 614 or a wafer chuck, upon which a sample is placed or secured prior to and during testing, such as nanoindentation testing, scratch or wear testing, etc. A wide variety of stages are employed by the system, some of which are specific to the nature of the materials to be tested.

In an embodiment, once a material/sample is engaged by the handling system (e.g., the robotic handling system 200), the material is automatically placed on a support structure ("SS") such as a sample stage or a wafer chuck, prior to nanomechanical testing (nanomechanical testing system, as used herein includes systems configured to also test on the micro-scale as well). In one example, the support structure, such as the sample stage 614, is located inside the NTI housing and is used to temporarily secure the material during nanomechanical testing.

By way of example, where the apparatus is utilized in the semiconductor industry, the nanomechanical test instrument incorporates an X-Y staging system, an X-Y-theta staging system or the like with a travel long enough to accept the wafer from the EFEM. Where the wafer is to undergo, for example, nanoindentation testing utilizing a fixed probe that is not capable of substantial movement in the X-Y dimensions, the sample stage upon which the wafer rests is configured to travel, and thus move the wafer relative to the indentation probe so that the probe is able to test all regions of a 300 mm wafer without human intervention. Embodiments include a high velocity X-Y stage or X-Y-Theta stage with a small encoder resolution.

Vibration Mitigation

Because nanomechanical testing is conducted at incredibly small scales, acoustic noise, mechanical vibration, electrical and magnetic interference, and air currents affect test results by introducing unwanted disturbances that are larger than the quantities being measured. Such disturbances are often referred to collectively as "noise." The sources of such noise are varied. Regardless of the source, any noise may have an appreciable effect on test data and should be minimized. The apparatuses and methods described herein minimize noise even in production and manufacturing environments to facilitate large-scale testing of a plurality of samples.

Instrument Housing

In one embodiment, the NTI (e.g., the automated testing system 600) is surrounded by a physically passive barrier to external disturbances, such as an instrument housing or automated testing enclosure 108. In a variation of the embodiment, the housing structure surrounds the instrument (e.g., the mechanical testing instrument 612), the staging systems, and the test sample during active testing, but it excludes the material handling system, the sample delivery mechanism and any openers or sample pre-alignment equipment. In another example, the storage modules, handling system, delivery mechanism, and other equipment are enclosed within the instrument housing and still achieve substantial damping. Because these devices tend to themselves emit noise at some level, even when not active, such equipment is located outside of the physical instrument housing in another example.

The housing itself can be comprised of various materials, including, without limitation, fiberglass enclosures and enclosures with an acoustic damping layer, thermally insulating materials. In another example, the physical shape of the enclosure itself has noise mitigating, aerodynamic properties. In an example a damping housing includes a housing constructed of a fiberglass which incorporates a damping core. The instrument is located inside. In another embodiment, the housing is constructed of a metal, such as stainless steel and is further combined with acoustic damping materials, for instance as shown in FIG. 1 with the automated testing enclosure 108.

Anti-Vibrational

In an embodiment, the system incorporates additional anti-vibration strategies: including active and passive strategies. Such passive damping includes "floating" mechanisms, such as springs, maintained air pressure, shock absorbing devices, or a material with high damping properties, such as rubber, other elastomers or suspension mechanisms. All of these are passive anti-vibration techniques used alone or in conjunction with other mechanisms. Another damping strategy affixes instruments housed inside the enclosure to a block of material, such as a large piece of stone, for instance granite. In one embodiment, the material takes the form of a heavy granite arch-like structure or cantilevered instrument column 606 and base 602 (see FIG. 6A) which, by virtue of its mass, damps vibrations that might otherwise be transferred to the instruments 612 (e.g., nanoindenters, AFM (atomic force microscope), SPM (scanning probe microscope), optical microscopes, etc.) coupled thereto.

Because vibration and noise mitigation is important for nanomechanical testing in an automated environment, the system also contains one of more active antivibrational mechanisms, in another example. One active method is achieved through the incorporation of piezo active elements that sense vibration and actively cancel out vibration by creating an opposite out of phase damping force (e.g., vibration with a counter frequency). In an example, such piezo active elements are located beneath the NTI (e.g., beneath a system support table 604 or a granite base 602, as shown in FIG. 6A) in order to partially isolate the sensitive instruments, the sample stage and the sample from vibrations transferred through the floor in a factory environment. In another example, piezo active elements are employed inside the instrument housing, for example, under the granite structure mentioned above. In yet another example, voice coil based damping systems are incorporated into the automated testing system 100.

Wafer Chuck

In one configuration relevant to wafer testing, a modified 200 mm and 300 mm wafer chuck (e.g., a sample stage 614) comprised of a solid piece of stainless steel is incorporated. The chuck in one variation, also contains an extension containing a quartz sample (e.g., a diagnostic sample 1106), which has known physical properties and is utilized for tip area function calibrations, wherein a nanoindentation tip conducts one or more indents into the quartz and, for example, force and displacement data is analyzed. In another embodiment, a sample of aluminum or other suitable material is similarly utilized to calibrate a tip-optics offset.

In one example, wafer chucks are rotational, which may create instrument reliability problems. Optionally, such rotational capabilities are not included in the wafer chuck described herein. In another example, the sample stage includes translational and rotational stages. Moreover, the chuck in an embodiment does not incorporate a wand slot.

In another embodiment, the automated instrument incorporates a computer controlled on/off switch to control the suction from the vacuum pump as well as automatic 'lifting pins' (typically three or more) which are employed to raise and lower the wafer to and from the vacuum chuck.

Z-Axis

The NTI accommodates movement of the indentation probe, for example, relative to the sample in the z-axis. In an example system, the z-axis of the instrument accommodates up to two separate testing heads. This is desired for several reasons, including: A) applications where both scratch and indentation are important—two tips are required, B) in only a scratch or indentation application (i.e., dual identical heads are used), if one tip becomes defective testing can still continue, and C) possibility of running two transducers simultaneously for a more than twofold increase in data acquisition. It is noted that in some configurations, the control computer (e.g., the control station 110) may be required to switch between two controllers (e.g., Hysitron Performech controllers). In one example one or both of the controllers include digital signal processors (DSPs) that cooperate with and act upon commands from the control station 110. The controllers communicate with one or more mechanical testing instruments (e.g. 610 including one or more of mechanical and tribological transducers).

Material Specific Components

It is recognized that certain embodiment of the system are configured to create a positive (or negative) pressure microenvironment. Additionally, in one example, the instrument incorporates an ionizer and/or filtration system, an ESD-proof enclosure, opening/closing load door (mentioned above).

Auto Tip Change Mechanism

In one embodiment, the NTI incorporates a mechanism, such as a probe change assembly 1100 that automatically changes tips when A) going between indentation and scratch testing (when the z-axis can only accommodate a single testing head), and B) when testing results fall outside pre-defined acceptable levels and an 'auto tip validation' software routine identifies the tip as defective.

One mechanism utilizes a planetary set of gears that hold a multitude of tips. When it is determined that a tip is no longer functioning within acceptable parameters, the system decouples the tip, which in some embodiments is affixed to a threaded post affixed to a transducer, and will select a replacement tip or a tip of a different desired geometry, and affix that tip to the threaded post. Because of the sensitivity of the transducer, and the danger of applying excess torque when affixing a replacement tip, an embodiment provides for a known number of rotations to securely install and remove a tip and the tip change mechanism is configured to limit the permitted amount of torque. Optionally, the replacement tip is held by a mechanical interfitting that affixes the tip to the instrument without rotation, such as by snap fit, interference fit, friction fit and the like.

Speed Enhancement—Finding the Sample Surface Quickly

In most nanoindentation systems, testing is conducted slowly because a large percentage of the testing time involves approaching the sample slowly with a probe. Because testing is performed on a micro- and nano-scale level, and given the sensitivity of the transducer to which the probe is affixed, it is critically important that the tip not "crash" into the sample to be tested. Crashing the tip into the sample can destroy the transducer and or the tip (e.g., the transducer assembly 700 or the probe 702), rendering the instrument inoperable.

In an embodiment of the system described herein, the macro approach of the tip to the sample is not facilitated by a human operator. To reduce cycle time one embodiment incorporates a sensor that extends some distance below the probe, so in a "quick approach" mode the sensor contacts the sample before the indentation tip can crash into the sample. Contact of the sensor with the sample triggers the system to withdraw the sensor and proceed slowly for the last remaining distance to bring the tip (e.g., the probe 702) into contact with the sample without damaging it or the transducer (e.g., the transducer assembly 700 including the capacitor assembly 710.

In another example, the system described herein is equipped with one or more sensors such as laser triangulation sensors, capacitance sensors, fiber optics-based interferometers that enable the tip to quickly close the majority of the gap. In one embodiment, the tip is quickly directed to within 1 micron of the sample surface, testing is started from the air and the displacement offset is automatically corrected.

Supporting Components

The components of the NTI (e.g., the automated testing assembly 100) use various electronics, computer, a controller such as an SPM-type controller (e.g., a scanning probe microscopy type controller including, but not limited to, a scanning tunneling microscopy type controller), a video display monitor, etc. found in one example in the control station 110.

Software

Multi-User Level Software

In one configuration, the software that operates the system (for example, the Hysitron's TriboScan Professional software), is configured to have two or more user levels, such as Administrator (full functionality), Engineer (limited functionality), and Operator (more limited functionality). In one embodiment, these defined user levels provide push-button type testing capability on a graphic user interface once the testing protocols are set up by the Administrator or Engineer levels. An embodiment is configured to include an easy to navigate user interface where the operator specifies the type of test to be performed (e.g., indentation/scratch), the predefined load/scratch function, and the testing location. Each setting is ideally selected on a single screen (tab) using, for example, a touch screen in the control station 110.

Machine Vision/Pattern Recognition

It may be advantageous to more specifically orient the sample (such as a wafer) prior to testing, even where a pre-aligner is employed by the handling system. Therefore, in one embodiment, in order to fine-tune the wafer orientation, machine vision is incorporated to further de-skew the wafer alignment. This assists in testing small discrete regions of a patterned substrate, or limits the introduction of defects to specific regions of the wafer. In one example, the de-skewing capability algorithms are implemented in the operating software. In an embodiment, this machine vision capability is configured to automatically identify specific regions of samples as well as identify and catalog (record x-y coordinates) of individual samples/test pieces and measure their size.

In another embodiment where testing is performed on materials or samples having irregular surface features, the NTI software is configured to image a portion of the sample surface (using, for example, an SPM, AFM, optical microscope, the optical instrument 610 or the like) and then apply pattern recognition software to that image that enables the device to automatically identify structures having patterns that fall within certain parameters. For example, where a user desires to perform indentation testing on samples comprised of MEMS devices, and where the user wants to tests specific features of said MEMS device, those features are identified by the pattern recognition software, the location of an acceptable test site is then calculated, and that feature is then automatically moved under the probe and the desired testing protocols are applied.

Automated Tip Area Function—Calibration

As mentioned above in the discussion of the optional wafer chuck, an embodiment includes an automated software function that positions the indentation tip over an unused portion (un-indented) of a fused quartz sample or other suitable tip calibration material (e.g., a diagnostic sample 1106) and conducts an indent and/or performs a user-definable number of indents to automatically calculate an area function and use this Tip Area Function (TAF or probe area function PAF) until the tip is replaced or recalibration is needed as described herein.

Automated Tip Area Function—Indentation

As mentioned above in the discussion of the optional wafer chuck, an embodiment includes an automated software function, for instance incorporated with the control station 110 or the electronics of the transducer assembly 700 that periodically checks at user-defined intervals (after a preselected number of days or number of testing operations (e.g., indents)) that the TAF is still accurate.

In another embodiment, a specific occurrence (for example the presence of atypical or unexpected test data, such as force and displacement data) initiates an automated TAF to determine whether the tip continues to operate within specified acceptable parameters. For example, indentation tips are typically much harder than the samples they indent. Nevertheless, tips (even diamond tips) wear out. Where a series of samples are tested and the results of those tests are expected to yield data that falls within certain parameters, and data is obtained that departs from those parameters, that data may be a result of a production-line problem resulting in the creation of abnormal material or, in the case of the semiconductor industry, damaged wafers. However, where the wafer itself is normal, the abnormal data could be due to excessive wear of the tip, requiring the tip to be replaced. Verifying the TAF (e.g., conducting diagnostics) can potentially rule out tip failure as a cause of abnormal data. Thus, if the material properties of the sample fall outside the user-definable specification range, the TAF is immediately checked before signaling that the process is producing unacceptable coatings (wafers, material and the like) and prompting a production line shut-down. Shutting down a product line in this manner (after checking the TAF) can save substantial cost by quickly identifying when that line is producing substandard products.

Automated Tip Shape Validation—Scratch

Similar to the TAF Calibration and the TAF Indentation, the system will incorporate an automated software function to calculate the radius of curvature of a scratch probe. Using a material of well known properties, a low-load indent is performed along with a calculation of the radius of curvature from a Hertzian fit. In one embodiment the system is configured to enable the customer to input the range of radii that are acceptable. Additionally, if the measurement provides a scratch result outside the acceptable level the instrument will check the radius of curvature before signaling a line shut-down.

Automated System Calibrations

In one example, the software provides the ability to automatically perform one or more of a periodic z-axis air calibration (e.g., a space calibration) or a tip-optics offset calibration (e.g., an H-pattern calibration, as described herein).

Automated Data Analysis

Immediately during and after each indentation test the software (e.g., incorporated in one or more of the transducer electronics 708, the control station 110 and the like) analyzes the force-displacement data measured with the mechanical testing instrument 610 to output a hardness and modulus (standard Oliver and Pharr analysis).

In an optional embodiment, the data (such as hardness and modulus data) is correlated to a specific sample or a specific set of samples. Using the semiconductor industry system as an example, the system correlates the test data to a specific wafer number, such that where a series of wafers are being tested, a wafer can be later located for, for example, later inspection or further processing. In one embodiment, the sample itself is assigned a unique number, such as a bar code or a number. In another embodiment, the sample itself is not marked, rather it is contained in a known position in a material storage module, such as a specified position in a FOUP corresponding to samples designated for further investigation.

Where the system is configured to conduct scratch testing, in one example, the software instructs that a scratch analysis is automatically performed and automated to identify the critical load event. This is accomplished by looking at the derivative of the measured parameters (normal displacement, lateral force, friction) and identifying a sudden change. Due to the wide ranging critical load 'signatures', in an embodiment, the user will define a sensitivity parameter that triggers the critical load reading. In another embodiment, there may be a number of events (as in the case with certain multilayer films) where only the nth event is recorded.

Aggregate Data Storage and Analysis

In one optional embodiment, a spreadsheet like program is used with the results of one or more tests and is saved to both the NTI computer, such as the control station 110, as well as on a remote server location. Numerous other electronic storage options are possible.

In another optional embodiment, sets of test data are aggregated and said aggregations of data are thereafter compared to other aggregations of data or to data from a specific test on a specific sample. By way of example and not of limitation, hardness and modulus data for a set of 100 wafers tested in January 2012 may be compared to hardness and modulus data of 100 wafers tested in February 2012, to determine whether they are A) substantially identical or whether B) the data so obtained from any comparison contains unexplained deviations. By storing historical data and aggregating that date in such a way that it may be utilized to examine relative differences over time, the system 100 will enable the user to more readily identify errors that may be due to substandard material, a potential failure of a fabrication process, human error, substandard batches of raw materials, favorable or unfavorable changes in production methods or equipment, the relative performance and accuracy of worker shifts, etc. Thus, while data relevant to a specific sample is valuable to the process, aggregate and managed data is a powerful tool, especially when compared to other aggregate data gathered not only by the present system, but data gathered outside the system and reviewed in combination with the data gathered from the system 100.

Material Handling System Handshake

In some embodiments including embodiments employing a material handling system, the system is configured with software to enable communication between the material handling system (such as an EFEM robotic handling system 200) and the NTI to establish, for example: when the instrument enclosure is open, permitting access to the interior of the instrument; when to load a sample, such as a wafer, into the NTI; and when to unload a sample (e.g. one or more wafers) once testing is concluded. In another embodiment, the control station 110 includes software instructions and the like that records what wafer is being tested, from where it was obtained, and where it is deposited after testing.

Dynamic Testing Based on System Meeting Minimum Damping Requirements

Different kinds of tests have different tolerances for disturbance. For example, high load indentation testing tolerates a higher level of vibration or other disturbance than low-load indentation testing. Thus, while all significant levels of vibration during nanomechanical testing are undesirable, testing may proceed and yield acceptably accurate results so long as disturbance levels are maintained within acceptable parameters even in a production (e.g., manufacturing) setting.

In one embodiment, the system is equipped with one or more sensors that detect disturbances that negatively impact the operation of the instrument. Where disturbances exceed a maximum threshold (optionally dictated by the user according to the test scenario performed, e.g., with differing thresholds automatically applied for each test) the automated testing assembly 100 is adaptive to automatically shut down, pause and/or suspend the test. The system 100 then resumes the test when said disturbances or other conditions are within acceptable limits. The sensors include, but are not limited to, transducers, accelerometers, and the like. Similarly, where specialty environments are required for testing, a wide variety of sensors can be employed to monitor, for example, the status of temperature controlled environments, vacuum levels, environmental issues (e.g., the presence or absence of particulate matter, vibration, humidity, and the like). When conditions fall outside of acceptable parameters, the system initiates an action, such as suspension of testing, stopping testing, activating a light tower, generating an error report, and the like.

Dynamic Testing

In some embodiments, the NTI (e.g., the automated testing assembly 100) is configured with multiple testing heads and indenter tips, imaging devices, and testing modules. While in many embodiments a user will run one test across multiple samples, the present system may be configured to run a variety of tests and generate additional data depending upon the data obtained from those tests.

For example, where a user is conducting a series of tests on, for example, MEMS devices or photovoltaic devices, and the data obtained from a nanoindentation test or scratch tests yields data having certain parameters, the system may be configured to automatically and adaptively conduct additional testing on that sample before returning to the standard testing routine. As one example, where a hardness measurement on a MEMS device yields what might be considered unexpected results, the system is configured to automatically reposition the sample using the X-Y stage or X-Y-Theta stage and relocate that sample and/or the test site on that sample in order to obtain an AFM image of the site, (for example) or an optical image for later analysis. In another example, the system 100 runs an additional series of tests on that sample as well, such as additional indentation tests, scratch tests, wear tests, modulus mapping or performs orthogonal testing techniques. Alternatively, the presence of abnormal test results or even a series of abnormal test results can trigger a tip diagnostic (on an aluminum or quartz block, such as the diagnostic samples 1106), tip replacement, or testing with a tip having alternative geometry before resuming testing on subsequent samples, for example.

Modulus Mapping

Modulus Mapping incorporates the quantitative measurements of viscoelastic properties provided by nanoscale dynamic mechanical analysis with the in-situ imaging of testing instruments to yield unprecedented capabilities in nanomechanical testing. This tool provides a modulus map of a surface from a single SPM scan, eliminating the need for thousands of indents to characterize an area. Metallic oxide films have been investigated extensively due to their relevance in the electronic, wear and corrosion fields. The metal/oxide interface is crucial in a variety of technologically important applications, including contacts in microelectronics, metal/ceramic composites, photovoltaic devices, electrochemical cells and gas sensors. The determination of the mechanical properties of these films is necessary for predicting the ability of the layer to survive in a realistic environment.

Because the thickness of these films can range from several nanometers to several microns, site specific characterization of the mechanical properties can be difficult. Modulus Mapping uses aspects of both nanoDMAT™ and SPM imaging to create nanoscale maps enabling visualization of both topographical and mechanical data of the metal/oxide interface.

Initial topographical data of the sample cross section enables visualization of (for example) the interface between the metal and the oxide film.

The increased complex modulus of the film implies that the layer may be suitable to act as a protective boundary over the metal surface which is crucial for metals with high wear applications. The systems and methods described herein, in one example, are configured to modulus map one or more samples through positioning and alignment of samples as described above, and nanomechanical testing of the mechanical properties of the surfaces of the samples.

Automated Testing Assembly

FIG. 1 shows one example of an automated testing assembly 100. As shown the automated testing assembly 100 includes in the example a sample storage and handling assembly 102. As shown in FIG. 1, the sample storage and handling assembly 102 includes one or more storage modules 104 and a sample handling module 106 coupled with an automated testing enclosure 108. As further shown in FIG. 1, the control station 110 is coupled with the automated testing enclosure 108. In still another example, the automated testing assembly 100 includes a control station 110 positioned remotely relative to the other components of the automated testing assembly 100, for instance, within a control room at a remote location and the like.

Referring again to FIG. 1, the sample storage and handling assembly 102 is shown as including a storage module 104. In the example shown in FIG. 1, the sample storage and handling assembly 102 includes a plurality of storage modules 104 coupled with the sample handling module 106. In one example, the storage modules 104 include but are not limited to front open unit pods (FOUP) sized and shaped to contain a plurality of semi-conductor wafers therein. When loaded into the sample handling module 106, the plurality of storage modules 104 provide a plurality of samples such as semi-conductor wafers for access by the handling module 106 and corresponding loading of the samples within the automated testing enclosure 108 for mechanical testing as described herein.

In another example, the sample handling module 106 includes but is not limited to an equipment front end module (EFEM) configured to manipulate samples in the storage modules 104 and position the samples within the automated testing enclosure 108 for mechanical testing.

The control station 110 as previously described is, in one example, coupled with the automated testing enclosure 108 of the automated testing assembly 100. Optionally, as also previously described the control station 110 is remote relative to the other components of the automated testing assembly 100. The control station 110, in one example, includes a series of controls, user interfaces, output devices such as monitors, printers and the like configured to assist the user in monitoring, controlling, observing test parameters, diagnostic characteristics and testing scenarios for the automated testing assembly 100. In still another example, the control station 110 is configured to assist the user in developing and implementing various testing scenarios for the samples contained in the sample storage modules 104.

Figure 2:
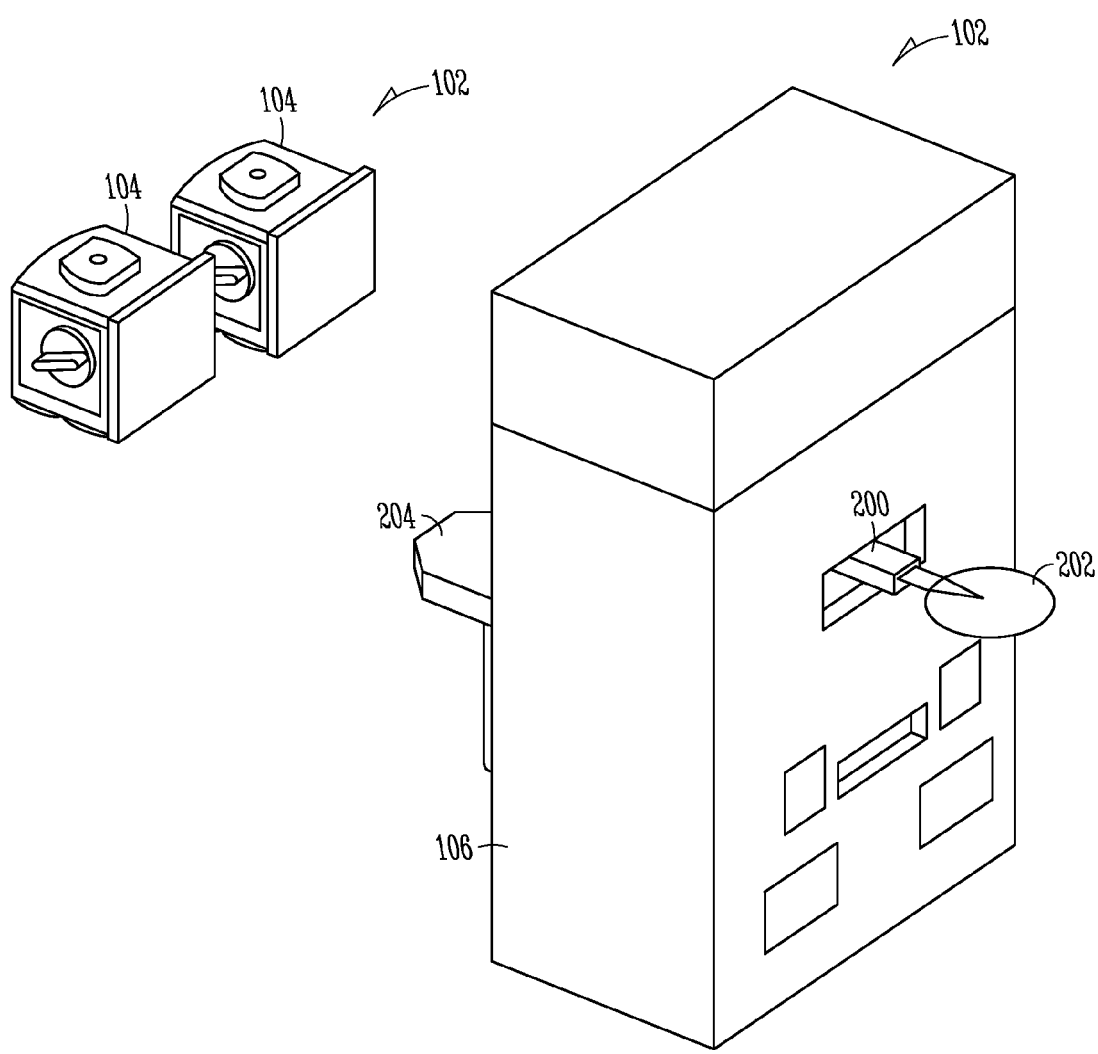
FIG. 2 is an exploded view of one example of a sample handling module and a plurality of storage modules.

Referring now to FIG. 2, the sample storage and handling assembly 102 is shown in an exploded view. As shown, the plurality of storage modules 104 are positioned away from the sample handling module 106. The sample handling module 106 includes storage module loading racks 204 sized and shaped to receive the storage modules 104 (e.g., FOUP) thereon. The sample handling module 106 is further shown with a robotic handling system 200 at least partially presented outside of the sample handling module 106. As shown in FIG. 2, the robotic handling system 200 includes a sample 202, such as a semi-conductor wafer presented thereon, for positioning within the automated testing enclosure 108 for mechanical testing as described herein.

Figure 3A:
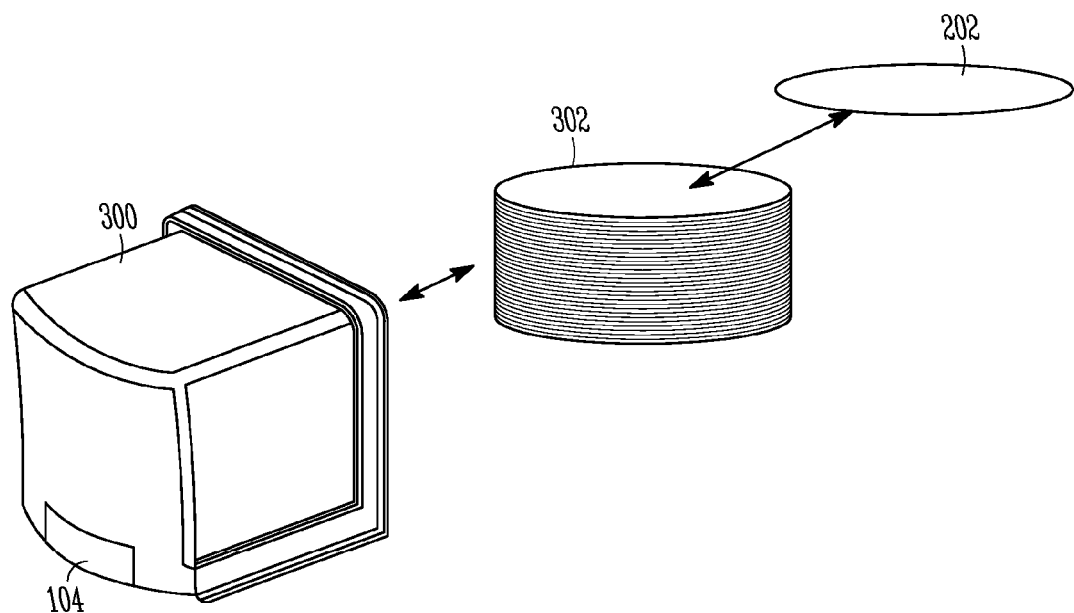
FIG. 3A is an exploded view of a storage module as shown in FIG. 2 including a plurality samples for storage therein.
Figure 3B:
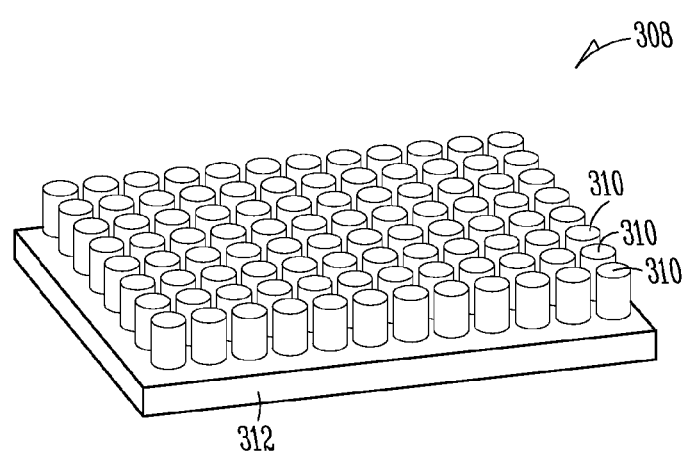
FIG. 3B is a perspective view of another example of a storage module including multiple samples for use with a sample handling module and an automated testing assembly.

FIGS. 3A and 3B show different examples of storage modules sized and shaped for containing a plurality of samples therein for testing with the automated testing assembly, such as the assembly 100 shown in FIG. 1. Referring first to FIG. 3A, the storage module 104 previously shown in FIGS. 1 and 2 is provided in an open configuration with a plurality of samples 302 positioned outside of a storage module case 300. In one example the sample 202, such as the semi-conductor wafer, is shown positioned away from the plurality of samples 302. As shown in FIG. 3A, in another example, the plurality of samples 302 are arranged in a stacked configuration and thereafter positioned within the storage module case 300 for storage and eventual retrieval by the robotic handling system 200 shown in FIG. 2. In yet another example, the storage module case 300 is specifically designed for fitting on or within the storage module loading rack 204 shown in FIG. 2. The storage module case 300, in one example, includes a port configured for opening by the sample handling module 106 to provide access to the plurality of samples 302 therein by the robotic handling system 200.

FIG. 3B shows another example of a sample module 308. As shown, the sample module 308 includes a sample module tray 312 sized and shaped to contain a plurality of samples 310 thereon. In one example, the plurality of samples 310 include but are not limited to biological samples, material samples and the like. Each of the samples 310 are positioned in a specified orientation on the sample module 312. For instance, the sample module tray 312 includes a plurality of recesses, ridges, cups, partitions and the like sized and shaped to receive the samples 310 therein and organize the samples on the sample module tray 312 for easy access by handling systems such as the robotic handling system 200 shown in FIG. 2. In one example, the samples 310 are arranged in a 2:3 ratio of samples, for instance, in the example shown in FIG. 3B in the samples 310 are arranged in a configuration of 8:12.

FIG. 4A shows one example of the sample handling module 106 from a top view. The sample handling module 106 includes the robotic handling system 200 previously described and shown in FIG. 2. The robotic handling system 200 is shown in two separate orientations. A first stored position orientation 408 is shown in FIG. 4A with the robotic handling system 200 coupled with a sample 202, for instance, at the storage module loading rack 204 corresponding to the storage module 104. The robotic handling system 200 is further shown in a loaded position 410 with the sample 202 in a configuration for positioning on a stage, for instance, a stage of the automated testing system as described herein.

As shown in FIG. 4A, the robotic handling system 200 includes a robotic base 400 and an articulating arm 402 extending from the robotic base 400. Further, in the examples shown, the articulating arm 402 includes one or more handling forks 404 sized and shaped to engage, lift and manipulate one or more samples 202 as shown in FIG. 4A. The articulating arm 402 is sized and shaped to move within the sample handling module 106 to readily position the sample 202 in the loaded position 410 by manipulating the articulating arm 402 through the access window 406. Similarly, the articulating arm 402 of the robotic handling system 200 is configured to retrieve the sample 202 from the automated testing system and reposition the sample 202 in the stored position 408, for instance, the storage module 104 (e.g., FOUP).

As described herein, the sample storage handling assembly 102 including the storage modules 104 and the sample handling module 106 as well as the automated testing system within the automated testing enclosure 108 shown in FIG. 1 are provided to efficiently and rapidly test the plurality of sample locations on the plurality of samples contained within the storage modules 104. The automated testing assembly 100 automatically and with minimal use or interaction is configured to carry out a plurality of testing scenarios with the samples 202 and thereby mechanically generate measurements and corresponding data for mechanical parameters of the materials of the samples 202.

Referring again to FIG. 4A, in one example, the sample handling module 106 includes a pre-aligner 412 as shown in FIG. 4A. In one example, the pre-aligner 412 pre-aligns the sample, such as the sample 202 (e.g., a semiconductor wafer), for eventual positioning within the automated testing assembly 100, for instance, the automated testing system described herein. That is to say the pre-aligner 412 is positioned in an intermediate position between the stored positioned 408 and the loaded position 410 shown in FIG. 4A. For instance, the pre-aligner 412 is positioned in a separate bay or within the enclosure of the sample handling module 106. The pre-aligner 412 engages with the sample 202 after withdrawal of the handling forks 404 to substantially prealign the sample 202 for aligned or substantially aligned positioning of the sample 202 in the loaded position 410 within the automated testing enclosure 108.

Figure 4B:
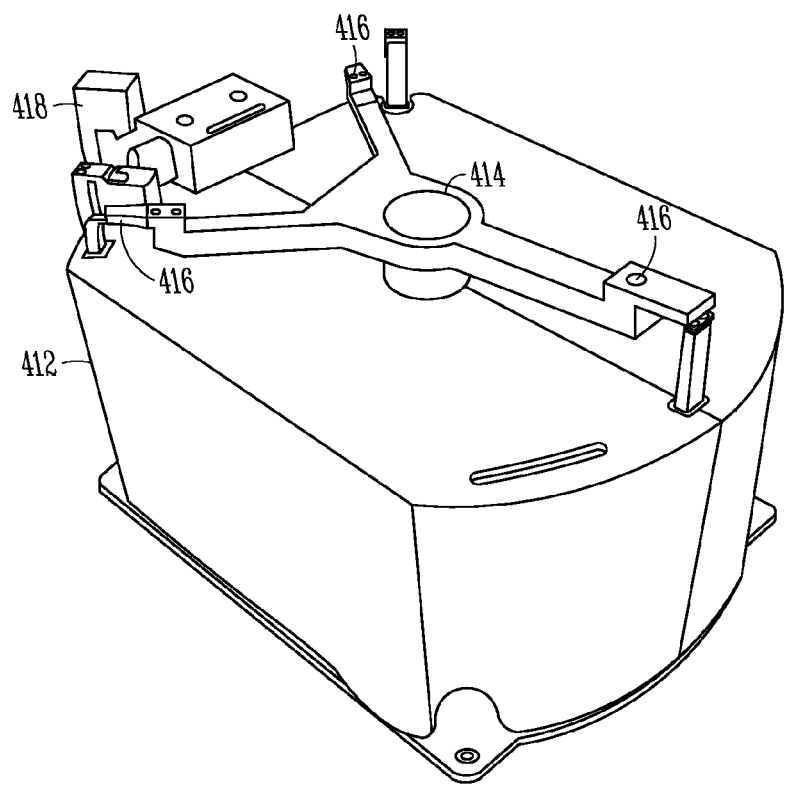
FIG. 4B is a perspective view of one example of a pre-aligner for use in the sample handling module of FIG. 2.

Referring now to FIG. 4B, one example, of a pre-aligner 412 is provided. In the example shown the pre-aligner 412 includes a pre-aligner stage 414, for instance, including a plurality of feet 416 extending away from a central portion of the pre-aligner stage 414. In one example, the pre-aligner stage 414 is operable to couple with and grasp a sample such as the sample 202 with the feet 416. The pre-aligner stage 414 is thereafter configured to rotate or translate (e.g., one or more) the sample 202 on the pre-aligner stage 414 relative to the alignment sensor 418. In one example, the alignment sensor 418 is configured to detect one or more indexing features on the sample 202, for instance, a notch in the sample 202. The indexing of the notch 202 allows for the prealignment of the sample 202 relative to the automated testing system contained within the automated testing enclosure 108. Stated another way the pre-aligner 412 prealigns the sample 202 for accurate positioning of the sample 202 for instance with the indexing features such as the notch in a desired orientation on the sample stage of the automated testing system contained within the automated testing enclosure 108.

After prealignment the articulating arm 402 including the handling forks 404 retrieves the sample 202 from the pre-aligner 412 and positions the prealigned sample in the loaded position 410 shown in FIG. 4A. In this orientation, the articulating arm releases the prealigned wafer onto the stage with the indexing feature such as the notch positioned as desired by the pre-aligner with only modest misalignment between the testing system stage and the sample 202. As described herein, the automated testing assembly 100 thereafter performs one or more of translational and rotational deskewing to ensure the accurate positioning of testing locations for testing by the mechanical testing instrument relative to the indexing feature. The testing system of the automated testing assembly 100 thereafter uses the sample stage 614 to position the sample so the desired testing location is positioned beneath the mechanical testing instrument 612 (or optical instrument 610) of the automated testing system.

Figure 5:
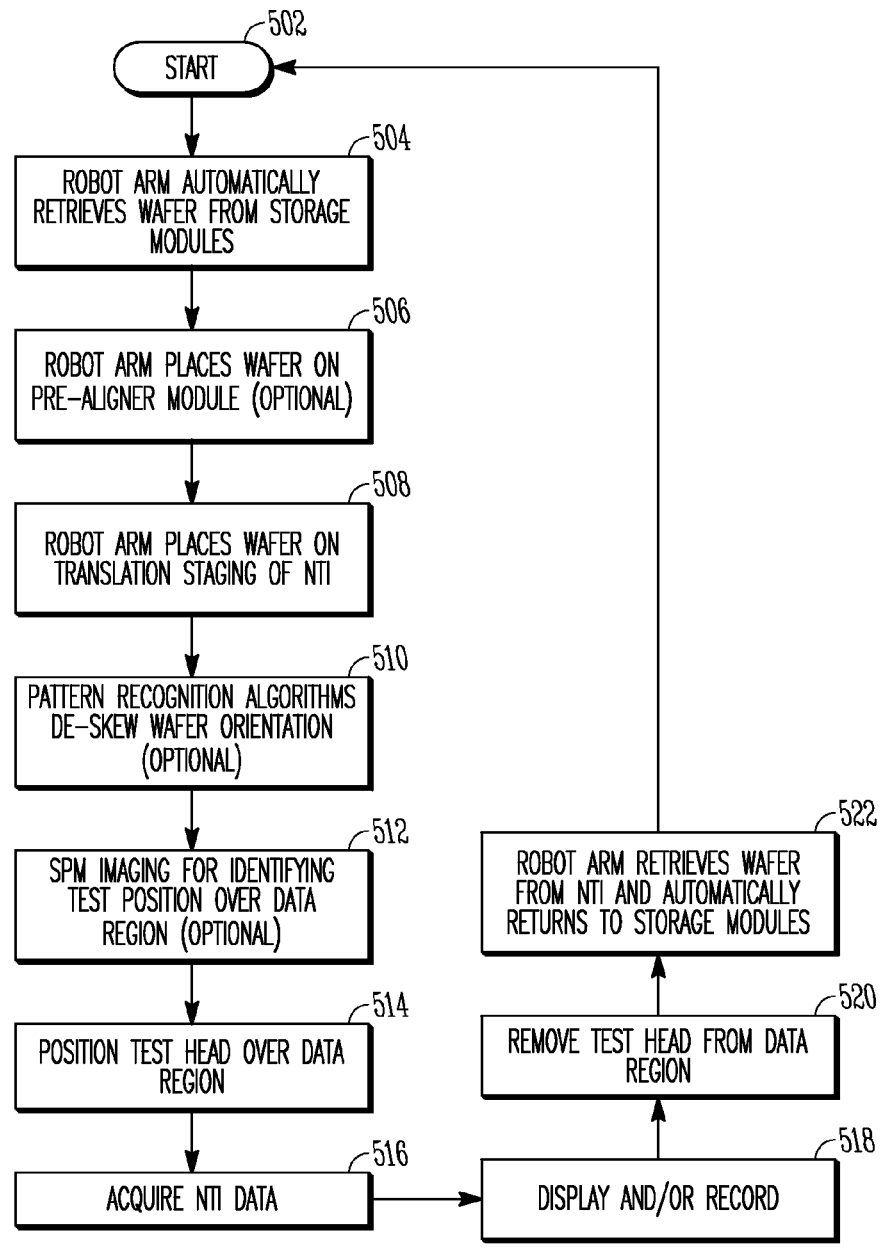
FIG. 5 is a block diagram showing one example of an automation method for mechanically testing one or more of a plurality of samples or a plurality of test locations on a sample with the automated testing assembly.

Overview of the Automated Testing Method Using the Automated Testing Assembly FIG. 5 shows one example of a method 500. The method 500 is conducted with the automated testing assembly 100 previously shown in FIG. 1 to mechanically test one or more of a plurality of samples or a plurality of test locations on a sample. In describing the method 500, reference is made to features and elements previously described herein including numbered references where convenient. The numbered elements provided within the description of the method 500 are not intended to be limiting. Instead numbered references are provided for convenience and further include any similar features described herein as well as their equivalents. At 502, the method 500 begins with the automated testing assembly 100 shown substantially in the configuration provided in FIG. 1. Stated another way, the sample storage handling assembly 102 is coupled with one or more storage modules 104 containing one or more samples 202 therein. The sample handling module 106 of the sample storage and handling system 102 is coupled with the automated testing enclosure 108 including the automated testing system therein. The control station 110 is further coupled with the automated testing enclosure 108. As previously described herein, control station 110, in one example, is remotely positioned and coupled with the automated testing enclosure 108, for instance, within a control room on a remote work site and the like.

At 504, a robotic arm automatically retrieves a sample from one of the storage modules 104. For instance, the articulating arm 402 including the handling forks 404 shown in FIG. 4A retrieves a sample from the storage module 104. At 506, the articulating arm 402 of the robotic handling system 200 places the sample on an optional pre-aligner module 412 as shown in FIG. 4A. At 508, the robotic handling system 200, for instance, the articulating arm 402 and the handling forks 404 places the sample 202 on a stage of the automated tested assembly 100 (for instance, a sample stage 614 shown in FIGS. 6A and 6B and described hereinbelow).

In another example, the method 500 further includes at 510 performing pattern recognition algorithms that deskew the sample 202 orientation relative to one or more of the sample stage and the automated testing system. For instance, the sample 202, in one example, is positioned in a substantially aligned configuration with the sample stage and the mechanical testing instruments of the automated testing enclosure 108 shown in FIG. 1. Some misalignment occurs between the sample 202 and the instruments or the sample stage. The pattern recognition algorithms deskew the orientation of the sample relative to one or more of the sample stage and the mechanical testing instrument to ensure accurate positioning of testing locations of the sample 202 relative to the mechanical testing instrument. Optionally, at 512 a supplemental instrument such as a scanning probe microscope (or the optical instrument 610) coupled with the automated testing system, for instance, adjacent to the mechanical testing instrument images the sample to identify test positions over the surface area of the sample 202.

At 514, the mechanical testing instrument, for instance, a probe is positioned over one or more desired testing locations, for instance, on a semi-conductor wafer the probe of the mechanical testing instrument is positioned over four or more separate locations of the sample according to indexing of the position through the pattern recognition deskewing operation and relative to the position of the indexing feature (notch) of the sample 202. At 516, the mechanical testing instrument is operated to acquire mechanical measurements of the sample 202, for instance, to generate one or more mechanical parameter measurements of the sample 202 with mechanical testing at one or more of the testing locations.

At 518, one or more of the measurements and the parameters generated from the measurements are displayed, for instance, at the control station 110 shown in FIG. 1. In another example, at 518, the results including the measurements and generated mechanical parameters are stored by the control station 110 or are instructed for storage by the control station 110 for instance at an offsite network memory location. At 520, the mechanical testing instrument is disengaged from the sample 202 to allow for withdrawal of the sample 202 from the automated testing enclosure 108 and positioning in the storage module 104. At 522, the robotic handling system 200 engages the sample 202 and repositions the sample from the loaded position 410 shown in FIG. 4A to the stored position 408 shown in FIG. 4A within one of the storage modules 104.

Automated Testing System

Figure 6B:
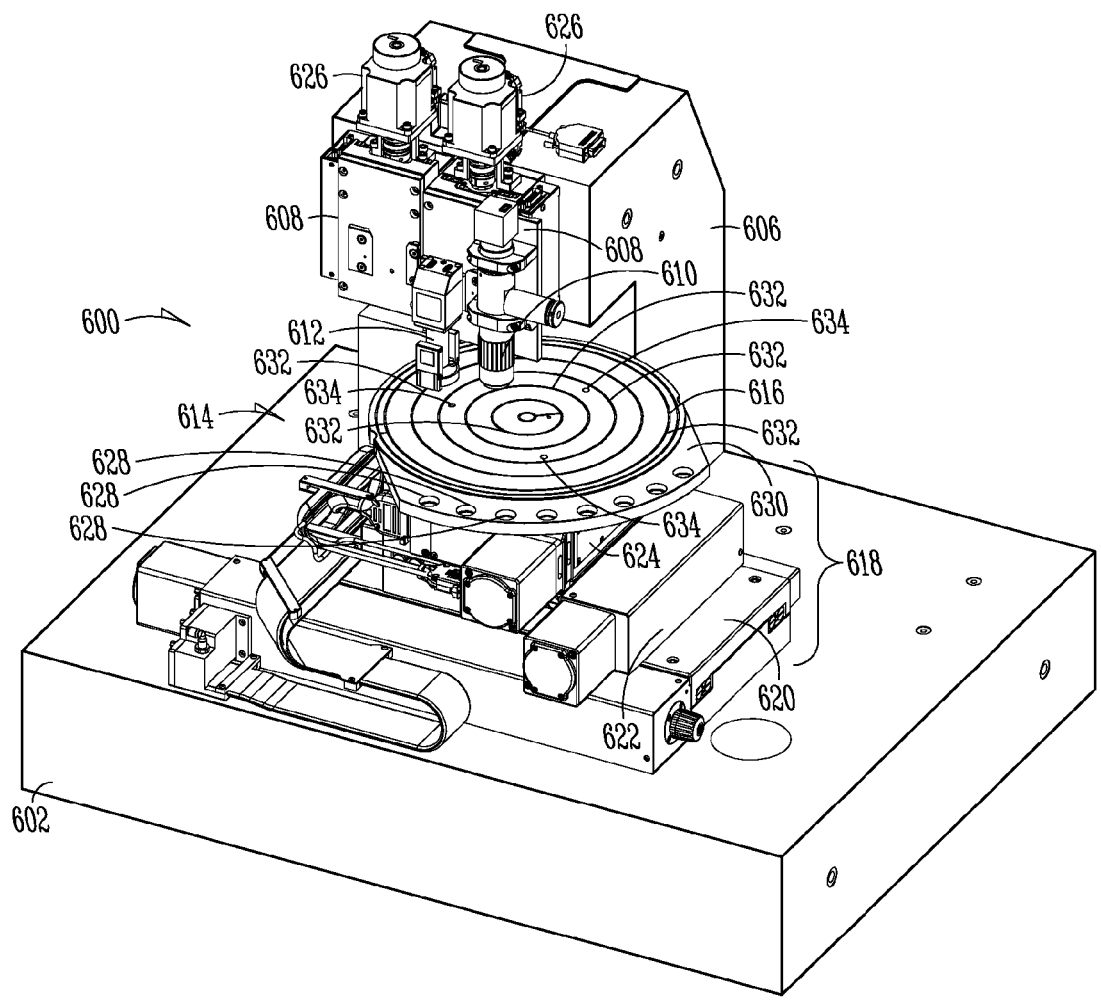
FIG. 6B is a detailed perspective view of the automated testing system shown in FIG. 6A.

Referring now to FIGS. 6A and 6B, one example of an automated testing system 600, for instance, for positioning within the automated testing assembly 100 shown in FIG. 1 is provided. As shown the automated testing system 600 includes a granite base 602 positioned on a system support table 604. In one example, the system support table 604 provides a framework underneath the granite base 602. For instance, the system support table 604 underlies the granite base 602 to provide a compact footprint for the overall automated testing system 600, for instance, within the automated testing assembly 100. A cantilevered instrument column 606 extends from the granite base 602 partially over a sample stage surface 616. The cantilevered instrument column 606 includes a column base 605 and a cantilevered arm 607. In one example, the cantilevered instrument column 606 includes one or more instrument stages 608 sized and shaped to receive and position the plurality of instruments relative to the sample stage surface 616. For instance, as shown in FIG. 6A the cantilevered instrument column 606 includes two instrument stages 608. As shown, one of the instrument stages 608 includes an optical instrument 610 and a mechanical testing instrument 612. In other examples as described herein, one Or more of the instrument stages 608 includes a plurality of instruments including an optical instrument 610 and a mechanical testing instrument 612. In other examples, as described herein one or more of the instrument stages 608 includes a plurality of instruments including an optical instrument 610, mechanical testing instrument 612 and another mechanical testing instrument such as high load mechanical testing instrument configured to provide indentation, scratches and the like at high force loads relative to the mechanical testing instruments 612. As described herein, the mechanical testing instrument 612 are configured to perform mechanical testing at micron (e.g., one or more microns) or nano scales on samples positioned on the sample stage surface 616. For instance, the mechanical testing instruments 612 are configured to provide one or more of indentation, scratching and the like upon samples positioned on the sample stage surface 616. Optionally, one or both of the mechanical testing instruments 612 and the optical instrument 610 include, but are not limited to, probes, probes having a Berkovich geometry tip, microscopes, electron guns, imagers, atomic force microscopes, manipulators or other instruments configured to ascertain physical or mechanical properties of a sample.

Referring again to FIG. 6A, the sample stage 614 is shown including the sample stage surface 616. As shown beneath the sample stage 614 a stage actuator assembly 618 is provided. In one example, the stage actuator assembly 618 is configured to move the sample stage 614 along or around a plurality of axis. The stage actuator assembly 618 is configured to move the sample stage surface 616 in one or more of the x and y axis. In still another example, the stage actuator assembly 618 is configured to move sample stage surface 616 rotationally, for instance, around the z axis (e.g., the stage actuator assembly is configured to provide rotational or theta movement). As shown, for instance, in FIG. 6A in one example the stage actuator assembly 618 includes a plurality of stages each comprising separate actuators configured to actuate the sample stage surface 616 into a variety of orientations to facilitate the positioning of substantially any testing location on sample stage surface 616 beneath the mechanical testing instrument 612 and the optical instrument 610 coupled with the instrument stage 608. For instance, the stage actuator assembly 618 includes in one example an x-stage 620. The x-stage 620 facilitates the movement of the sample stage surface 616 in a left to right direction relative to the view of the automated testing system 600 shown in FIG. 6A. In another example, the stage actuator assembly 618 includes a y-stage 622 coupled with the x-stage 620. In contrast to the x-stage, the y-stage 622 is configured to provide movement to the sample stage surface 616 in a direction substantially orthogonal to the x-axis of the x-stage 620. For instance, the y-stage 622 is configured to move the sample stage surface 616 into and out of the page of the view shown in FIG. 6A. In still another example, the stage actuator assembly 618 includes a rotational actuator such as a rotational stage 624 coupled with one or more of the x-stage and the y-stage 620, 622. In one example the rotational stage 624 provides full rotational movement of the sample stage surface 616, for instance, rotational movement through a full 360°. In another example, the rotational stage 624 provides a smaller degree of rotational movement such as a range of movement from 0 to 270° or from 0 to 180° or from 0 to 90° and the like. As will be described in further detail below the provision of multiple actuators, for instance, the x-, y- and rotational stages 620, 622, 624 facilitates positioning of substantially any location on the sample stage surface 616 and a sample overlying the sample stage surface 616 (e.g., the sample stage 614) underneath the plurality of instruments coupled with the instrument stage 608 (e.g., the optical instrument 610 and the mechanical testing instrument 612).

Each of the components of automated testing assembly including the automated testing system 600 are constructed with a variety of materials according to the testing methods appropriate for the system. For instance, materials including, but not limited to, ceramics, steels (tool and stainless steels), aluminum, other metals, composites, polymers and the like are used in one or more of the mechanical and optical instruments 612, 610, the sample stage 614, and the like. One or more of the components of the instruments, stage and the like (e.g., probe tips, shafts, housings and the like) may include alloys, such as invar, quartz, diamond, sapphire and other similar materials having predictable mechanical characteristics, including one or more of high hardness, low coefficients of thermal expansion and low thermal conductivities.

The instrument stage 608, the optical instrument 610 and the mechanical testing instrument 612 have a limited footprint relative to the automated testing system 600. For instance, the cantilevered instrument column 606 positions the optical and mechanical testing instruments 610, 612 over a substantially limited portion of the sample stage surface 616. In one example, the footprint of the optical and mechanical testing instrument 610, 612 is substantially minimal to the overall footprint of the sample stage surface 616. The stage actuator assembly 618 including the x-, y- and rotational stages 620, 622, 624 facilitates the movement of the sample stage surface 616, for instance, any location on the sample stage surface 616 to a position underneath the mechanical and optical testing instruments 612, 610 respectively. Stated another way, the mechanical and optical instruments 610, 612 are maintained in a substantially small footprint according to the limited cantilever of the cantilevered instrument column 606, and the sample on the sample stage surface 616 (e.g., a semiconductor wafer, other sample or the like) is rotated, translated, and the like to position substantially any testing location on the sample underneath the instruments 610, 612. The cantilevered instrument column 606 is thereby able to provide a stiff, solid support to the mechanical and optical testing instruments 610, 612 to provide reliable and accurate measurements of mechanical parameters of the sample tested by the mechanical and optical testing instruments 612, 610. Stated another way, large arch-type supports as opposed to the cantilevered instrument column 606, are substantially avoided through the use of a sample stage surface 616 as a component of the sample stage 614 where the stage actuator assembly 618 is configured to substantially move any testing location beneath the mechanical testing instrument 612 and the optical instrument 610 for testing. The automated testing system 600 thereby has a minimal footprint and can readily fit on a factory floor between other components, for instance, in a semiconductor production facility.

FIG. 6B shows a detailed view of the automated testing system 600 previously shown in FIG. 6A. As shown, the instrument stages 608 are provided on the cantilevered instrument column 606. In one example, the instrument stages 608 are provided with corresponding instrument actuators 626. In one example the instrument actuators 626 are configured to provide movement of the instruments such as the optical instrument 610 and the mechanical testing instrument 612 along an axis such as the z-axis relative to the sample stage surface 616 and a sample positioned thereon. In one example, the instrument actuator 626 includes in one example, but is not limited to, one or more screw drives configured to move part of the instrument stage 608 relative to the cantilevered instrument column 606. In one example, the instrument actuators 626 provide gross positioning of the mechanical and optical instruments 612, 610 relative to a sample on the sample stage surface 616. Optionally, the instrument actuators 626 include one or more actuators configured to provide one or more of X, Y and Z axes of movement and positioning of the instruments 610, 612 (e.g., orthogonally, parallel to the stage 614 and the like).

In still another example, the instrument actuators 626 work in concert with a transducer, for instance, within the mechanical testing instrument 612. For instance, the instrument actuator 626 provide an indentation or scratching force for an instrument probe of the mechanical testing instrument 612. The transducer within the mechanical testing instrument 612 is then solely relied upon to measure forces, indentation depths, and the like of the probe relative to the sample on the sample stage surface 616. Optionally, the instrument actuators 626 provide multiple degrees of translational movement (e.g., movement along the x, y and z axes) for the instruments coupled thereon.

As further shown in FIG. 6B, the sample stage 614 includes a stage receptacle flange 630 with the sample stage surface 616. Optionally, the stage receptacle flange 630 is integral to the sample stage surface 616 (and when referring to the sample stage surface 616 in one example the alignment of the surface with an instrument includes alignment of flange 630 with the instrument). For instance as shown in FIG. 6B, the stage receptacle flange 630 extends along a portion of the perimeter of the sample stage surface 616. The stage receptacle flange 630 includes at least one stage receptacle 628. As will be described in further detail below, in one example, the stage receptacle flange 630 includes a plurality of stage receptacles 628. The stage receptacles 628 are sized and shaped to receive one or more of diagnostic samples, probe change units, and the like configured to automate the diagnostics and calibration of probes and the exchange and installation of instrument probes within the mechanical testing instruments 612.

As further shown in FIG. 6B, the sample stage surface 616 includes a plurality of vacuum ports 632. The vacuum ports 632 are configured to provide a vacuum underneath a sample position on the sample stage surface 616. In the example shown in FIG. 6B, the vacuum ports 632 form concentric circles within the sample stage surface 616. The vacuum ports 632 are thereby able to retain a plurality of samples having different sizes on the sample stage surface 616. In yet another example, the vacuum ports 632 are formed by a plurality of orifices, for instance pin holes, in the sample stage surface 616. In such an example the vacuum ports 632 are readily able to vacuum and thereby retain a sample having an irregular shape (e.g., non-circular, elongate and the like) on the sample stage surface 616. In still another example, the sample stage 614 includes a plurality of elevation pins 634 positioned around the sample stage surface 616. The elevation pins 634 are operable to provide an elevated support base for a sample such as a semiconductor wafer positioned over the sample stage surface 616. For instance, when a semiconductor wafer is positioned over the sample stage 614, an elongate member may be positioned underneath the sample to hold the sample as it is positioned. The plurality of elevation pins 634 allow for positioning of the sample over the sample stage surface 616 while allowing the interposing of the elements, such as a robotic arm, between the sample stage surface 616 and the sample. After positioning of the sample on the sample stage surface 616, for instance on the elevated elevation pins 634, the robotic arm is removed and the elevation pins 634 are depressed to allow setting of the sample upon the sample stage surface 616. Thereafter, the vacuum port 632 are operated to hold the sample on the sample stage surface 616 while the stage actuator assembly 618 is operated to position the sample as desired relative to the mechanical testing instrument 612, for instance to position the instrument over a plurality of designated testing locations on the sample.

Mechanical Testing Instrument

Figure 7A:
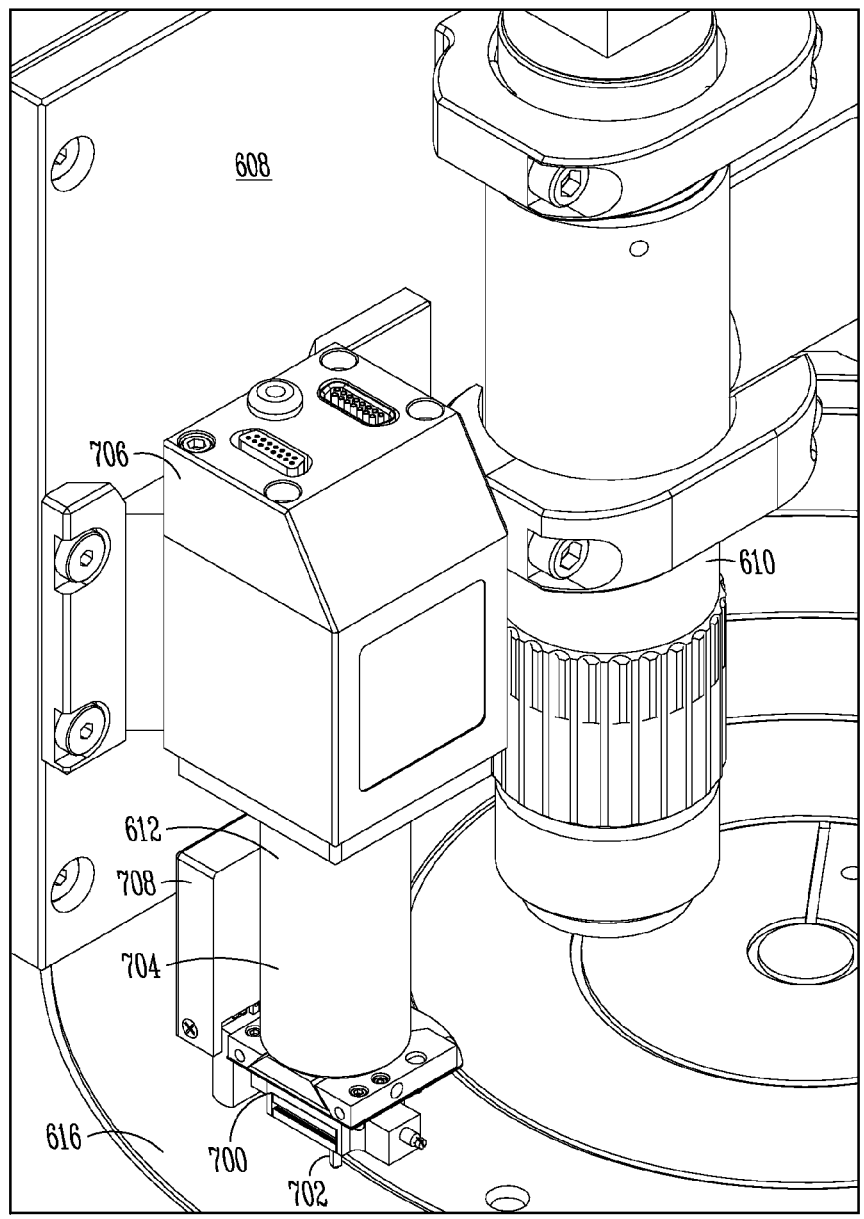
FIG. 7A is a perspective view of mechanical testing instrument and an optical instrument coupled with an instrument stage.
Figure 7B:
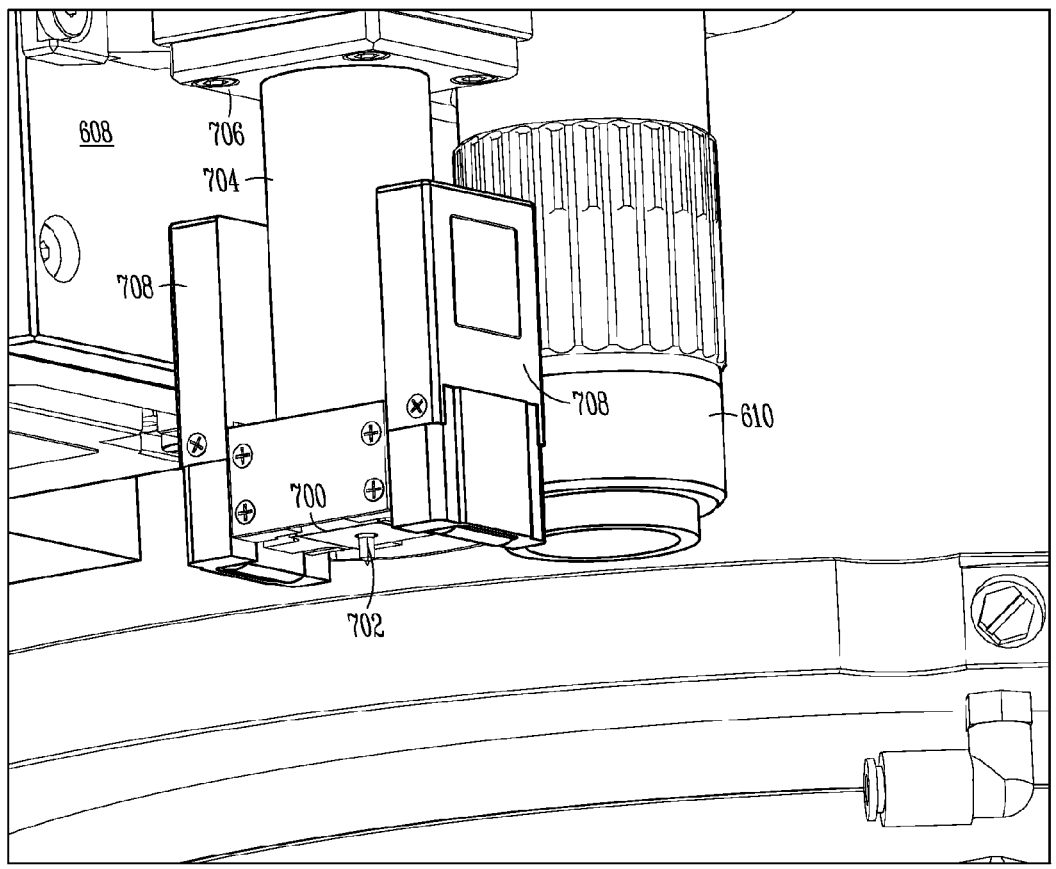
FIG. 7B is another perspective view of the mechanical testing instrument including the instrument tip and the optical instrument shown in FIG. 7A.

FIGS. 7A and 7B show one example of mechanical testing instrument 612 coupled with the instrument stage 608. As previously described in one example, the mechanical testing instrument 612 is positioned adjacent to an optical instrument 610 coupled with the same instrument stage 608. In another example, the positioning of the optical instrument 610 relative to the mechanical testing instrument 612 is fixed. For instance, where a testing location is identified with the optical testing instrument 610, a fixed specified distance between the optical instrument 610 and the instrument probe 702 (e.g., an instrument offset) allows for the ready positioning of the sample stage surface 616 and the testing location beneath the mechanical testing instrument.

Referring again to FIGS. 7A and 7B, the mechanical testing instrument 612, in one example, includes a transducer assembly 700 positioned adjacent to an instrument probe 702. In another example, the mechanical testing instrument includes an actuator 704. For instance, the actuator 704 includes but is not limited to a piezo actuator configured to move the instrument probe 702 along one or more axes such as the x-, y- or z-axis. The actuator 704 cooperates with one or more of the instruments stages 608 and the stage actuator assembly 618 to position the mechanical testing instrument 612 as needed over the sample on the sample stage surface 616. In one example, the actuator 704 provides gross positioning of the instrument probe 702 relative to the sample on the sample stage surface 616. The transducer assembly 700 in another example provides the movement and forces necessary to operate the instrument probes 702 in testing schemes including scratching and indentation while the instrument probe 702 is engaged with the sample on the sample stage surface 616. Optionally, the actuator 704 works in concert with the instrument probes 702 and the transducer assembly 700. For instance, the actuator 704 provides the indentation or scratching forces for the instrument probe 702 and the transducer assembly 700 provides measurement and sensing of the movement of the instrument probe 702 and the forces incident on the probe. The instrument probe 702 and the transducer assembly 700 thereby operate in a passive or substantially passive configuration while the actuator 704 provides the operating forces, displacement and the like. Optionally, the instrument probe 702 includes one or more instrument features, including, but not limited to tips having specified shapes and materials according to the testing schemes and samples tested (e.g., Berkovich geometry tips, conical geometry tips, diamond tips, quartz tips, composite tips, alloy tips, doped tips and the like).

Referring again to FIG. 7A, in one example, actuator electronics 706 are provided at one end of the actuator 704. In one example, the actuator electronics 706 include controls, circuit boards, memory, wiring and the like configured to operate the actuator 704. In another example, transducer electronics 708 are positioned adjacent or remote to the transducer assembly 700. As shown in FIG. 7A, the transducer electronics 708 are positioned outside the transducer assembly 700 but in electrical communication with the transducer assembly. Referring to FIG. 7B, a plurality of transducer electronic units 708 are positioned on either side of the transducer assembly 700. In one example, the transducer electronics 708 provide control modules, measurement modules and operation modules for the transducer assembly 700. In another example, wiring and the like are fed through the actuator 704 and the actuator electronics area 706 to provide electrical coupling of the mechanical testing instrument 612 with controls such as the control station 110 shown in FIG. 1. In a similar manner the electronics of the optical instrument 610 are similarly electrically coupled with the control station 110. In yet another example, each of the optical and mechanical testing instruments 610, 612 are coupled with the control station through one or more of IR, wireless, Bluetooth and related non-wired systems.

Figure 7C:
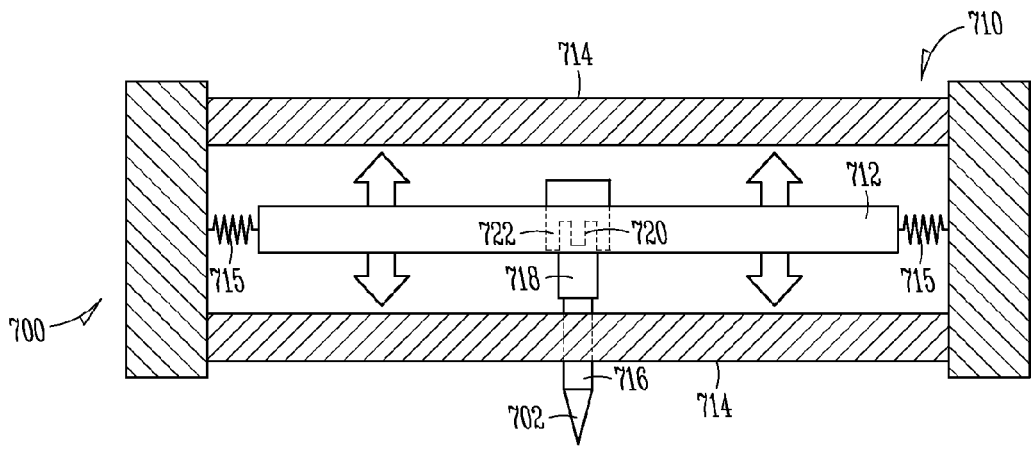
FIG. 7C is a schematic diagram showing one example of a transducer assembly.

Referring now to FIG. 7C, one schematic example of the transducer assembly 700 shown in FIGS. 7A and 7B is provided. The transducer assembly 700 shown in FIG. 7C includes a capacitor assembly 710 including opposed plates 714 positioned around a center plate 712. As shown in the diagram the center plate 712 is movable relative to the opposed plates 714. For instance, the center plate 712 is coupled with the remainder of the capacitor assembly 710 with one or more spring supports 715. The application of a voltage across the opposed plates 714 operates the center plate 712 to move the instrument probe 702 for indentation (e.g., along the z-axis) or translation (e.g., along the x- and y-axes). Similarly, movement of the center plate 712 relative the opposed plate 714 is measurable according to changes in capacitance, changes in the voltage across the opposed plates 714 and the like. Measurement of the change in capacitance and change in voltage is readily associated with the change in position of the instrument probe 702. From these measurements forces incidents on the instrument probe 702 as well as movement of the instrument probe 702 are readily determined with precision.

Referring now to the instrument probe 702, the instrument probe 702 includes a probe surface 716 coupled with a probe base 718. In one example, the probe base 718 includes a probe coupling feature 720 such as a threaded hole. The center plate 712, in one example includes a probe receptacle 722 sized and shaped to receive the probe base 718. In one example the probe receptacle 722 includes a threaded projection sized and shaped to couple with the probe coupling feature 720 of the probe base 728. For instance, with rotation of the probe base 718 the probe coupling features 720 receive and engage with the elongated projection of the probe receptacle 722 to securely fasten the instrument probe 702 to the center plate 712 of the capacitor assembly 710.

In one example, the capacitor assembly 710 operates in an electrostatic manner to move the center plate 712 relative to the opposed plates 714. For instance, the opposed plates 714 provide an electrostatic force to the center plate 712 that provides one or more of indentation or scratching movement of the instrument probe 702 relative to a sample, for instance, coupled on the sample stage surface 616 as shown in FIGS. 6A and 6B.

As previously described in some examples, the actuator, such as the actuator 704 or instrument actuator 608, provides movement including scratching movement, indentation movement or the like with the instrument probe 702 relative to the sample. The capacitor assembly 710 is used in this passive or substantially passive manner to measure the movement of the instrument probe 702 relative to the opposed plates 714 (e.g., by movement of the center plate 712). For example, in a passive mode the center plate 712 is held between the opposed plates 714 with the spring support 715. As the actuator 626 or 704 moves the instrument probe 702, for instance indenting the instrument probe 702 or scratching the instrument probe 702 across or into a sample, the deflection of the center plate 712 relative to the opposed plates 714 is measured to thereby determine the force incident on the instrument probe 702 as well as its movement.

In yet another example, the center plate 712 is held at a substantially static position relative to the opposed plates 714 with an electrostatic force. In this example, one or more of the actuators 704, 626 are operated to move the instrument probe 702, for instance indenting or scratching the instrument probe 702 into or along a sample, and the voltage required to maintain the center plate 712 in position relative to the opposed plates 714 is measured to determine the force incident on the instrument probe 702 corresponding to the force applied to the sample. The movement of the actuator 704 or 626 is used to correspondingly measure the movement of the instrument probe 702 where the instrument probe 702 is otherwise statically maintained relative to the opposed plates 704 (e.g., where the instrument probe 702 is coupled with the center plate 712).

Figure 8:
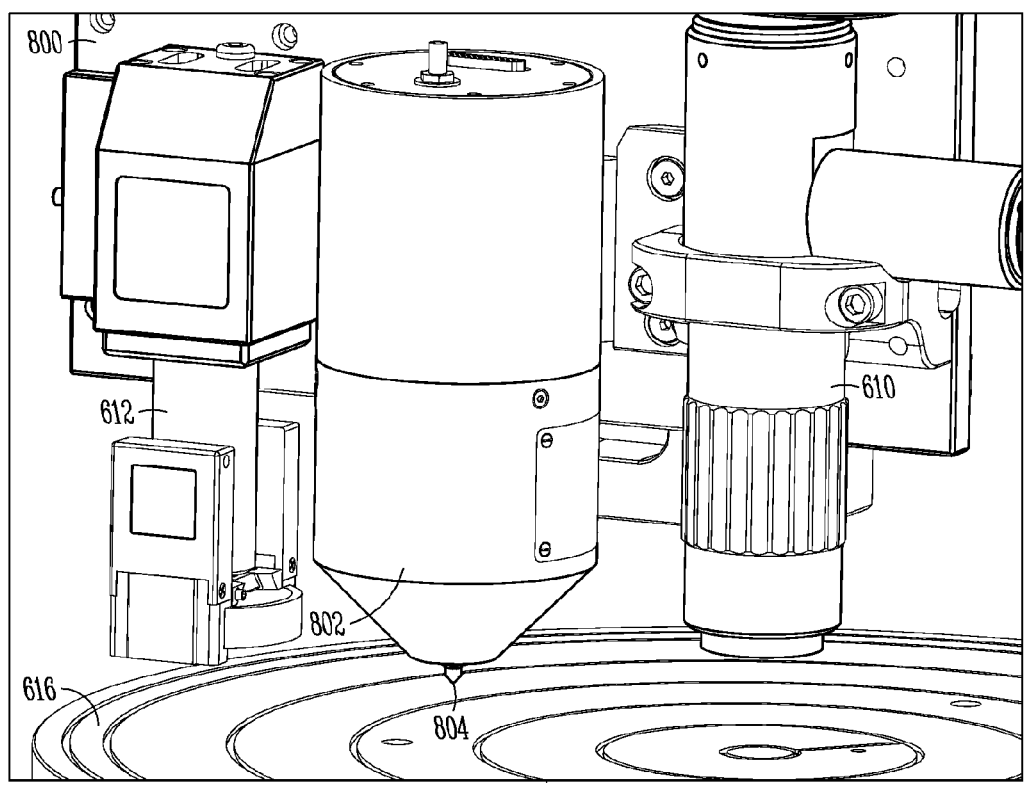
FIG. 8 is a perspective view of an instrument stage coupled with a low load and high load mechanical testing instruments and an optical instrument.

FIG. 8 shows another example of an instrument stage 800. In the example shown, the instrument stage 800 includes a plurality of instruments including the optical instrument 610 and the mechanical testing instrument 612 previously shown in FIGS. 6A and 6B. In the example shown in FIG. 8, the instrument stage 800 further includes a high load mechanical testing instrument 802. The high load mechanical testing instrument 802 includes a high load instrument probe 804 movably coupled within the high load mechanical testing instrument 802. In some examples, the high load mechanical testing instrument 802 includes a more robust capacitor assembly 710 and the high load instrument probe 804 to facilitate the application of higher forces to the sample positioned on the sample stage surface 616. The high load mechanical testing instrument 802 in combination with the mechanical testing instrument 612 is thereby able to provide a full suite of operational forces and the like to samples present on the sample stage surface 616 without requiring the exchange of instruments on the instrument stage 800. For example, the high load mechanical testing instrument 802 is configured to provide higher forces (e.g., up to around 10 N or more) relative to the forces provided by the lower force mechanical testing instrument 612 (e.g., up to around 10 micro N). As previously described with regard to the mechanical testing instrument 612 relative to the optical instrument 610, in one example the high load mechanical testing instrument 802, for instance its high load instrument probe 804, has a set specified position relative to the optical instrument 610. By providing a set distance (e.g., instrument offset) between the high load instrument probe 804 and the optical instrument 610 the high load mechanical testing instrument 802 is accurately and precisely positioned at a testing site location observed with the optical instrument 610.

Figure 9:
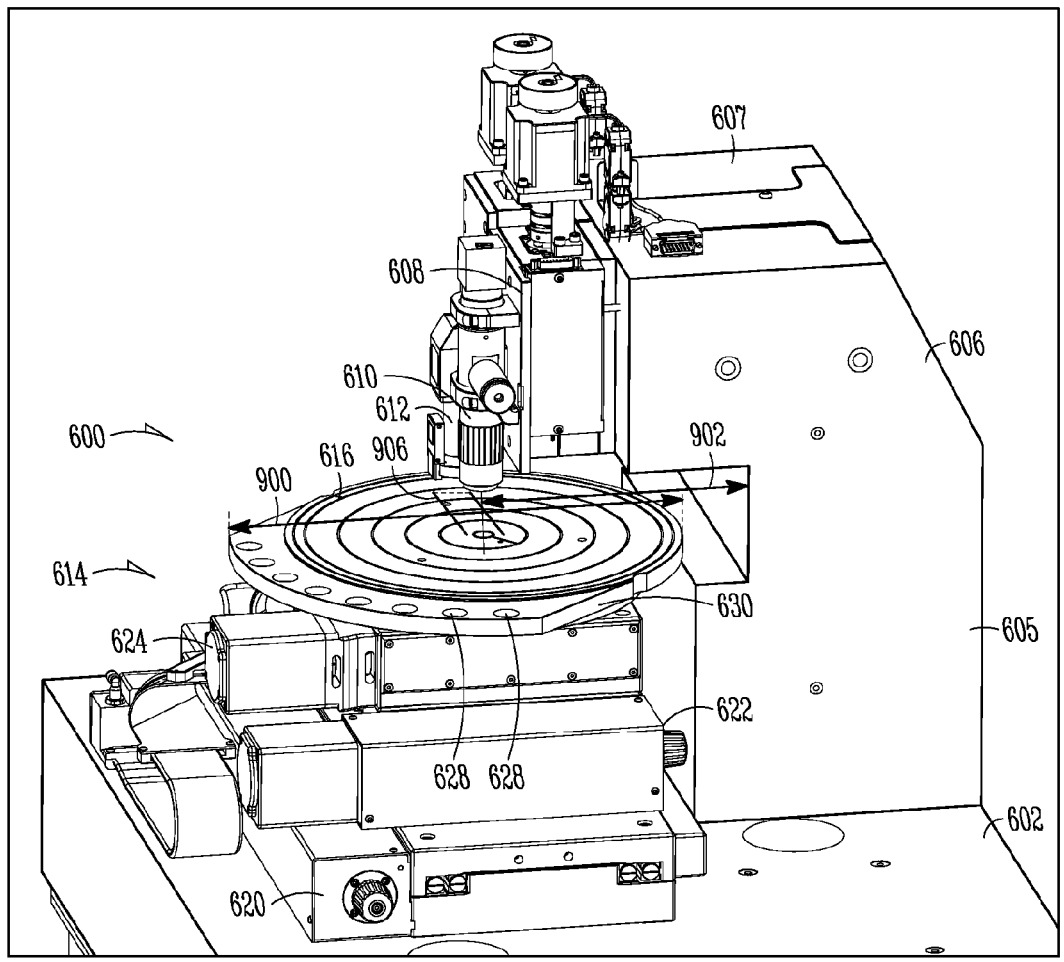
FIG. 9 is a perspective view of one example of a cantilevered instrument column and a sample stage including a sample stage surface and an X, Y and Theta degree of freedom stage actuator assembly.

Cantilevered Instrument Column and a Translational and Rotational Stage for Use with the Same FIG. 9 shows a side perspective view of the automated testing system 600 previously shown and described in FIGS. 6A and 6B. The view shown in FIG. 9 shows the relative position of the optical and mechanical testing instruments 610, 612 when coupled with the cantilevered instrument column 606 relative to the sample stage 614 including the sample stage surface 616. As shown, the cantilevered instrument column positions the instruments 610, 612 at an instrument-column length 902 over top of the sample stage surface 616. The sample stage surface 616 has a stage surface length 900 substantially larger than the instrument-column length 902. The sample stage 614 including the sample stage surface 616 is moved to provide access to each of the locations on the sample stage surface 616 with the stage actuator assembly 618 previously described herein. As previously described, in one example the stage actuator assembly 618 includes a plurality of stages, for instance an x-stage, a y-stage and a rotational stage 620, 622, 624, configured to position the sample stage surface 616 so that substantially any location on the sample stage surface 616 as well as any of the stage receptacles 628 on the stage receptacle flange 630 are capable of being positioned underneath one or more of the instruments such as the optical instrument 610 and the mechanical testing instrument 612.

In one example the instruments 610, 612 have a limited footprint such as an instrument footprint 906 shown in broken lines in FIG. 9. For instance, the instruments 610, 612, such as the optical and mechanical instruments, are configured to overlie an area of the sample stage surface 616 (e.g., the instrument footprint) according to their cantilevered position provided by the cantilevered instrument column 606. Stated another way, the limited instrument-column length 902 shown in FIG. 9 correspondingly constrains the position of the optical and mechanical testing instruments 610, 612 to the instrument footprint 906 shown in FIG. 9. The constrained positioning of the optical and mechanical testing instruments 610, 612 according to the cantilevered instrument column 606 provides a robust structurally supported base for the mechanical testing instrument 612 to substantially minimize mechanical noise in the mechanical testing instrument 612 during operation including indentation, scratching and measurement of scratching and indentation forces and indentation depth by the mechanical testing instrument 612. As shown, the cantilevered instrument column 606 provides a constrained instrument-column length 902 to minimize any deflection of the cantilevered instrument column extending over the sample stage surface 616.

The stage actuator assembly 618 in combination with the sample stage 614 having the sample stage surface 616 provides the flexibility to the sample stage surface 616 needed to position substantially any location on the sample stage surface 616 under any one of the optical or mechanical testing instruments 610, 612. Additionally, the stage actuator assembly 618 (e.g. configured for translation along x- and y-axes as well as rotation about the z-axis or theta rotation) is configured to position a plurality of the stage receptacles 628 and the stage receptacle flange 630 under the mechanical testing instrument 612. That is to say, with a combination of one or more of X and Y translation along with rotation of the sample stage surface 616 for instance with the x-stage, the y-stage and the rotational stage 620, 622, 624 substantially any location on the sample stage surface 616 is configured for positioning within the constrained instrument footprint 906 shown in FIG. 9. With this configuration a cantilevered instrument column 606 provides a relatively short cantilevered extension for the instruments over top of the sample stage surface 616 without otherwise requiring a corresponding duplicated column, such as an arch positioned on the opposed side of the cantilevered instrument column 606 shown in FIG. 9. The provision of a second column such as the column 606 shown in FIG. 9 to provide an arch would greatly increase the overall footprint of the automated testing system 600 and thereby the corresponding footprint of the automated testing assembly 100 shown in FIG. 1. In contrast, the automated testing system 600 shown in FIG. 9 has a compact footprint provided by the compact cantilevered instrument column 606 used in combination with the stage actuator assembly 618 configured for one or more of X, Y and rotational movement as described herein.

In one example, the x-stage 620 of the stage actuator assembly 618 is configured to have a greater range of movement relative to the range of movement of the y-stage 622. Stated another way, the sample stage 614 is configured to move into and out of the page as shown in FIG. 9 to a greater degree as opposed to transverse movement (e.g., along the y-axis) of the sample stage 614, for instance to the left and the right of the page shown in FIG. 9. By constraining the movement of the sample stage surface 616 to a large degree along the x-axis of the x-stage 620 the footprint in the direction transverse to the x-axis (e.g., along the y-axis of the y-stage 622) is substantially minimized The corresponding footprint of the automated testing system 600 is thereby further minimized to substantially limit the translation of the sample stage surface 616 to the left or right of the page shown in FIG. 9. The automated testing system is fully contained within the automated testing assembly 100 shown in FIG. 1 without requiring a larger enclosure otherwise needed with a sample stage 614 configured to move extensively along the y-axis with the y-stage 622 (e.g., to a similar degree to the x-stage range of translation).

In one example, the rotational stage (a theta stage) 624 provides added flexibility needed to substantially move any position on the sample stage surface 616 normally positioned by a y-stage having a greater range of motion. That is to say, the rotational stage 624 provides an additional degree of freedom to the stage actuator assembly 618 that minimizes the need for a large translational range for the y-stage 622.

Sample Stage Surface

Figure 10A:
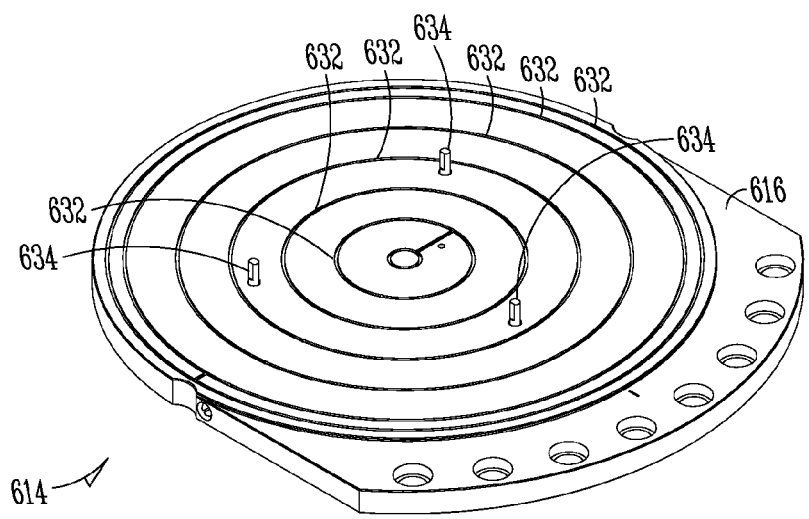
FIG. 10A is a perspective view of one example of a sample stage surface with a plurality of elevation pins elevated relative to the sample stage surface.
Figure 10B:
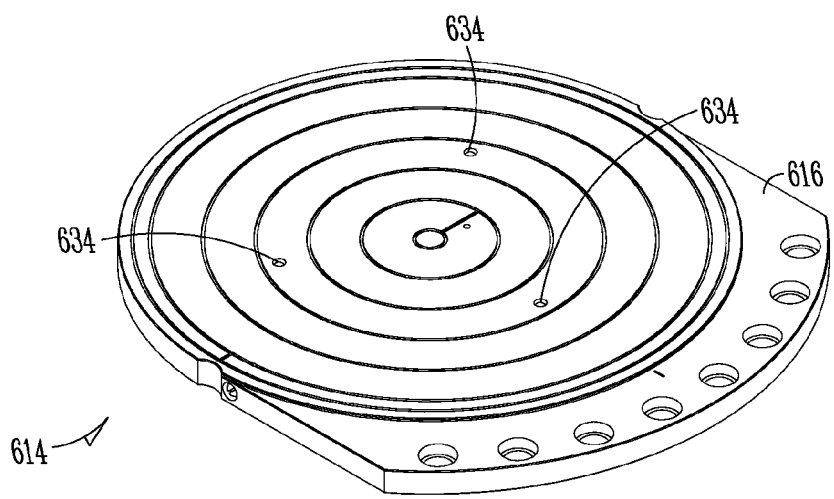
FIG. 10B is a perspective view of the sample stage surface of FIG. 10A with the plurality of elevation pins substantially flush relative to the sample stage surface.

FIGS. 10A and 10B show one example of the sample stage surface 616 previously described and shown in FIGS. 6A and 6B. For instance, the sample stage surface 616 includes a plurality of vacuum port 632 shown in concentric rings in FIGS. 10A and 10B. As previously described, the sample stage 614 further includes a plurality of elevation pins 634 sized and shaped to provide a support surface for a sample positioned on the sample stage surface 616 prior to retention for instance by the vacuum ports 632. That is to say, the elevation pins 634 provide an elevated resting surface for the sample to allow the interpositioning of a handling object such as a robotic arm between the sample stage surface 616 and the sample prior to fixing of the sample along the sample stage surface 616. The elevated pins shown in FIG. 10A allow the handling feature such as the robotic arm to position the sample and thereafter move from between the sample stage surface 616 and the sample without disturbing the sample's position or the sample stage surface 616. After disengagement and removal of the handling feature, such as the robotic arm, the elevation pins 634 are depressed as shown in FIG. 10B and the plurality of vacuum port 632 are operated to fix the sample to the sample stage 614 to allow for positioning of one Or more testing locations relative to the instruments such as the optical and mechanical testing instruments 610, 612 shown in FIGS. 6A and 6B without relative movement between the stage 614 and the sample.

Probe Change Assembly

Figure 11A:
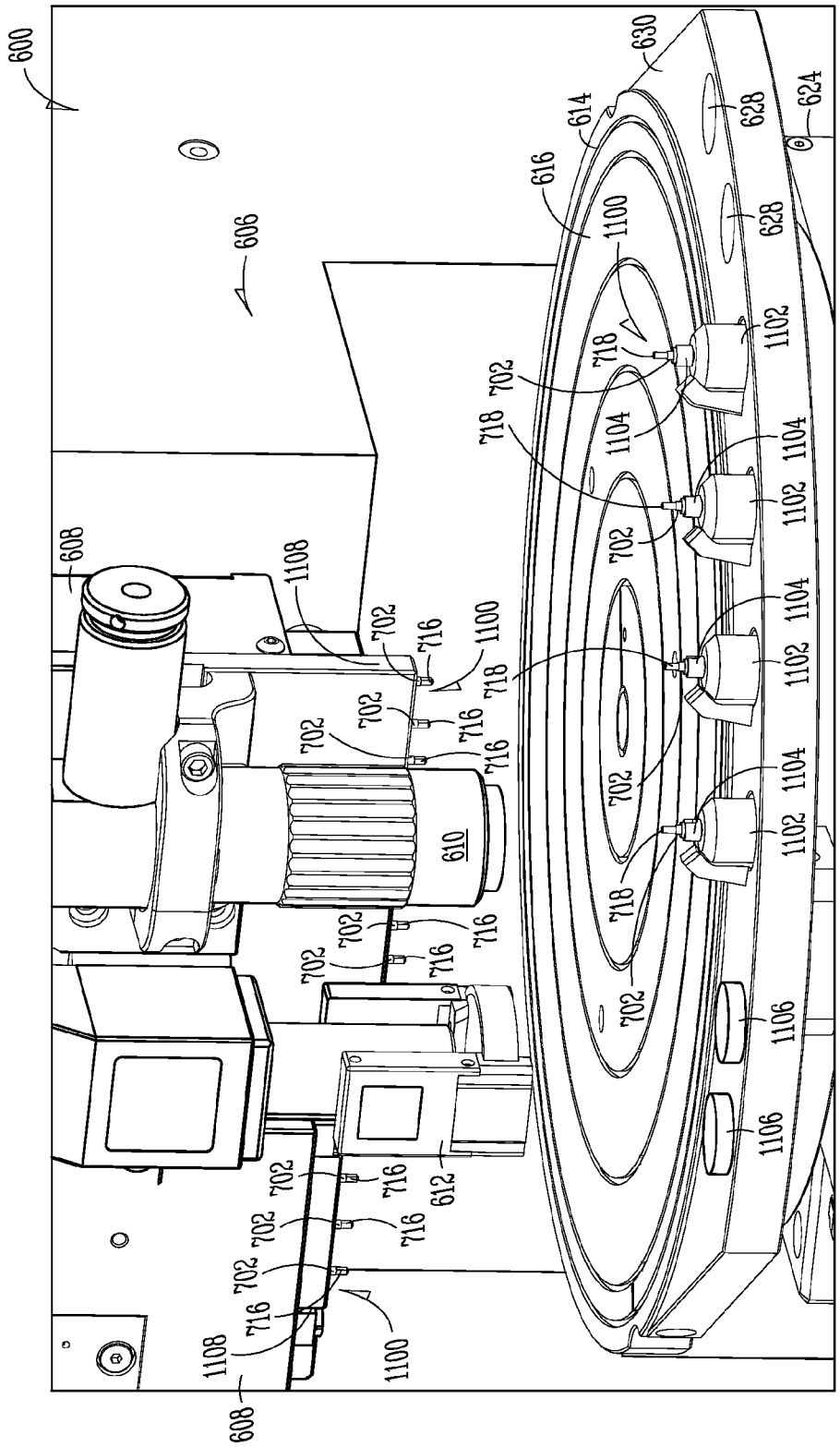
FIG. 11A is a detailed perspective view of the automated testing system including a tip changing assembly.

FIGS. 11A and 11B show portions of the automated testing 600 previously shown in FIGS. 6A and 6B. In FIGS. 11A and 11B the components of a probe change assembly 1100 are provided. The probe change assembly 1100 in one example includes a plurality of probe change units 1102 positioned within stage receptacles 628 along the stage receptacle flange 630 of the sample stage 614. As shown, each of the probe change units 1102 in one example includes a probe change tool 1104 coupled with a probe 702. Each of the probes 702 (e.g., instrument tips having specified shapes, materials and the like) are positioned within the probe change tools 1104 with the probe base 718 exposed for ready coupling with the mechanical testing instrument 612 coupled with the cantilevered instrument column 606.

In another example, the probe change assembly 1100 further includes a probe magazine 1108 coupled with a portion of the automated testing system 600. In one example, the probe magazine 1108 is coupled with the cantilevered instrument column 606 as shown in FIGS. 11A and 11B. In another example, and as shown in FIGS. 11A, B, the probe magazine is coupled with the instrument stage 608 and thereby movable at least along a Z-axis (e.g., vertically). The probe magazine 1108 in another example, is positioned anywhere within or on the automated testing system 600 where access is provided to the plurality of probes 702 by the plurality of probe change tools 1104 shown in FIGS. 11A and 11B. For instance, the probe magazine 1108 is positioned separately from the cantilevered instrument column 606 at a position to the side of the cantilevered instrument column where the plurality of probe change tools 1104 have access to the probe magazine 1108 to readily couple and decouple probes 702 from the probe magazine 1108 as needed for exchange with the mechanical testing instrument 612.

As shown in FIG. 11A, a plurality of probe change units 1102 are provided along the stage receptacle flange 630. In one example, the probe change tools 1104 are substantially identical and thereby able to couple with any of the probes 702 positioned within the probe magazine 1108. In another example, the probe change units 1102 include differing probe change tools 1104, for instance having differing diameters, cross-sectional shapes and the like. In such examples the probe change tools 1104 are sized and shaped to engage with differing probes 702 stored within the probe magazine 1108 or positioned within the probe change tools 1104 prior to operation of the automated testing system 600. For instance in one example, one or more of the probe change units 1102 include probe change tools 1104 sized and shaped for coupling with heavy load probes. In another example, one or more of the probe change units 1102 are, in contrast to the heavy load tools, sized and shaped for coupling with standard probes configured to operate at lesser forces relative to the heavy load probes used in the other probe change units 1102.

In another example, each of the stage receptacle 628 of the stage receptacle flange 630 are indexed to software control systems configured to operate the stage actuator assembly 618. The indexing of the stage receptacle 628 allows for the accurate and reliable positioning of the probe change units 1102 coupled within the stage receptacles 628 relative to the mechanical testing instrument 612 and the probe magazine 1108. Stated another way, the control system for the stage actuator assembly 618 is configured with the indexed positions of the stage receptacles 628 to move one or more of the probe change units 1102 when desired into alignment with the mechanical testing instrument 612 or various ports on the probe magazine 1108 for selective coupling and decoupling of probes 702 with the probe change units 1102. For instance, the stage actuator assembly 618 is configured to move the probe change units 1102 into alignment with one or more of the probes 702 stored within the probe magazine 1108, couple with one of the probes 702, and decouple the probe 702 from the probe magazine 1108. The stage actuator assembly 618 is thereafter configured to move through a combination of one or more of translation and rotation of the sample stage 614 to align the probe change unit 1102 and the probe 702 installed therein with the mechanical testing instrument 612. The probe change unit 1102 is configured to couple the probe 702 with the mechanical testing instrument 712 for instance through the elevation of one or more of the mechanical testing instrument 612 (e.g., the instrument stages 608 including the magazines 1108 thereon) or the sample stage 614 followed by rotation of the probe 702 by the probe change unit 1102.

Optionally, the probe change unit 1102 precedes the installation of a probe 702 within the mechanical testing instrument 612 with removal of a used probe from the mechanical testing instrument 612. In such an example, the probe change unit 1102 is aligned with the mechanical testing instrument 612 and the probe change tool 1104 engages with the probe 702 coupled with the mechanical testing instrument 612 and thereafter rotates the probe 702 out of coupling with the mechanical testing instrument 612. In one example, the probe change tool 1104 thereafter is moved for instance by the stage actuator assembly 618 (through a combination of one or more of translation and rotation) to align the probe change unit 1102 with one or more orifices in the probe magazine 1108. The probe change unit 1102 is raised or the probe magazine is lowered 1108 (for instance where the probe magazine 1108 is coupled with the instrument stage 608) into coupling engagement with the probe change unit 1102 having the used probe 702 thereon. The probe change unit 1102 positions the used probe 702 in an orifice of the probe magazine 1108 and decouples the probe 702 from the probe change unit 1102. The probe change unit 1102 is then free to receive a fresh probe 702 from the probe magazine 1108 for installation within the mechanical testing instrument 612.

In another example, the stage receptacle flange 630 includes one or more diagnostic samples 1106 positioned in one or more of the stage receptacles 628. In one example the diagnostic samples 1106 include, but are not limited to, quartz and aluminum samples having well known and predictable mechanical characteristics such as elastic modulus, hardness and the like. As with the probe change units 1102, having the diagnostic samples 1106 within the stage receptacles 628 allows for indexing of the diagnostic samples 1106 for accurate positioning of the samples by the stage actuator assembly 618. For instance, the stage actuator assembly 618, through control software, is readily able to move a diagnostic sample, through one or more of translation and rotation of the sample stage 614, into alignment with the mechanical testing instrument 612. The mechanical testing instrument 612 is operated to check the function of the probe 702 coupled with the mechanical testing instrument 612 (e.g., to check on probe wear, reassess the probe area function and the like).

In still another example the probe magazine 1108 includes a probe actuator configured to raise and lower the probe magazine 1108 relative to the probe change units 1102, to move one or more of the probes 702 into engagement with the probe change tools 1104 of the probe change units 1102, to couple and decouple probes 702 to and from the probe change units 1102 and the like.

Rotary Clutch

Figure 12A:
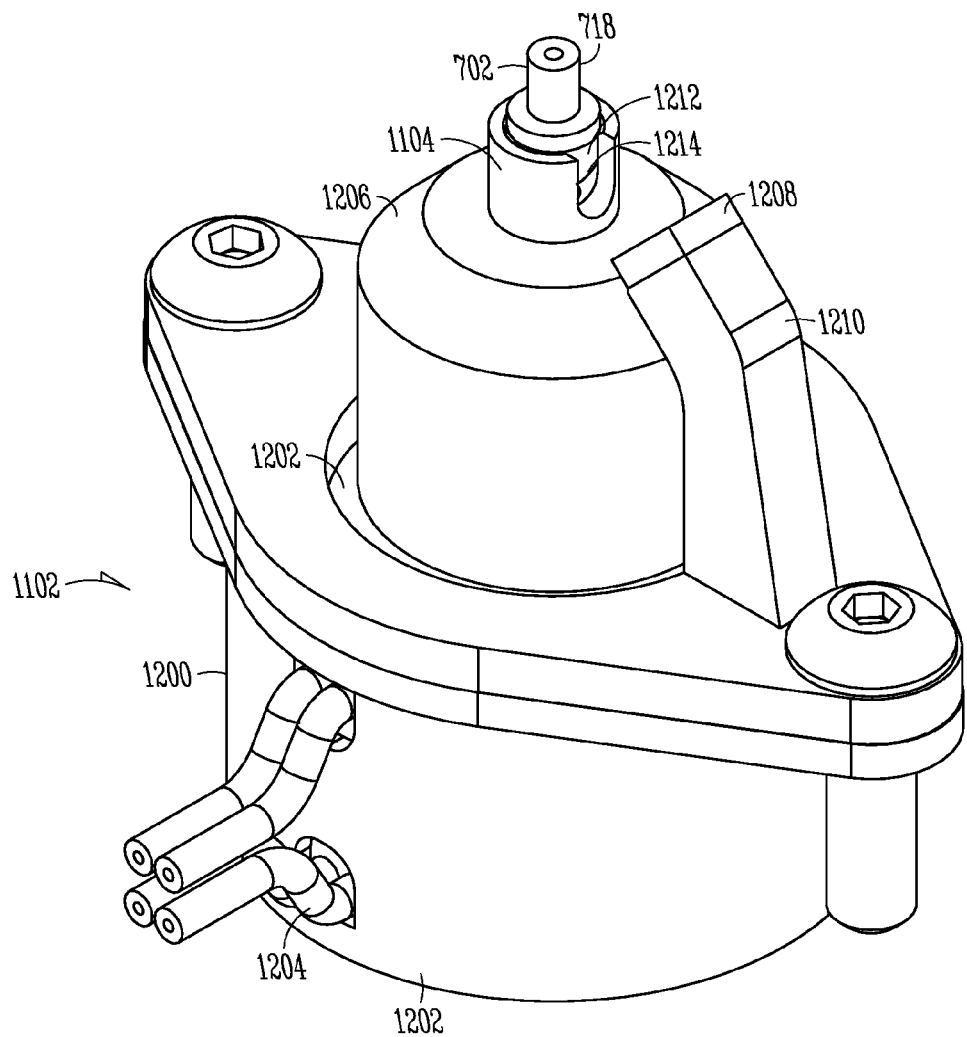
FIG. 12A is a perspective view of one example of a tip change unit.
Figure 12B:
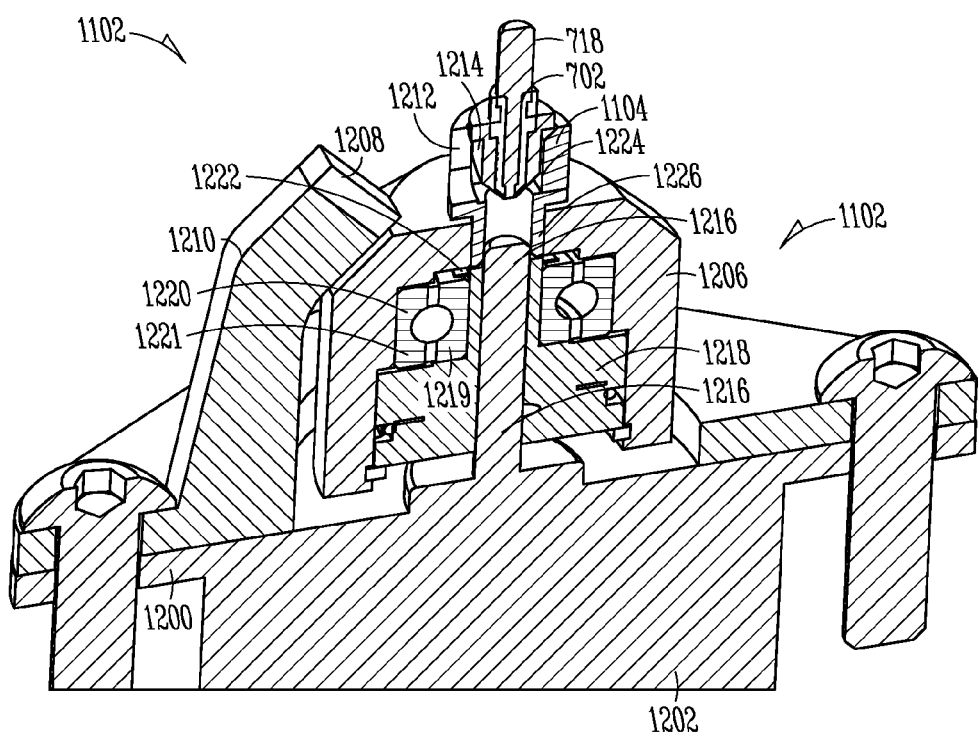
FIG. 12B is a cross sectional view of the tip change unit of FIG. 12A.

FIGS. 12A and 12B show views of one example of the probe change unit 1102 previously shown and described in FIGS. 11A and 11B. As shown for instance in FIG. 11A, the probe change unit 1102 includes a probe change unit housing 1200 sized and shaped to retain a motor 1202 such as a step motor therein. In the example shown, the motor 1202 is configured to provide one or more of clockwise and counter-clockwise rotation for instance to the probe change tool 1104. The probe change unit housing 1200 further includes a wiring interface 1204 extending through the probe change unit housing and electrically coupled with the motor 1202. Referring to FIG. 12A, a drive cap 1206 is shown engaged with the probe change tool 1104. As will be described in further detail below the drive cap 1206 in one example is a transmission means configured to provide rotational force to the probe change tool 1104 for corresponding rotation of the probe 702 positioned within the probe change tool 1104.

In another example shown in FIG. 12A, the probe change unit 1102 includes a mirror 1208 directed toward an access port 1212 extending through the probe change tool 1104. In one example the access port 1212 provides access (e.g. a direct visible line) to probe data 1214 provided on the probe 702. In another example, the probe data includes one or more of RFID, text, barcode and the like. For instance, the probe data 1214 includes one or more of probe identification data, calibration data such as the probe area function for the probe 702 and the like. Further, in the example shown in FIG. 12A the mirror 1208 is positioned by a mirror arm 1210 cantilevered relative to the probe change unit housing 1200. As shown in FIG. 12A the mirror arm 1210 is positioned to extend up and around the drive cap 1206 to substantially prevent the engagement of the mirror 1208 or the mirror arm 1210 with the drive cap 1206, for instance, during rotation of the drive cap during one or more of installation or decoupling of the probe 702 with the mechanical testing instrument 612. The mirror arm 1210 directs the mirror 1208 so that the mirror when viewed from above provides visibility to the probe data 1214 such as with the optical instrument 610 previously shown and described in FIGS. 6A and 6B. In another example, the mirror and mirror arm 1208, 1210 are replaced or are included in addition to other sensing instruments such as an RFID sensor, barcode reader, text reader and the like coupled with one or more of the optical instrument 610 or the probe change assembly 1100 previously shown and described in FIGS. 11A, B and 12A.

Referring now to FIG. 12B, as previously described the probe change unit 1102 is a part of the probe change assembly 1100 shown in FIGS. 11A and 11B. For instance, the probe change unit 1102 is configured to rotate or couple one or more probes 702 with the probe magazine 1108 and the mechanical testing instrument 612. Referring now to FIG. 12B, the probe change unit 1102 is shown in cross-section and includes the motor 1202 positioned within the probe change unit housing 1200 as previously described. A drive shaft 1216 extends from the motor into the drive cap 1206. As shown in FIG. 12B, the drive shaft 1216 is engaged with a spindle 1218 and the spindle is in turn rotatably coupled with the drive cap 1206.

As will be described in further detail below, in one example a rotary clutch or slip interface is provided between the spindle 1218 and the drive cap 1206 to ensure locking rotary engagement in one direction such as a decoupling direction with respect to the probe 702 and the mechanical testing instrument 612, and to permit slipping rotary engagement of the probe 702 and the mechanical testing instrument 612 for instance in a rotary installing direction.

Referring again to FIG. 12B, as shown in the cross-section the probe change unit 1102 further includes in one example a bearing 1220 interposed between portions of the drive cap 1206 and the spindle 1218. In one example the bearing 1220 is a rotational bearing including an inner bearing ring 1219 and an outer bearing ring 1221 with ball bearings interposed therebetween. As will be described in further detail below, the hearing 1220 facilitates the rotation of the spindle 1218 relative to the drive cap 1206 for instance where slipping engagement between the spindle and the drive cap is desired such as to avoid over-torquing of a probe 702 within the mechanical testing instrument 612. Instead, the bearing 1220 permits rotational force to be solely transmitted from the spindle 1218 to the drive cap 1206 through the rotary clutch described herein below.

In another example, the probe change unit 1202 includes a slipping interface feature 1222 coupled between one or more portions of the drive cap 1206 and the bearing 1220. In one example, the slipping interface feature 1222 includes a wave washer that selectively allows the transmission of torque between the drive cap 1206 and the hearing 1220. As further shown in FIG. 12B, a tool interface 1226 is provided between the drive cap 1206 and the probe change tool 1104. In one example the tool interface 1226 includes one or more of corresponding noncircular contours between the drive cap 1206 and the probe change tool 1104 or an interference fit therebetween. The noncircular interference fit at the tool interface 1226 ensures the reliable transmission of rotational forces from the drive cap 1206 to the probe change tool 1104 through rotation of the drive cap 1206. In another example, a probe interface 1224 is provided between the probe change tool 1104 and the probe 702 when the probe 702 is coupled with the probe change tool. For instance, as with the tool interface 1226, the probe interface 1224 includes a noncircular interface configured to ensure rotational movement of the probe change tool 1104 is transmitted to the probe 702 during installation and decoupling of the probe 702 from the mechanical testing instrument 612 or the probe magazine 1108.

Figure 13:
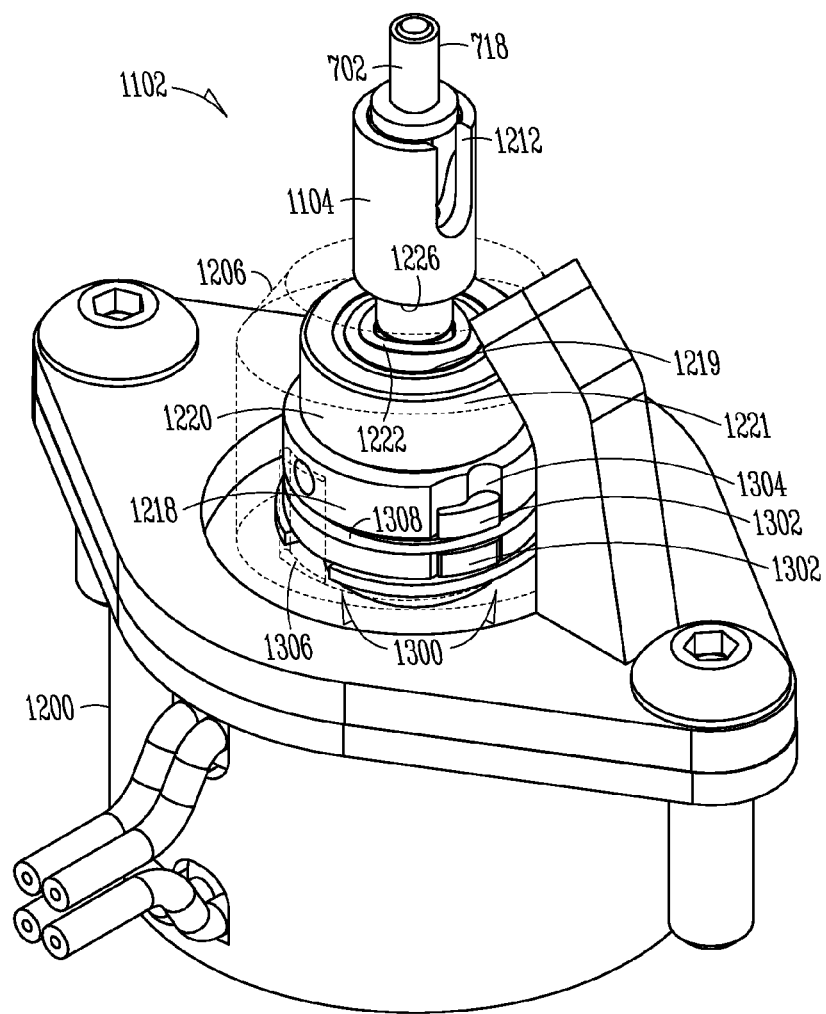
FIG. 13 is a perspective view of the tip change unit with a drive cap in broken lines to show one example of a rotary clutch in the tip change unit.

FIG. 13 shows the probe change unit 1102 with the drive cap 1206 provided in phantom lines. The drive cap 1206 is provided in phantom lines to expose the components of the rotary clutch 1300, for instance along the drive cap 1206 and the spindle 1218. The rotary clutch 1300 in one example includes one or more pawls 1302 moveably coupled with the spindle 1218. In another example, the rotary clutch 1300 further includes one or more pawl receivers 1306 positioned along the inner surface of the drive cap 1206. As will be described in further detail below, the rotary clutch 1300 provides slipping engagement in a first direction such as a probe installation rotation direction and provides locking non-slipping engagement between the spindle 1218 and the drive cap 1206 in a probe decoupling rotational direction.

Referring again to FIG. 13, the pawl 1302 is retained within a pawl housing 1304 formed in the spindle 1218. For instance, as shown in FIG. 13 the pawl housing 1304 has a substantially corresponding shape to the pawl 1302 to facilitate the reception of the pawl 1302 therein and to further facilitate the rotation of the spindle 1218 relative to the drive cap 1206 in the rotary installation direction and over at least a portion of the decoupling rotational direction at least until the pawl 1302 is received within the pawl receiver 1306. As further shown in FIG. 13, a biasing element 1308 is positioned around the spindle 1218. As will be described in further detail below, in one example the biasing element 1308 engages with a portion of the pawl 1302 (e.g. including one or more pawls 1302) to bias a portion of the pawl 1302 outwardly relative to the spindle 1218. Biasing of a portion of the pawl 1302 outwardly from the spindle 1218 biases that portion of the pawl into engagement with the pawl receiver 1306. In the decoupling rotational direction the biasing of the pawl 1302 outwardly biases the pawl into the pawl receiver 1306 and engages the pawl 1302 in a locking rotary engagement with the drive cap 1206 to substantially prevent the slipping of the spindle 1218 relative to the drive cap 1206 while the spindle 1218 is rotated in the decoupling direction.

Figure 14:
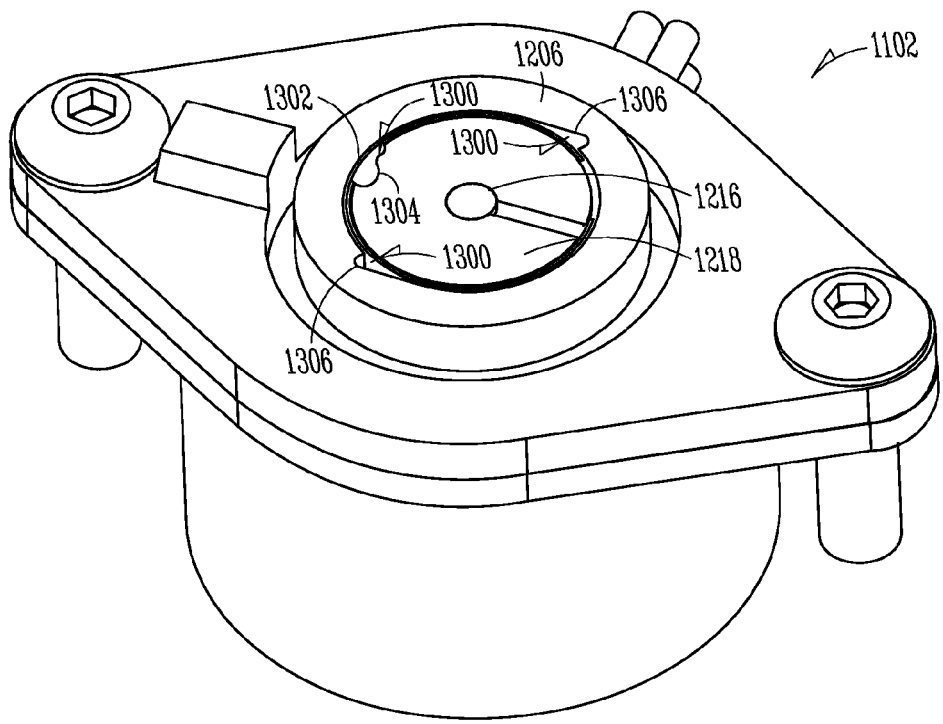
FIG. 14 is a cross sectional view of the tip change unit showing components of the rotary clutch shown in FIG. 13.

As shown in FIG. 14, the probe change unit 1102 is transversely cross-sectioned to expose the rotary clutch 1300 including the pawl 1302 positioned between the spindle 1218 and the drive cap 1206. In the configuration shown in FIG. 14, the pawl 1302 is substantially received within the pawl housing 1304 while the spindle 1218 is configured for selective slipping engagement with the drive cap 1206. For instance as the spindle 1218 is rotated in the counterclockwise (i.e., clockwise when viewed from the bottom up) direction for instance by rotation provided by the drive shaft 1216 coupled with the motor 1202 the pawl 1302 is biased outwardly into engagement with the inner surface of the drive cap 1206. While the spindle 1218 is moved in a counterclockwise direction the pawl 1302 as well as the other surfaces of the spindle 1218 engage with the inner surfaces of the drive cap 1206 to provide rotational movement to the drive cap 1206 and corresponding rotational movement to the probe change tool 1104 shown in FIGS. 11A and 11B. The probe 702 coupled with the probe change tool 1104 is thereby selectively rotated. In one example where the probe change tool 1104 is rotated in the counterclockwise direction for instance with a probe 702 coupled with a probe change tool 1104 torque is provided to the probe 702 until such time as the probe 702 is fully or at least partially received and coupled with the mechanical testing instrument 612. As the probe 702 is coupled with the mechanical testing instrument 612 a counter torque is provided between the interface features of the mechanical testing instrument 612 and the probe base 1718 of the probe 702. The counter torque is correspondingly transmitted to the drive cap 1208. Because the pawl 1302 is selectively engaged with the drive cap 1206 and not otherwise in locking engagement because of the counterclockwise rotation shown in FIG. 4 upon receiving the counter torque the drive cap 1206 will slide relative to the spindle 1218 to substantially prevent the over torquing of the probe 702 into the mechanical testing instrument 612. The transducer within the mechanical testing instrument 612 is thereby substantially preserved and not damaged by over-rotation of the probe 702 from the motor 1202.

In contrast, where decoupling of the probe 702 is desired from the mechanical testing instrument 612 the spindle 1218 is rotated in an opposed direction, such as the clockwise direction as shown in FIG. 14. While rotated in the clockwise direction (i.e., counterclockwise when viewed from the bottom up) the pawl 1302 continues to be biased outwardly for instance by the biasing element 1308. As the spindle 1218 rotates the counter torque of the probe 702 coupled with the mechanical testing instrument 612 is correspondingly transmitted through the probe change tool 1104 and the drive cap 1206. The counter torque allows the drive cap 1206 to slip relative to the spindle 1218 until the pawl 1302 reaches one or more of the pawl receivers 1306. Because the pawl 302 is biased outwardly the pawl 1302 is received in one or more of the pawl receivers 1306 and provides a locking rotary engagement between the drive cap 1206 and the spindle 1218. The motor 1202 is thereby able to provide a decoupling torque through the drive shaft 1216, the spindle 1218 and the drive cap 1206 to the probe change 1104. The torque transmitted to the probe 702 is able to readily decouple the probe 702 from the mechanical testing instrument 612. Because the probe 702 is being decoupled from the mechanical testing instrument 612 the locking engagement between the spindle 1218 and the drive cap 1206 does not damage the transducer as the probe 702 instead rotates relative to the transducer and decouples from the mechanical testing instrument 612.

As described, the rotary clutch 1300 is thereby able to provide locking rotary engagement between the probe change tool 1104 and spindle 1218 in a probe decoupling rotation direction and selected slipping engagement between the probe change tool 1104 and the spindle 1218 in a probe installing rotational direction. For instance, through the selective engagement of one or more pawls 1302 with the interior surface of the drive cap 1206 selected slipping engagement and transmission of torque between the spindle 1218 and the drive cap 1206 is realized. In contrast, locking rotary engagement between one or more pawls 1302 and one or more pawl receivers 1306 provides locking rotary engagement without slipping between the spindle 1218 and the drive cap 1206 to ensure reliable decoupling of the probe 702 for instance from the mechanical testing instrument 612 (or the probe magazine 1108).

Figure 15:
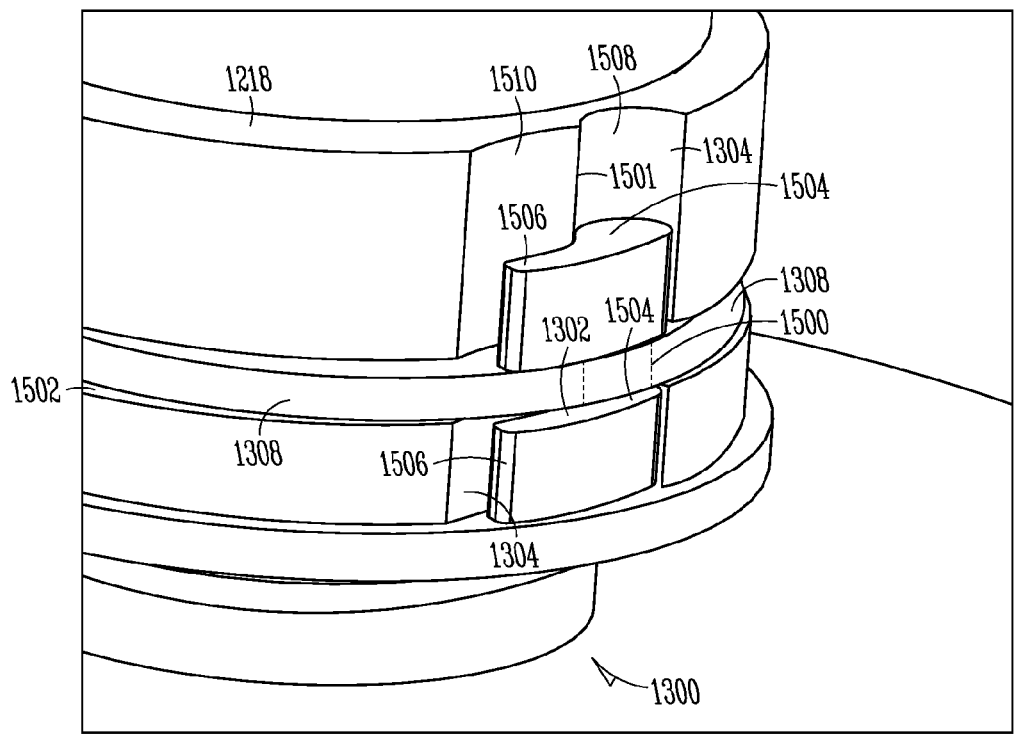
FIG. 15 is a detailed perspective view of one example of the pawl of the rotary clutch.

FIG. 15 shows a detailed perspective view of the spindle 1218 of the probe change unit 1102 previously described and shown in FIG. 11A. As shown, the drive cap 1206 is removed to further expose the pawls 1302 and the pawl housing 1304. As shown in FIG. 15, a plurality of pawls 1302 are provided with an interposing pawl boss 1500 extending therebetween. In one example, the pawl boss 1500 extends across a biasing element groove 1502. As previously described the probe change unit 1102 includes a biasing element 1308 extending around the spindle 1218. As shown in FIG. 15, the biasing element 1308 is received within the biasing element groove 1502 and overlies the pawl boss 1500. The biasing element 1308 includes in one example an elastomeric band sized and shaped to provide an inwardly projecting biasing force against the pawl boss 1500. In another example, the biasing element 1308 includes, but is not limited to a spring wire, an elastic element and the like sized and shaped to provide an inward biasing force. The engagement of the biasing element 1308 with the pawl boss 1500 biases heads 1504 of the pawls 1302 inwardly into the relatively larger head grooves 1508. Inward movement of the heads 1504 (e.g., into snug reception within the head grooves 1508) biases (e.g., rotates) the tails 1506 of each of the pawls 1302 outwardly through engagement of the pawls with a pivot point 1501. The tails 1506 are thereby biased into engagement with the spindle 1218 (e.g. along the inner spindle surface or within one of the pawl receivers 1306).

As shown in FIG. 15, the pawls 1302 further include heads 1504 received in the larger head grooves 1508 formed as part of the pawl housings 1304 formed in the spindle 1218. In another example, tail groves 1510 are further provided within the pawl housing 1304 to receive the tails 1506 there. As previously described, the pawl housing 1304 allows for the reception of the pawls 1302 therein while the spindle 1218 rotates with the drive cap 1206 for instance in a selective slipping engagement between the drive cap 1206 and the spindle 1218 in a probe installing rotational direction. In contrast, the biasing element 1308 biases at least the tails 1506 outwardly from the spindle 1218 (e.g., through inward biasing of the pawl boss 1500 and the heads 1504 for pivoting at the pivot point 1501) for reception of the tails 1506 within the pawl receivers 1306 where the spindle 1218 is rotated in a probe decoupling rotational direction to ensure the pawls 1302 provide a locking engagement between the spindle 1218 and the drive cap 2106 as described above.

Reading of Probe Identification or Calibration Data from the Probe

Figure 16:
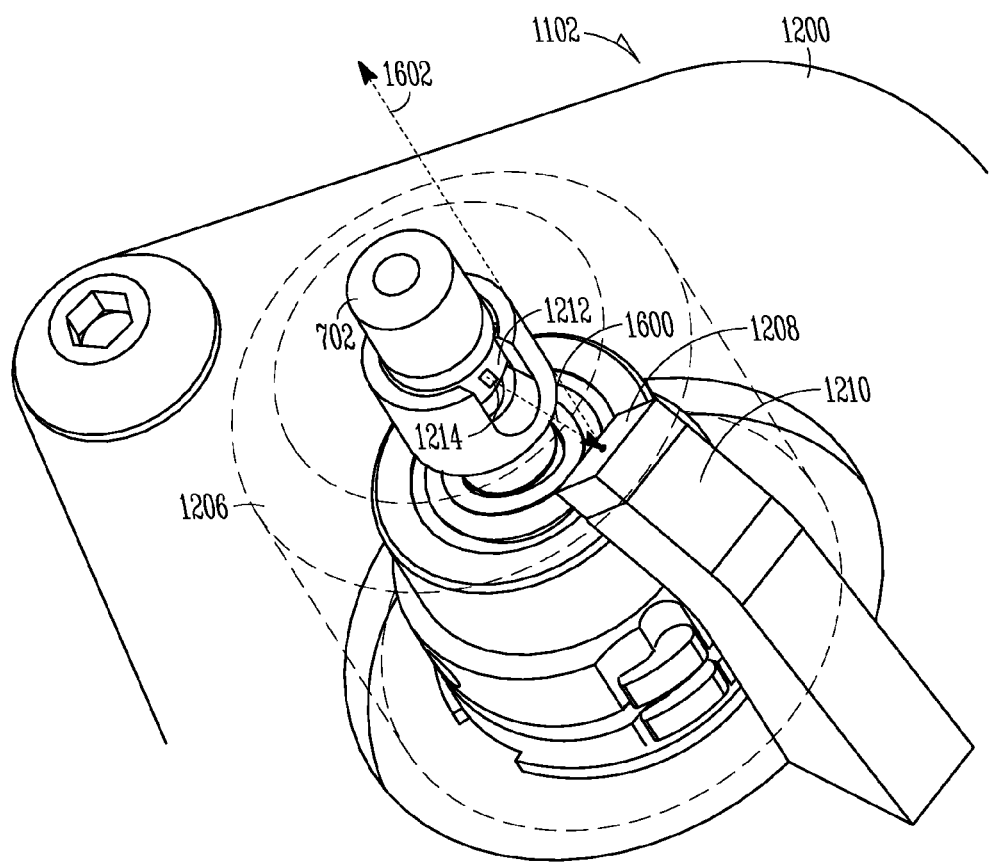
FIG. 16 is a perspective view of the tip change unit shown in FIG. 12A including a mirror coupled with a mirror arm to facilitate viewing of one or more of identification or calibration data of an instrument tip coupled with the tip change unit.

FIG. 16 shows one example of the probe change unit 1102 with the mirror 1208 directed toward the access port 1212 and probe data 1214 provided on a probe 702. As previously described, in one example the mirror 1208 is one means for providing access to the probe data 1214 by the automated testing system 600 for instance through the optical instrument 610. As shown in FIG. 16, an image line 1600 extends from the probe data 1214 to the mirror 1208. A reflected image line 1602 for instance with the inverse of the probe data 1214 shown at FIG. 16 extends upwardly such as toward the optical instrument 610 where the optical instrument 610 is aligned with the mirror 1208.

As previously described, in another example the stage receptacles 628 are indexed for ready positioning by the stage actuator assembly 618. In yet another example, the mirror 1208 is also indexed for the stage actuator assembly 618 (e.g., relative to the stage receptacle 628). The stage actuator assembly 618 is thereby controlled to position the sample stage 614 including one or more of the mirrors 1208 for one or more of the probe change units 1102 into alignment with the optical instrument 610. By aligning the mirror 1208 with the optical instrument 610 the optical instrument 610 is able to observe the probe data 114 supplied along with probe 702 visible through the access port 1212. In another example, the optical instrument 610, another instrument such as an RFID reader, barcode reader and the like is oriented at other angles for instance perpendicular to the probe 702 and directed toward probe data 1214 positioned at other locations on the probe 702 to eliminate the need for the mirror 1208. For instance, the optical instrument 610 or RFID reader, barcode reader or the like is positioned perpendicularly relative to the probe 702 to provide direct access to the probe data 1214. In another example with an RFID reader, alignment of the RFID reader with the mirror 1208 is not necessary. Instead, the RFID reader is brought into close proximity with the probe 702 to activate the RFID chip and thereby read the information therefrom.

Figure 17:
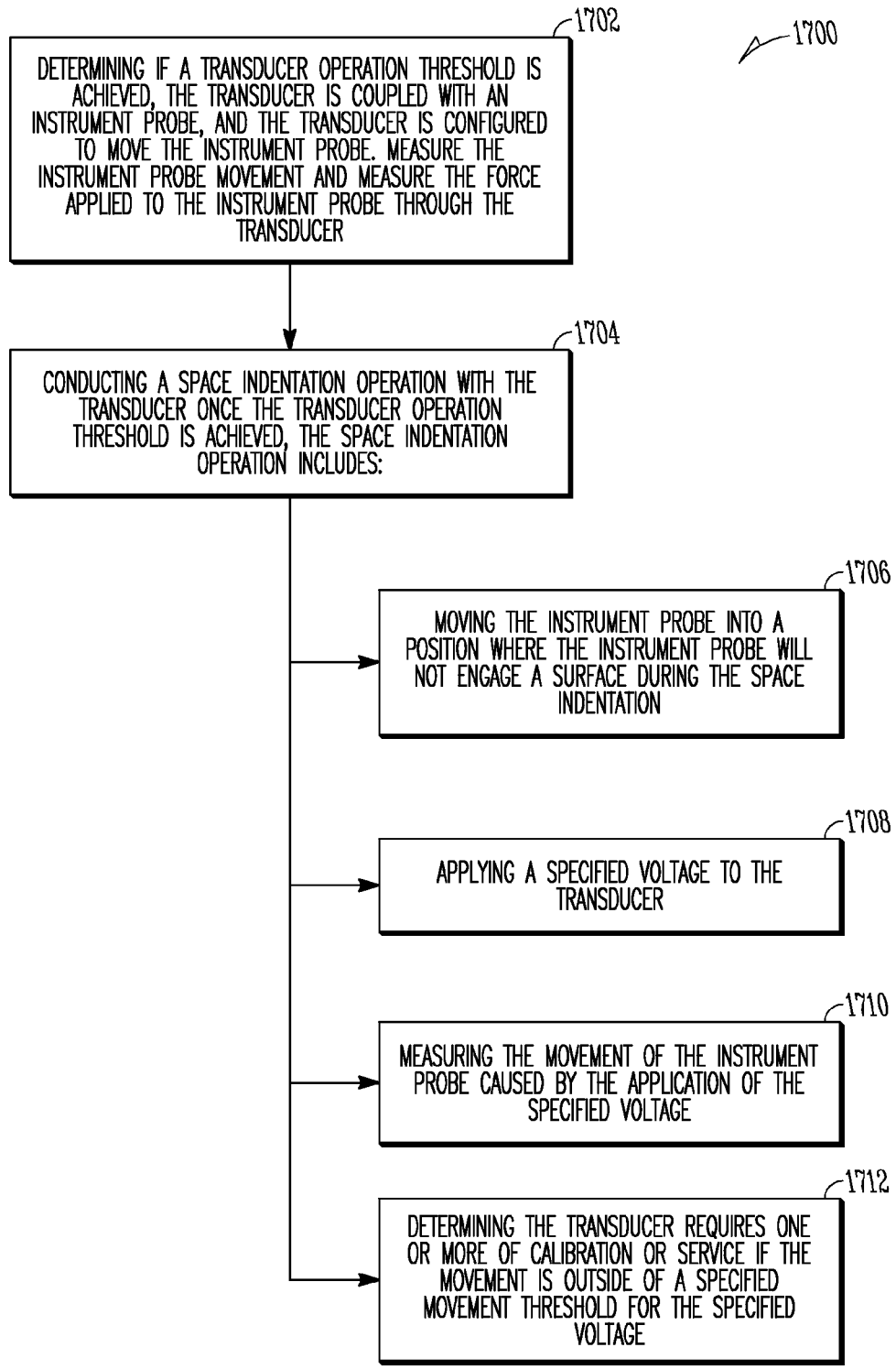
FIG. 17 is a block diagram showing one example of an automatic method for performing a space indentation diagnostic of a transducer of a mechanical testing instrument.

Method for Automatically Examining a Transducer Response to the Mechanical Testing Instrument FIG. 17 shows one example the method 1700 for automatically examining a transducer response in the mechanical testing instrument configured to perform mechanical testing at micron scale or less (e.g., equal to or less than microns). In describing the method 1700 reference is made to previously described features and functions provided herein. Where reference numerals are provided the numerals are intended to be exemplary and not limiting. For instance, the recited structure and features in the method 1700 as well as the other methods described herein include the referenced features, other similar features described herein as well as their equivalents. At 1702, the method 1700 includes determining if a transducer operation threshold is achieved. The transducer 700 includes in one example the transducer assembly 700 shown in FIG. 7A and the corresponding capacitor assembly 1710 shown in FIG. 7C. In one example, the transducer assembly is coupled with an instrument probe such as the probe 702 shown in FIG. 7C. The transducer, such as the capacitor assembly 710, is configured to move the probe 702, measure the instrument probe movement and measure the force applied to the instrument probe 702 through for instance the movement of a center plate 712 relative to the oppose plates 714 of the capacitor assembly 710.

At 1704, a space indentation operation is conducted with the transducer such as the transducer assembly 700 once the transducer operation threshold is achieved. In one example, the space indentation operation includes at 1706 moving the instrument probe 702 into a position where an instrument probe 702 will not engage a surface during the space indentation. For instance, the instrument stage 608 is operated to move the mechanical testing instrument 612 relative to the sample stage 614 to elevate the mechanical testing instrument out of possible engagement with the sample stage surface 616. In another example, the stage actuator assembly 618 is operated to move the sample stage surface 616 laterally relative to the mechanical testing instrument 612 to substantially move the sample stage surface 616 out alignment with the mechanical testing instrument.

At 1708, a specified voltage is applied to the transducer, for instance, across the opposed plates 714. As previously described herein, the application of the specified voltage to the opposed plate 704 generates an electrostatic force between the opposed plates 714 and the center plate 712 thereby deflecting or moving the center plate 712 relative to the opposed plates 714. At 1710, the movement of the instrument probe 702 (e.g., the center plate 712) is measured. At 1712, it is determined whether the transducer assembly 700 requires one or more of calibration or service if the measured movement is outside of the specified movement threshold for the specified voltage. For instance, the specified voltage is paired with a predicted movement of the probe 702 (e.g., the center plate 712 of the capacitor assembly 710) and where the measured movement of the probe 702 is outside the specified or predicted threshold range of the movement for the probe 702 one or more of calibration or service is indicated for performance on the transducer assembly 700.

Several options for the method 1700 follow. In one example, determining if the transducer operation threshold is achieved includes counting the number of transducer operations (e.g., indents, scratches and the like) and then determining if the number of transducer operations are greater than the transducer operation count threshold. In one example, the transducer operation count threshold corresponds to empirically developed threshold numbers generated in part on experience as well as knowledge of the mechanical characteristics of the sample and probe under consideration. For instance, in one example, the transducer operation count threshold is one or more of 100 indentations, 1000 indentations or the like. As described above, the transducer operation count threshold, for instance, one or more of the numbers provided is adjusted up or down depending on the material being tested, the material of the probe, the forces being applied, the indentation depth, scratch, length and the like. In another example, determining if the transducer operation threshold is achieved includes adjusting the transducer operation count threshold according to the specified accuracy range. For instance, where measurements of mechanical parameters of the sample are desired within a predicted range of accuracy where measurements of the mechanical parameter are outside of said specified range, the transducer operation count threshold or the transducer operation threshold are considered achieved and the space indentation operation is conducted again.

In still another example, determining if the transducer operation threshold is achieved includes determining that the transducer operation threshold is achieved if the transducer measures a force outside of a normal operating force range. For instance, in one example, the transducer assembly 700 is configured to provide forces to the probe 702 on the order of milli-newtons. Where forces incident on the capacitor assembly 710 fall outside of the this range, for instance, 1 or more newtons is applied to the transducer 702 (e.g., corresponding to or approximately a pound or more) the transducer operation threshold is met indicating a possible strike of the probe 702 by the user or a piece of machinery and requiring the space indentation operation be performed to ensure capacitor assembly 710 has not been damaged by the unintentional interaction with the probe 702 and the center plate 712 by an operator. With each of the threshold determination steps and functions described herein, the control station 110 or other similar control system includes, but is not limited to, a comparator, processor, circuit and the like configured to compare the relevant measure value (e.g., parameter, count and the like) against the respective threshold and thereby make a determination that the threshold is met.

Figure 18:
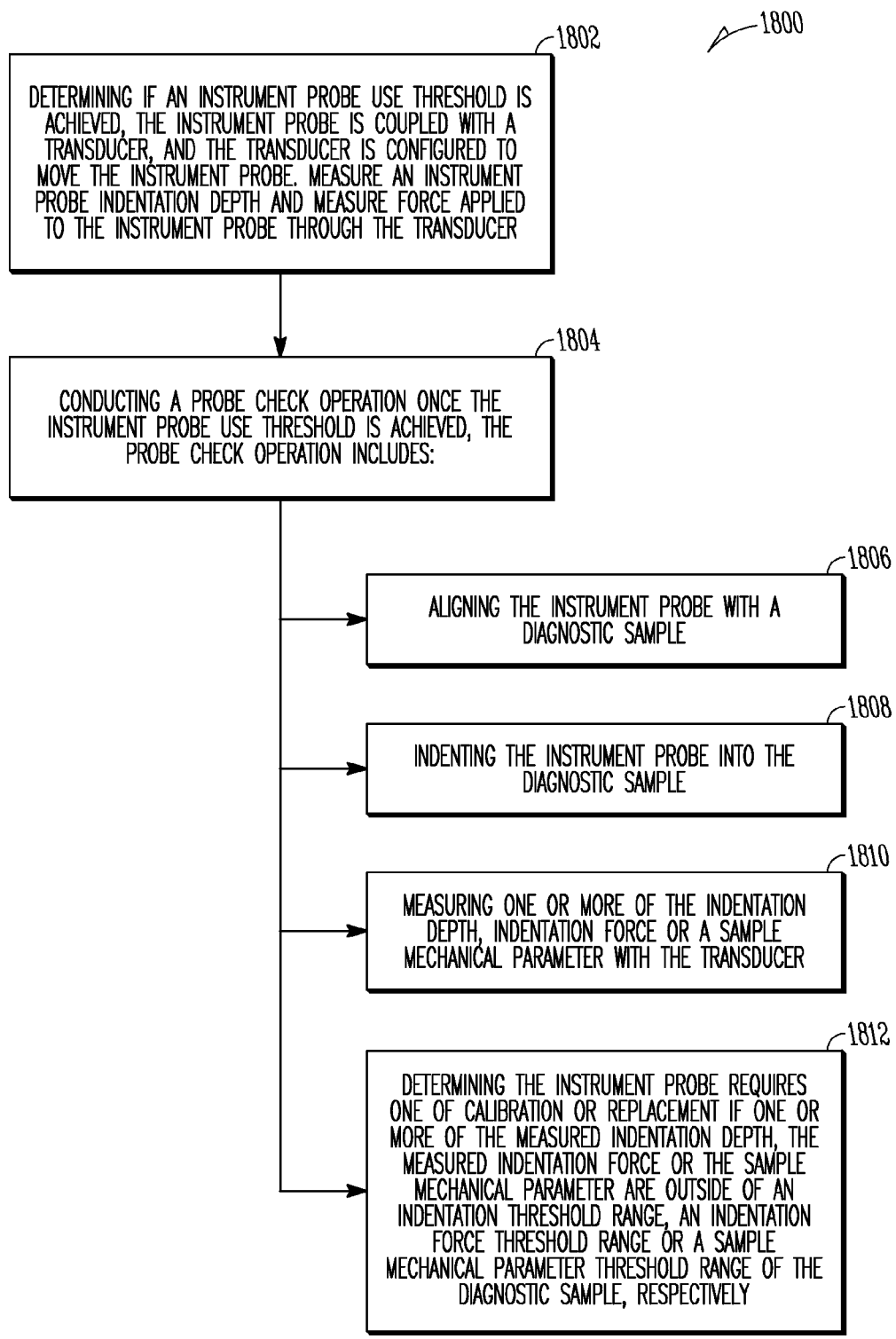
FIG. 18 is a block diagram showing one example of an automatic method for performing a tip diagnostic of an instrument tip of a mechanical testing instrument.

Examination of a Probe of a Mechanical Testing Instrument for Use for an Automated Testing System FIG. 18 shows one example of the method 1800 for automatically examining an instrument probe 702 coupled with a mechanical testing instrument, such as the testing instrument 612 shown in FIGS. 6A and 6B. In one example, the mechanical testing instrument 612 is configured to perform mechanical testing at micron scale or less (e.g., at the nanoscale). As described with the method 1700, in the description of the method 1800 reference is made to features and elements previously described herein including reference numerals for the same. Reference numerals are intended to be exemplary and not limiting. For instance, features and elements described in the method 1800 include the referenced elements, other similar features and their equivalents. At 1802, the method 1800 includes determining if an instrument probe use threshold is achieved. Instrument probe 702 is coupled with the transducer such as the capacitor assembly 712 shown in FIG. 7C. The transducer assembly 700 is configured to move the instrument probe 702, measure an instrument probe indentation depth and measure the force applied to the instrument probe through the transducer 700. At 1804, a probe check operation is conducted once the instrument probe use threshold is achieved.

In one example, the probe check operation includes but is not limited to at 1806 aligning the instrument probe 702 with a diagnostic sample such as one or more of the diagnostic samples 1106 shown in FIG. 11A. At 1808, the instrument probe 702 is indented into the diagnostic sample 1106. At 1810, one or more of the indentation depth, indentation force or a sample mechanical parameter is measured with the transducer 700.

At 1812, the method 1800 includes determining the instrument probe 702 requires one or more of calibration or replacement if one or more of the measured indentation depth, measured indentation force or the sample mechanical parameter measured are outside of an indentation threshold range, an indentation force threshold range or a sample mechanical parameter threshold range of the diagnostic sample, respectively. For instance, the automated testing system, an operator or the like specifies one or more of the threshold ranges described herein. Where the measured indentation depth, indentation force or a sample mechanical parameter measured with the transducer are outside of this threshold range one or more of calibration or replacement of the probe 702 is indicated.

Several options for the method 1800 follow. In one example, determining if the instrument probe use threshold is achieved includes counting the number of transducer operations such as for the transducer 700. The method 1800 further includes determining if the number of transducer operations are greater than the transducer operation count threshold. In a similar manner to the method 1700, the transducer operation count threshold is in one example determined according to the materials tested, the probe material, the forces applied, the indentation depth are the same and the like. In one example, the empirical or experienced base criteria are used by the operator to adjust the transducer operation count threshold upward or downward according to the desired reliability for the automated testing system. As described in one example, the transducer operation count threshold includes 10, 100, 1000 or more transducer operations before a probe check operation as described herein is required.

In another example, determining if the transducer operation count threshold is achieved includes adjusting the transducer operation count threshold according to one or more of the material tested, the instrument probe, and the force applied to the probe through the transducer. In still another example, determining if the transducer operation count threshold is achieved includes adjusting the transducer operation count threshold upward or downward according to the specified accuracy range. For instance, where the measured mechanical parameters for the sample are desired to be within a specified range, measured values of the parameter that fall outside of a range trigger performance of the probe check operation as described herein.

In another example, determining if the instrument probe use threshold is achieved includes measuring one or more of the instrument probe indentation depth, force applied to the instrument probe through the transducer or a sample mechanical parameter of the sample and then determining the instrument probe use threshold is met if one or more of the instrument probe indentation depth force applied to the instrument or the sample mechanical parameter is outside of one or more of the specified indentation depth threshold range, a specified force threshold range, or a specified sample mechanical parameter threshold range of the sample (in contrast to the diagnostic sample 1106). For instance, a probe check operation may be triggered where one or more of the indentation depth, indentation force, or a measured sample mechanical parameter are outside of one or more threshold ranges. For instance, if the transducer operation count threshold is not met, however one or more of the indentation force, the indentation depth or the measured sample mechanical parameter are outside of the predicted threshold range for a particular sample the probe check operation is conducted even though the transducer operation count threshold is still not met.

In one example, aligning the instrument probe, for instance, the probe 702 coupled with mechanical testing instrument 610 with a diagnostic sample 1106 includes moving the diagnostic sample 1106 beneath the instrument probe 702. For instance, moving the diagnostic sample 1106 beneath the instrument probe includes one or more of translating and rotating a sample stage surface 616 (e.g., the sample stage) wherein the sample stage surface includes a stage receptacle flange 630 housing one or more diagnostic samples 1106. In one example, moving the diagnostic sample 1106 includes translating the sample stage surface 616 along an X axis and a Y-axis. In one example, the X axis translation range is greater than the Y axis translation range available with stage actuator assembly 618 such as the X-stage and Y-stage 620, 622. In still another example, moving the diagnostic sample includes rotating the sample stage 614 around a Z axis, for instance with the rotational stage 624, as shown in FIG. 6A. In yet another example, moving the diagnostic sample 1106 beneath the instrument probe (e.g., into alignment with the instrument probe 702) includes a combination of translating and rotating the sample stage 614 from a first sample location where the instrument probe 702 is aligned with the first sample location (e.g., on the sample stage surface as opposed to the flange 630) to a second diagnostic location where the instrument probe 702 is aligned with the diagnostic sample 1106, such as on the stage receptacle flange 630. With each of the threshold determination steps and functions described herein, the control station 110 or other similar control system includes, but is not limited to, a comparator, processor, circuit and the like configured to compare the relevant measure value (e.g., parameter, count and the like) against the respective threshold and thereby make a determination that the threshold is met.

Method of Probe Calibration

Figure 19:
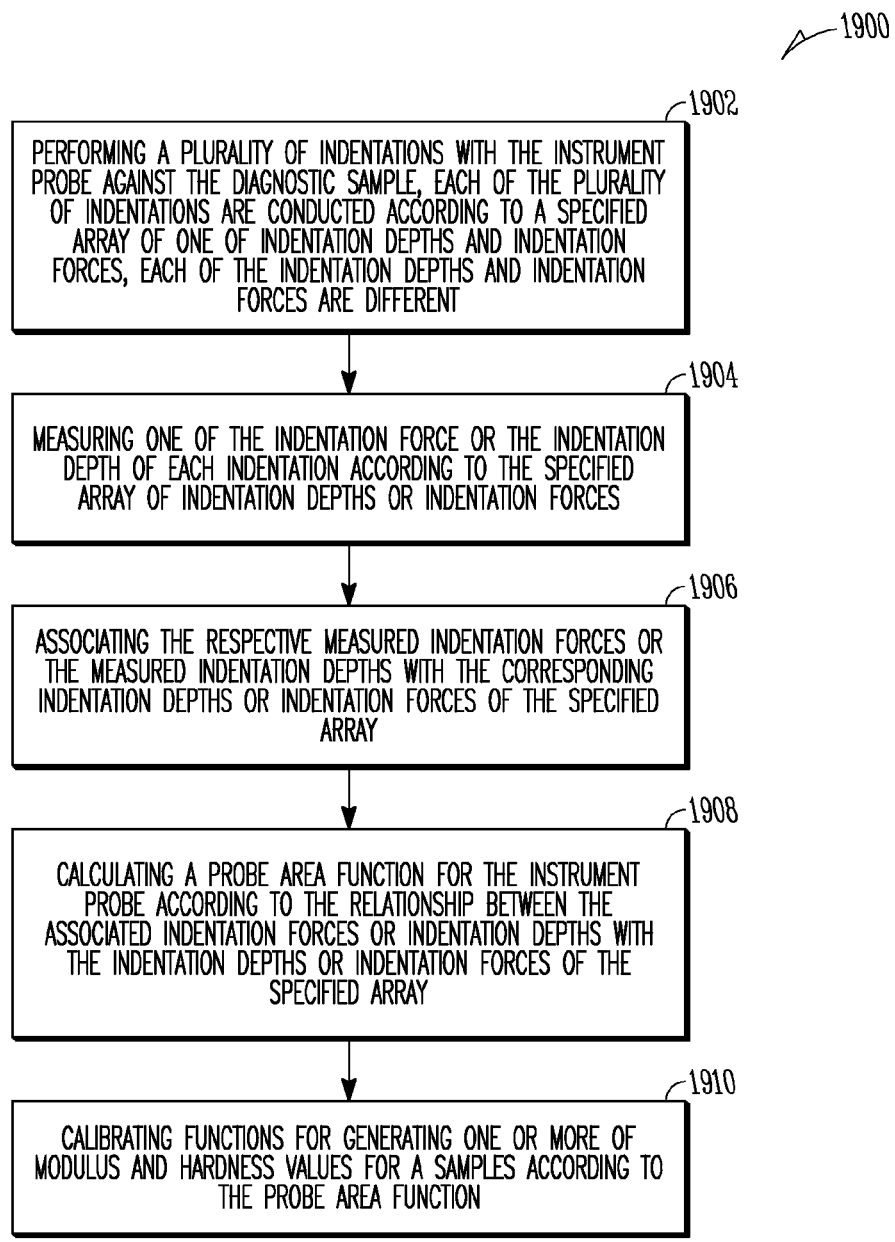
FIG. 19 is a block diagram showing one example of an automatic method for performing a tip calibration of an instrument tip of a mechanical testing instrument.

In still another example, the probe calibration is conducted if one or more of the measured indentation depth, the measured indentation force or the sample mechanical parameter measured are outside of the indentation threshold range, the indentation force threshold range or the sample mechanical parameter threshold range, respectively. In one example, the probe calibration method includes the method 1900 shown in FIG. 19. At 1902, a plurality of indentations are performed with the instrument probe 702 against the diagnostic sample 1106. Each of the plurality of indentations are conducted according to a specified array (e.g., predicted values) of one of indentation depths or indentation forces, each of the indentation depths, indentation forces being different. At 1904, one or more of the indentation force or the indentation depth of each indentation according to the specified array of indentation depths or indentation forces are measured. At 1906, the respective measured indentation forces or the measured indentation depths are associated with the corresponding predicted indentation depths or indentation forces of the specified array.

At 1908, a probe area function is calculated for the instrument probe 702 according to the relationship between the indentation forces or indentation depths associated with the indentation depths or indentation forces of the specified array. Stated another way, the measured indentation forces or measured indentation depths that are associated with the corresponding predicted indentation depths or indentation forces in the specified array are utilized to generate a probe area function for the probe 702 (e.g., for instance to provide a recalibration function for use with the used probe 702 to ensure the used probe provides accurate and reliable results when used in the automated testing system 600).

In one example in 1910, functions used within the control station 110 are configured to operate the automated testing assembly 100. The control functions of the automated testing system 600 are in one example calibrated with the probe area function 702 for the probe 702 generated, for instance, with the method 1900, to ensure accurate determination of one or more of modulus and hardness values for a sample based on measured values obtained with the mechanical testing instrument 610. For instance, with a new probe 702 or a used probe 702 the method 1900 shown in FIG. 19 may be performed to provide a calibrating function corresponding to the probe area function for the software and control system to ensure the reliable and accurate measurements of hardness and modulus of samples under consideration.

In yet another example, the probe check operation 1800 is conducted again after the calculation of the probe area function of the instrument. The method 1800 includes determining the instrument probe 702 requires replacement if one or more of the measured indentation depth measured indentation force or the sample mechanical parameter are still outside the corresponding indentation threshold range, the indentation force threshold range, or the sample mechanical parameter threshold range of the diagnostic sample 1106. That is to say, after conducting the probe calibration operation to generate a probe area function, the probe check operation described and shown in the method 1800 is conducted again. If the measured values with the probe 702 tested against the diagnostic sample 1106 are outside the threshold ranges, the probe 702 is, in one example, considered unusable and thereafter specified for replacement and the probe 702 is not used until replacement with an installation method described herein.

Method for Installing an Instrument Probe

Figure 20:
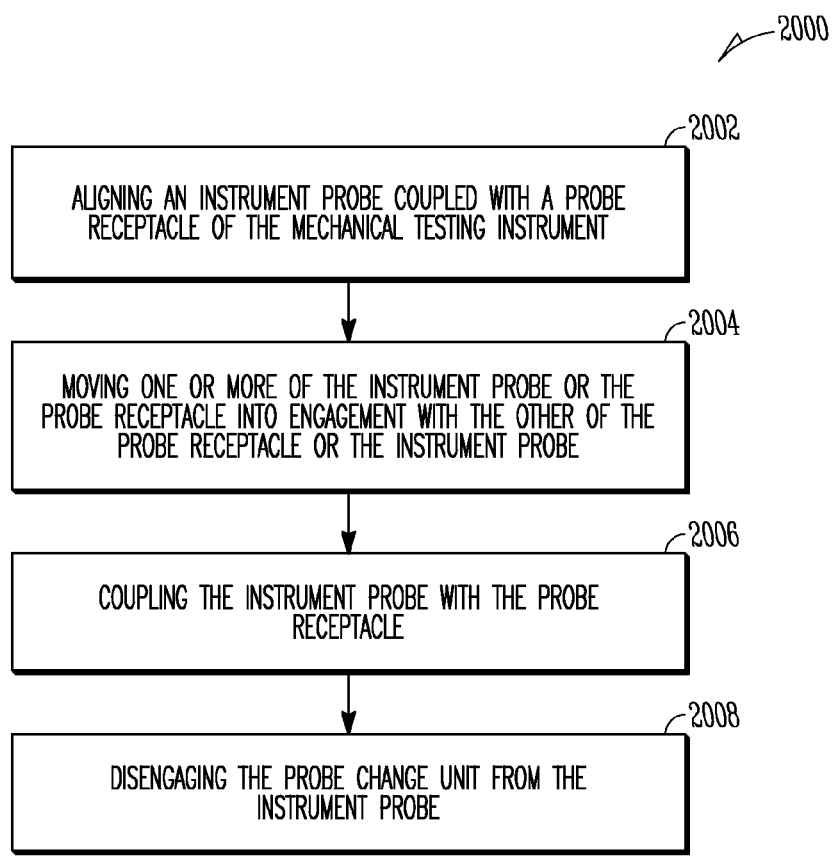
FIG. 20 is a block diagram showing one example of an automatic method for installing an instrument tip in a mechanical testing instrument.

FIG. 20 shows one example of a method 2000 for installing an instrument probe, such as the instrument probe 702, in the transducer such as the transducer assembly 700 previously shown in FIGS. 7A and 7B. In one example, the probe 702 is coupled with a mechanical testing instrument 610 configured for performing mechanical testing at a micron scale or less, for instance, at one or more microns to nanoscale. As with the previously described methods, the method 2000 includes references to features and elements previously described herein as well as reference numerals for the same. Reference numerals are intended to be exemplary and are not limiting. For instance, a feature or element provided with a reference numeral includes the recited elements as well as all similar elements and their equivalents. At 2002, the method 2000 includes aligning an instrument probe 702 coupled with a probe change unit 1102 with a probe receptacle 722 of the mechanical testing instrument 610. At 2004, one or more of the instrument probe 702 or the probe receptacle 722 is moved into engagement with the other of the probe receptacle or the instrument probe. For instance, one or more of the instrument probe 702 or the probe receptacle 722 are moved along a z axis into engagement with the other of the probe receptacle or the instrument probe. At 2006, the instrument probe 702 is coupled with the probe receptacle 722, for instance, by relative rotation coupling of mechanical coupling features and the like. At 2008, the probe change unit 1102 is disengaged from the instrument probe 702 leaving the probe 702 coupled with the mechanical testing instrument 612.

Several options for the method 2000 follow. In one example, aligning the instrument probe 702 with the probe receptacle 722 includes one or more of X axis and Y axis translating of the probe change unit 1102. In another example, aligning the instrument probe 702 with the probe receptacle 722 includes rotating the probe change unit 1102 around the Z axis, for instance, the Z axis coincident with the center axis of the probe change unit 1102 and a probe change tool 1104 coupled with the probe change unit 1102. In still another example, aligning the instrument probe 702 with the probe receptacle 722 includes actuating a multiple degree of freedom stage 614 configured to translate in the X and Y axes and rotate around a Z axis (e.g., the center of rotation of the stage 614). The multiple degree of freedom stage 614 includes a sample stage surface 616, a stage receptacle flange 630 coupled with the sample surface 616 and one or more stage receptacles 628. The stage receptacle flange 630 and each of the one more stage receptacles 628 are sized and shaped to house the probe change units 1102. In another example, the stage receptacle flange 630 including the one or more stage receptacles 628 is sized and shaped to couple with a plurality of probe change units 1102. Optionally, moving one or more of the instrument probes 702 or the probe receptacle 722 into engagement with the other of the probe receptacle or the instrument probe includes translating the probe receptacle along a Z axis with an instrument stage coupled with the mechanical testing instrument such as the instrument stage 608. In another example, the sample stage 614 includes a Z actuator configured to elevate the sample stage as well as the probe change unit 1102 relative to the mechanical testing instrument 612.

In other examples, the method 2000 includes other features and steps for the coupling of the instrument probe 702 with the mechanical testing instrument 612. In one example, coupling the instrument probe 702 with the probe receptacle 722 includes rotating the instrument probe 702 with the probe change unit 1102. For instance, the probe 702 includes a probe base 718 having one or more mechanical interface features such as threading configured to couple with the corresponding features of the probe receptacle 722, such as a probe coupling feature 720 (see FIG. 7C). In another example, rotating the instrument probe 702 with the probe change unit 1102 includes rotating the probe changing tool 1104 in a probe installing rotational direction. The probe changing tool 1104 is coupled with a spindle 1218 with a rotary clutch 1300 providing a selective slipping engagement between the probe changing tool 1104 and the spindle 1218.

In still another example, coupling the probe 702 with the probe receptacle 722 includes initially rotating the probe 702 with the probe changing instrument 1102 in a probe decoupling rotational direction and measuring the force incident on a transducer 700 of the mechanical testing instrument 612. Rotation of the probe 702 in the probe decoupling rotational direction is arrested where the measured forced incident on the transducer 700 decreases below a thread interface force threshold. For instance, the instrument probe 702 is rotated in the probe decoupling rotational direction (e.g., counter to the threads) and as the threads of the probe 702 ride over the corresponding threads of one or more of the probe receptacle 722 or the probe coupling feature 720 the threads on one of the probe receptacle and the probe coupling feature move upward thereby correspondingly deflecting the center plate 712 and creating a measurable deflection of the center plate 712 relative to the opposed plates 704. Once an end of the threads on the probe 702 passes over an end of the threads on the probe receptacle 722 or the probe coupling feature 720 (e.g., an apex of the threads), the probe threads disengage and the center plate 712 moves downward, for instance, the threads on the probe 702 fall into a gap between threads on the problem receptacle 722 or the probe coupling feature 720. The downward deflection of the center plate satisfies the thread interface force threshold (a threshold corresponding to a measured decrease in force) thereby alerting the system that the probe threads have moved downward and are now reliably positioned between threads of the probe receptacle. With the threads of the probe 702 interfaced between threads of one or more of the probe receptacle 722 or the probe coupling feature 720 the risk of cross threading is minimized and the rotation of the probe in the decoupling rotational direction is thereafter arrested.

With the threads interfaced the instrument probe 702 rotates with the probe change unit 1102 in a probe installing rotational direction to couple the probe 702 with the probe receptacle 722 and thereby coupling the probe 702 with the mechanical testing instrument 612. In still another example, coupling the instrument probe 702 with the probe receptacle 722 includes counting steps of a step motor such as the motor 1202 shown in FIGS. 12A and 12B and arresting the operation of the step motor when a step count threshold is achieved, for instance, corresponding to a number of turns of the probe 702 empirically considered to properly couple the probe 702 with the mechanical testing instrument 612.

In another example, the method 2000 includes checking coupling of the instrument probe 702 with the probe receptacle 722. In one example, the checking of the coupling between the instrument probe and the probe receptacle includes measuring the force on a transducer such as the transducer assembly 700 of the mechanical testing instrument 612 after coupling of the instrument probe 702 with the mechanical testing instrument. The instrument probe 702 is considered coupled with the probe receptacle if the transducer measures a force corresponding with an instrument probe weight, for instance, where the transducer is deflected according to a specified weight of the probe 702 after disengagement of the probe change unit 1102 from the probe 702. The measurement of the instrument probe weight provides a measure of confidence that the probe 702 is properly coupled with the probe receptacle 722.

In another example, the method 2000 includes mounting the instrument probe 702 and the probe changing unit 1102 of the probe change assembly 1100 previously shown in FIGS. 11A and 11B. For instance, in one example, mounting the instrument probe 702 in the probe changing unit 1102 includes aligning the probe change unit 1102 with the instrument probe 702 in a probe magazine 1108. The probe change unit 1102 is moved into engagement with the instrument probe. For instance, in one example, the probe magazine 1108 includes a z actuator or is coupled with the instrument stage 608 of the cantilevered instrument column 606 to depress the instrument probe 702 into engagement with the probe change unit 1102, for instance, the probe change tool 1104. In still another example, a z actuator is provided with a stage actuator assembly 618 to elevate the sample stage 614 and thereby engage the probe change tool 1104 of the probe change unit 1102 with the instrument probe 702 provided in the probe magazine 1108.

In another example, the method 2000 includes decoupling a previously installed probe 702 from the probe receptacle 722 before coupling of the instrument probe 702 with the probe receptacle. Stated another way, in one example, an existing or used probe coupled with mechanical testing instrument 612 is decoupled from the mechanical testing instrument 612 by the probe changing unit 1102 of the probe change assembly 1100 prior to installation of the new probe in the mechanical testing instrument 612. In one example, decoupling the previously installed probe on the probe receptacle 722 includes aligning the probe change unit 1102 with the previously installed probe 702. Decoupling the previously installed probe 702 further includes coupling the previously installed probe 702 with the probe change unit 1102. The previously installed probe 702 is thereafter decoupled from the probe receptacle of the mechanical testing instrument 612 with the probe change unit 1102. In one example, the previously installed probe is loaded within a probe magazine after decoupling from the probe receptacle 722 of the mechanical testing instrument 612.

In still another example, decoupling of the previously installed probe 702 from the probe receptacle 722 includes rotating the previously installed probe with the probe change unit 1102. For instance, rotation of the previously installed probe with the probe change unit 1102 includes rotating a probe changing tool 1104 in a probe decoupling rotational direction. Probe changing tool 1104 is coupled with a spindle 1218 with a rotary clutch 1300 providing a locking rotary engagement between the probe changing tool and the spindle.

In another example, the method 2000 includes reading one or more of identification data 1214 or calibration data 1214 from the instrument probe 702. For instance, in one example, a mirror such as the mirror 1208 is aligned with an optical instrument 610. The mirror 1208 is directed toward one or more identification or calibration data 1214 on the instrument probe, for instance, viewable through an access port 1214 in the probe change tool 1104. The method further includes reading one or more of the identification or calibration data 1214 by way of the reflection of the mirror 1208 toward the optical instrument 610. In another example, the method 2000 includes one or more of calibrating or controlling the mechanical testing instrument 612, or the control or measurement functions for instance in the control station 110 (that operate the mechanical testing instrument 612) according to the read calibration data from the probe 702.

Minimal Footprint and Cantilevered Arm of the Automated Testing System

Figure 21A:
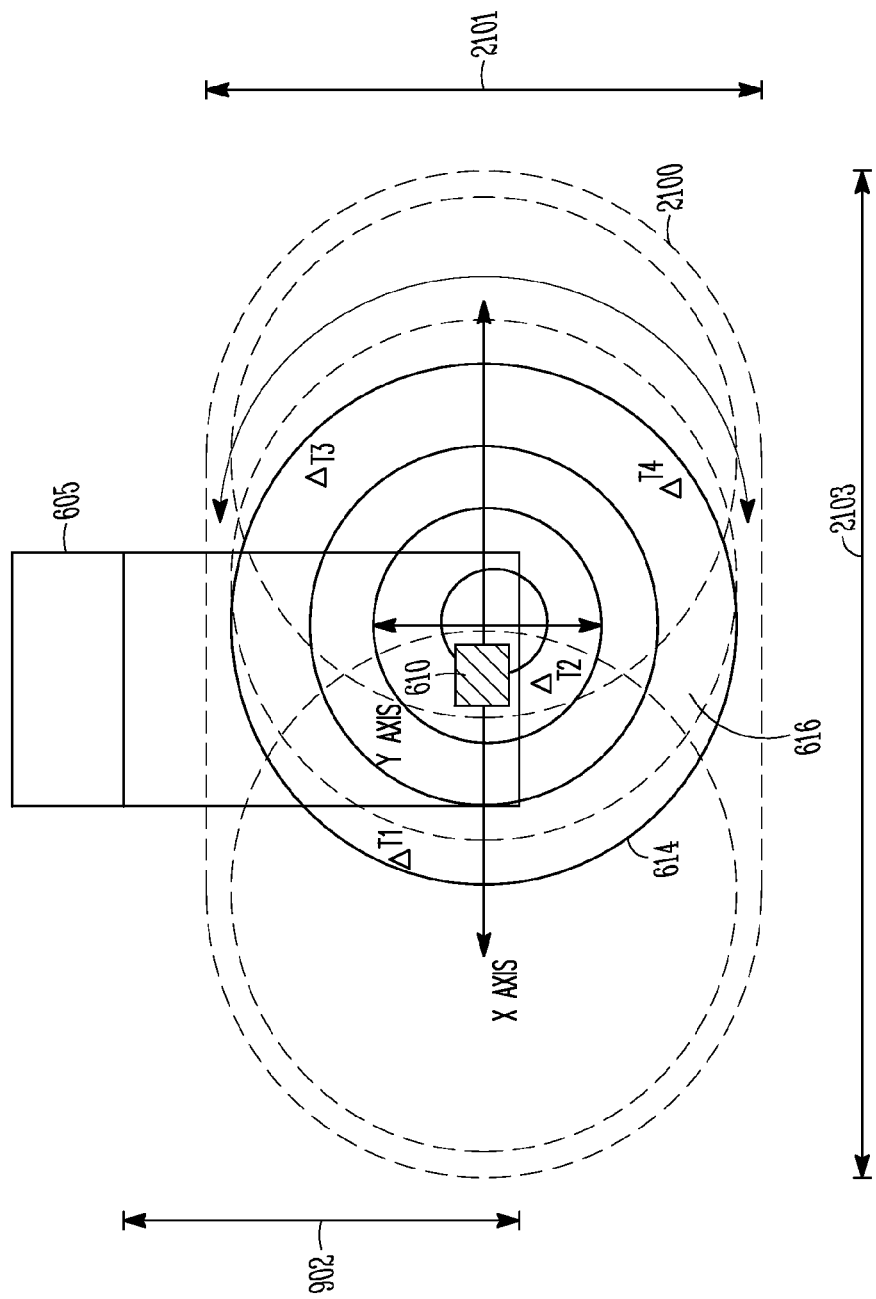
FIG. 21A is a schematic view of one example of a sample stage of the automated testing system positioned with translational and rotational stages.

FIG. 21A shows the overall foot print of the sample stage 614 coupled with the stage actuator assembly 618, shown in FIGS. 6A and 9, having X, Y and rotational stages 620, 622, 624. As shown, four test locations T1-4 are provided on opposing peripheral edges and near the center of the sample stage surface 616. The outline of the sample stage 614 is shown that corresponds to the position of the stage where each of the T1-4 are selectively positioned beneath the mechanical testing instrument 612. As shown, with a combination of X translation and rotation of the sample stage 614 each of the test locations T1-4 are readily positioned within a first footprint 2100 (e.g., a sample stage footprint). In one example, the first foot print 2100 has a first dimension 2101 substantially similar to a sample stage length 900 (see FIG. 9) where the sample stage 614 is not movable or is minimally movable (e.g., for misalignment between the instruments 610, 612) along the y-axis. That is to say, the first dimension 2101 is optionally slightly larger than the sample stage length 900. Optionally, the y-axis is substantially parallel to the cantilevered arm 607 of the cantilevered instrument column 606. In another example, the first foot print 2100 has a second dimension 2103 substantially similar to a range of translation of the sample stage 614 along the x-axis (e.g., an axis optionally orthogonal to the cantilevered arm 607). Stated another way, with the combination of X translation and rotation (e.g., through the stages 620 and 624) the first footprint 2100 is minimized (e.g., with reduced or no Y translation). The automated testing system 600 footprint includes the first footprint 2100 and the column footprint, for instance the perimeter of the column base 605.

As further shown in FIG. 21, the cantilevered instrument column length 902 is minimized according to the limited (optionally non-existent) translation of the sample stage 614 along the Y-axis because of the addition of the rotational stage 624 to provide enhanced positioning flexibility to the stage 614. Deflection of the cantilevered instrument column, noise and the like, for instance with a larger cantilever, are thereby minimized to ensure reliable and accurate testing with the mechanical testing instrument 610.

Figure 21B:
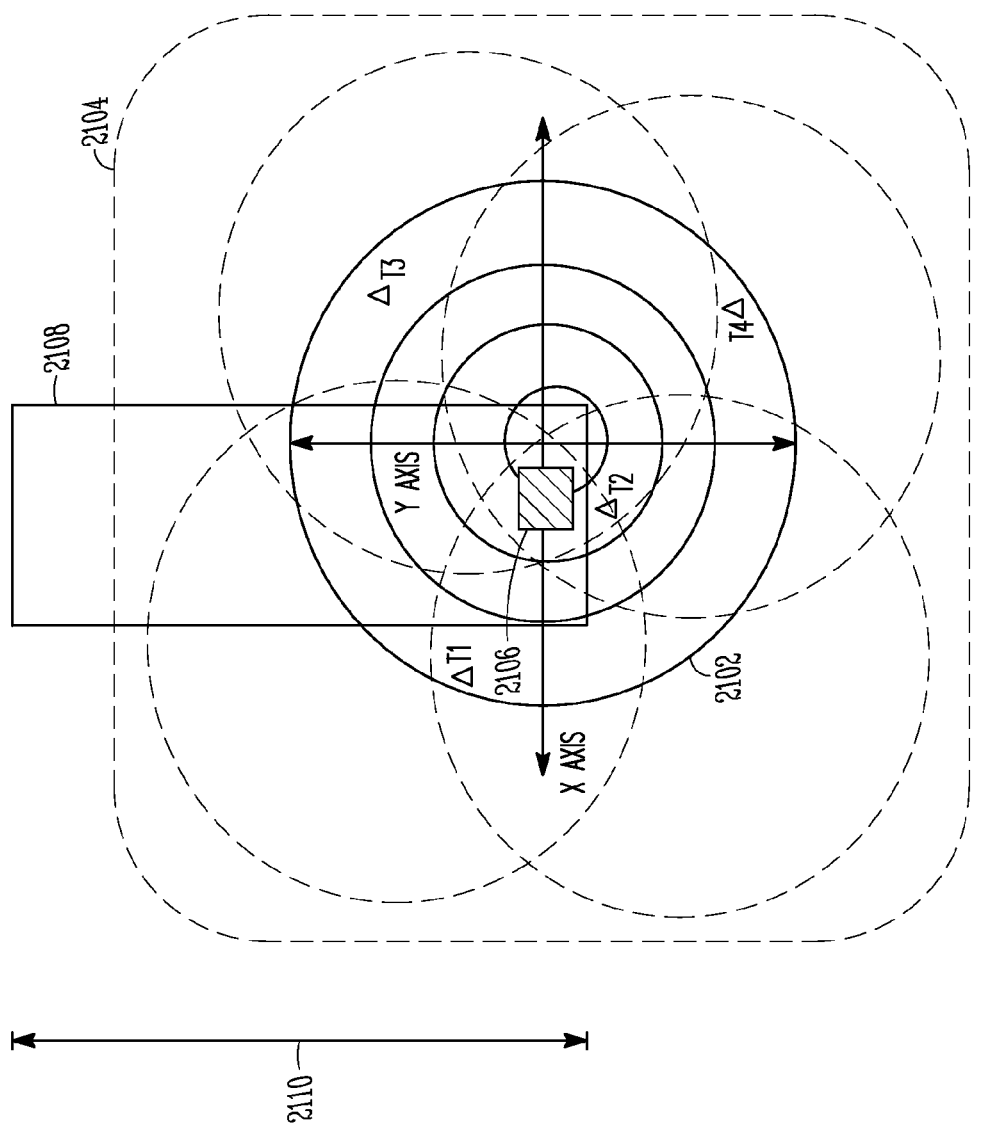
FIG. 21B is a schematic view of another example of a sample stage of the automated testing system positioned with translational stages.

In contrast, FIG. 21B shows the overall footprint 2104 of a sample stage 2102 including lateral stages. Relative to the footprint 2100 of the sample stage 614 (including rotational as well as translational stages), the foot print 2104 is larger. The overall footprint of a testing system including the sample stage 2102 is thereby larger to ensure all locations of a sample on the stage may be tested with a mechanical testing instrument 2106. A larger footprint and system correspondingly assume greater space on a factory floor and may require additional labor and reworking of an existing production line to make room for such a system. Alternatively, the sample stage 2102 includes stages having limited translation ranges that correspondingly limit the locations the mechanical testing instrument 2106 may test on a sample coupled on the sample stage 2102.

Additionally, the footprint 2104 of the sample stage 2102 requires that the cantilevered instrument arm 2108 has a correspondingly longer cantilevered instrument column length 2110 relative to the cantilevered instrument column length 902 of the instrument column 606 (shown in FIG. 21A and FIG. 9). The increased cantilevered instrument column length 2110 increases the susceptibility of the mechanical testing instrument 2106 to deflection and noise. Alternatively, the cantilevered instrument arm 2108 is made larger to better structurally support the mechanical testing instrument 2106. Increasing the size of the arm 2108 increases the footprint 2104 of the system and the system correspondingly assumes more room on a factory floor.

Figure 22A:
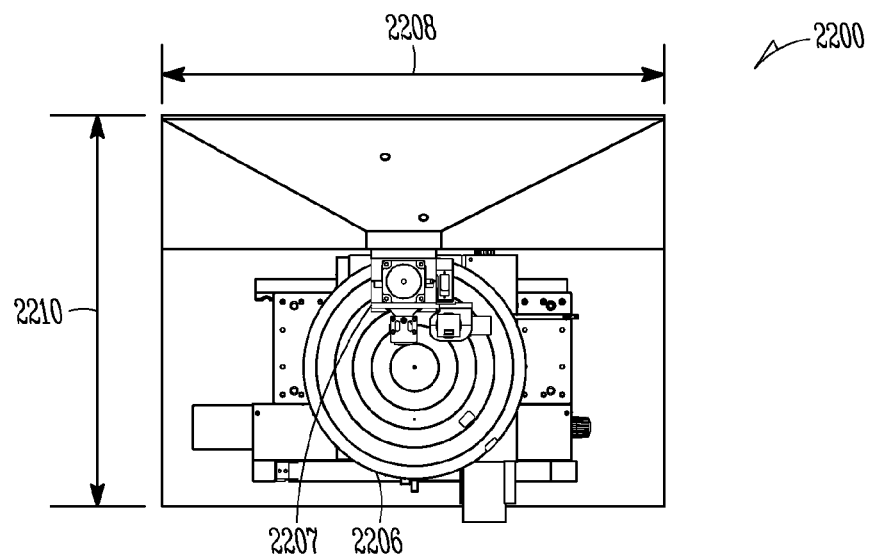
FIG. 22A is a plan view of one example of a testing system including translational stages and limited instrument coverage of a sample stage.
Figure 22B:
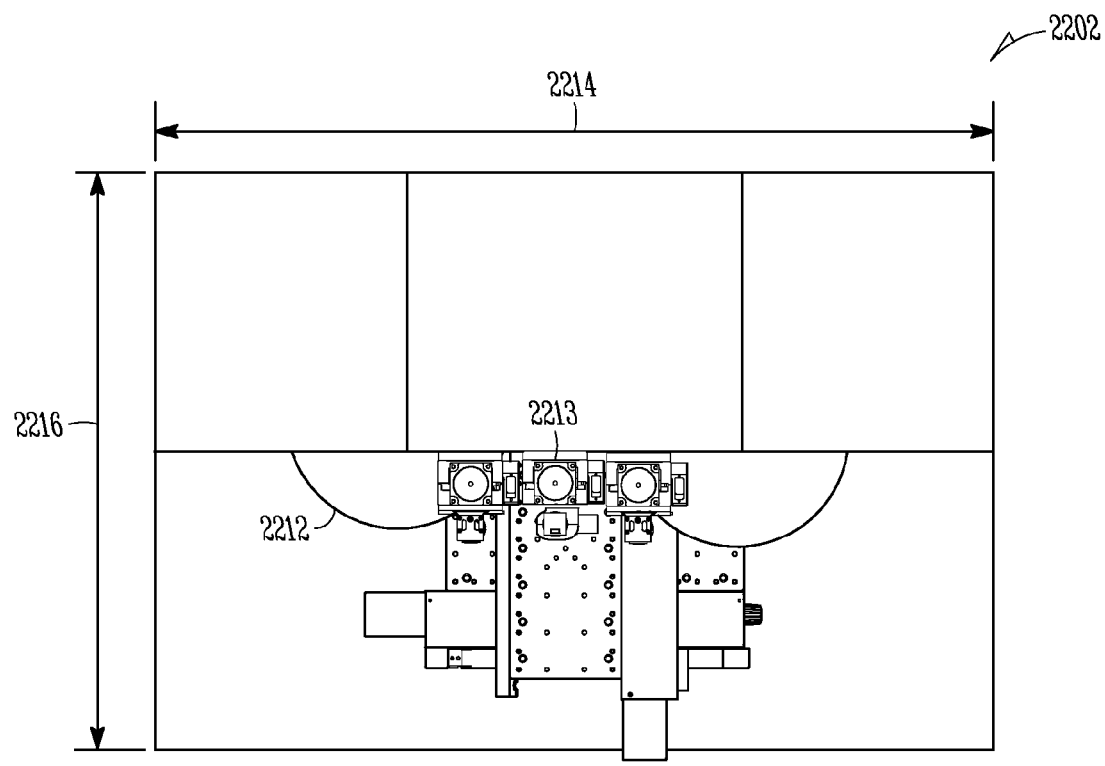
FIG. 22B is a plan view of another example of a testing system including translational stages and an enhanced overall system footprint.
Figure 22C:
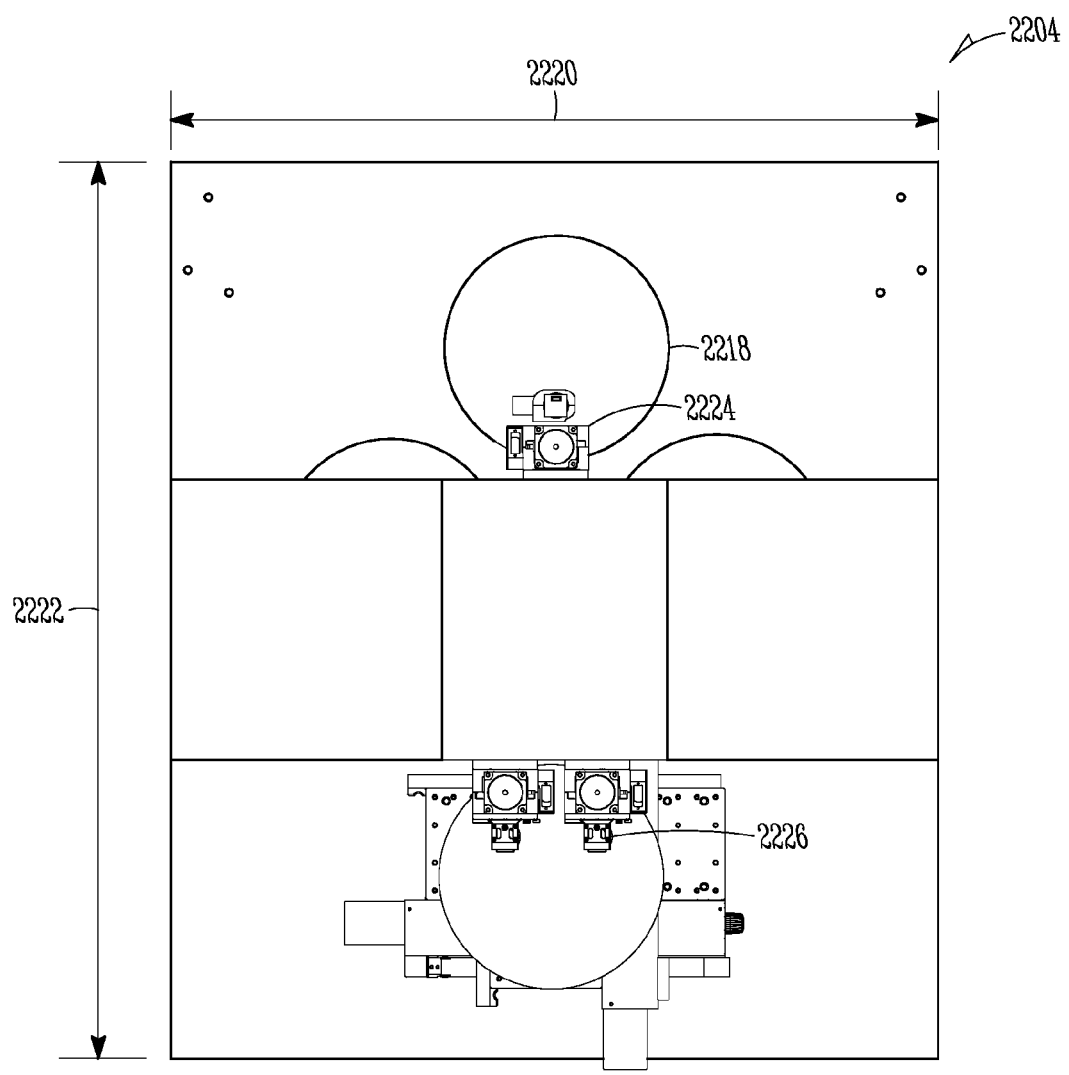
FIG. 22C is a plan view of yet another example of a testing system including translational stages and an enhanced overall system footprint.

FIGS. 22A-C show three separate examples of systems 2200, 2202, 2204 including stages configured to move through X and Y translation. Referring to FIG. 22A, the system 2200 including the sample stage 2206 includes X and Y stages configured to move the sample stage 2206 so that at least one third of a sample positioned across the sample stage 2206 is accessible by a mechanical testing instrument such as the mechanical testing instrument 2207 shown in FIG. 22A. As shown, the sample stage 2206 perimeter closely corresponds to a sample perimeter, such as a semiconductor wafer having a diameter of approximately 300 millimeters. The footprint for the system 2200 is shown approximately by the X dimension 2208 and the Y dimension 2210. In one example, the X dimension 2208 measures approximately 27 inches while the Y dimension measures approximately 21 inches.

Referring now to FIG. 22B, another example of a system 2202 is shown. As shown in FIG. 22B, the system 2202 includes an expanded footprint configured to allow positioning of the sample stage 2212 relative to the mechanical testing instrument 2213 at substantially any location on the sample stage 2212 corresponding to a sample such as a semiconductor wafer having a diameter of 300 millimeters. In this example, with the expanded footprint the X dimension 2214 and the Y dimension 2216 of the system 2202 are larger than those of the system 2200 to account for the additional space needed to ensure full positioning of all locations on the sample stage 2212 in alignment with the mechanical testing instrument 2213. As shown in the example, the X dimension 2214 is approximately 45 inches while the Y dimension 2216 is approximately 31 inches. Each of the X and Y dimensions 2214, 2216 is correspondingly larger than the X and Y dimensions 2208, 2210 of the system 2200 shown in FIG. 22A. The width of the granite base prescribes the length of the bridge (e.g., the underlying rectangle and the overlying rectangular object adjacent to the mechanical testing instrument 2213) to an extreme that the bridge must be thick and robust (e.g., with a substantial arch and support legs) to have sufficiently high natural frequencies and stiffness for accurate testing while still allowing for positioning of all sample locations in alignment with the mechanical testing instrument.

Another example of a testing system 2204 is shown in FIG. 22C. As with the previous examples, the sample stage 2218 is configured for movement according to X and Y translation to position one or more testing locations of the sample stage 2218 in alignment with both of the mechanical testing instruments 2224, 2226. In this arrangement, to ensure the sample stage 2218, for instance a sample such as a semiconductor wafer having a diameter of 300 millimeters positioned thereon, is positionable relative to the mechanical testing instruments 2224, 2226 to ensure all locations on the sample are available for testing by the mechanical testing instruments the footprint of the system 2204 is larger than either of the footprints for the systems 2200, 2202 previously described. For instance, the system 2204 has an X dimension 2220 measuring approximately 41 inches and a Y dimension 2222 measuring approximately 48 inches. The overall footprint of the system 2204 is thereby larger than the overall footprints of the systems 2200, 2202. As with the system 2202, the width of the granite base prescribes the length of the bridge (e.g., the underlying rectangle and the overlying rectangular object adjacent to the mechanical testing instrument 2213) of the system 2204 to an extreme that it must be thick and robust to have sufficiently high natural frequencies and stiffness to allow for accurate testing while at the same time allowing for instrument access to substantially all locations on the sample.

Figure 23:
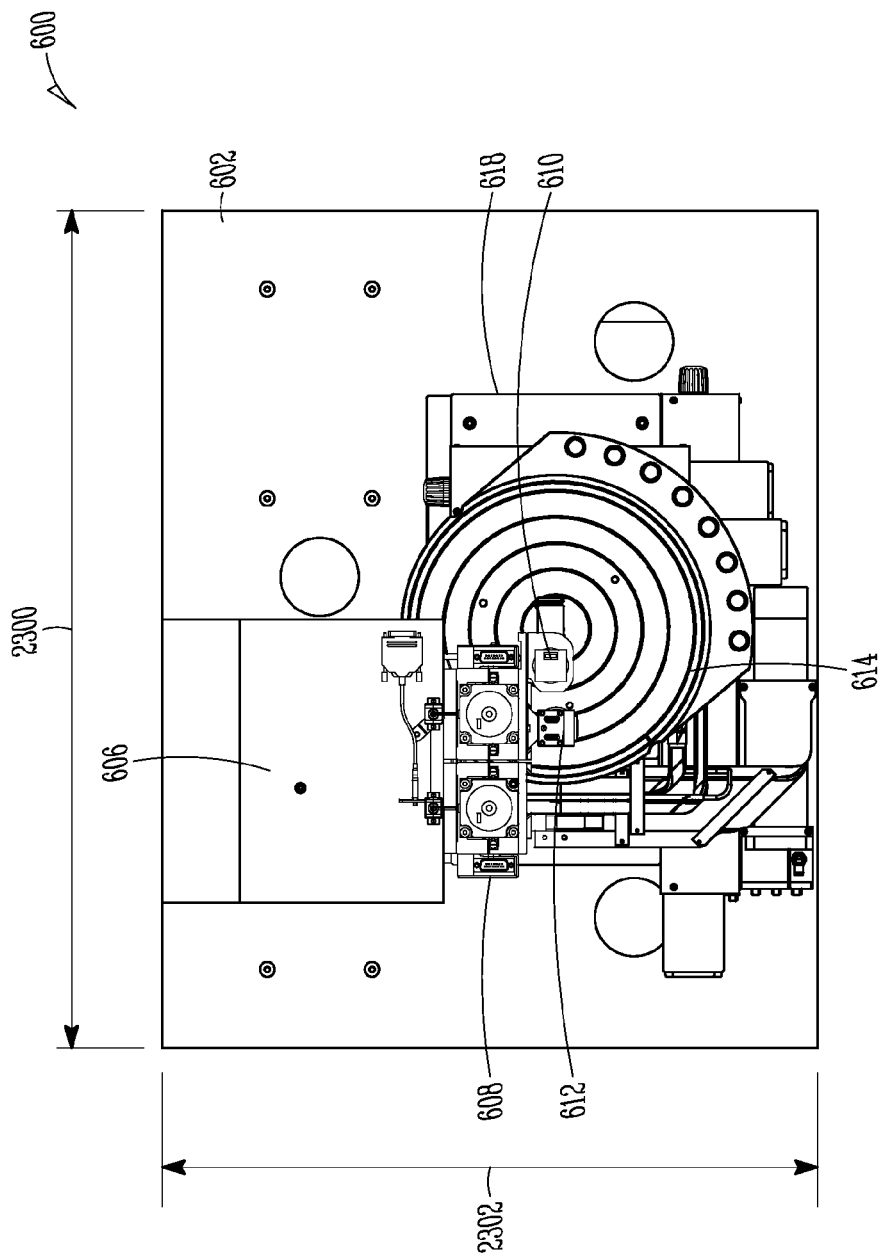
FIG. 23 is a plan view of the testing system shown in FIG. 6A including translational and rotational stages and a minimized footprint and minimal cantilevered instrument column length.

Referring now to FIG. 23, the automated testing system 600 previously described herein, for instance as shown in FIGS. 6A and 9, is shown in a top down view. As shown, the automated testing system 600 includes a granite base 602 and a cantilevered instrument column 606 extending over the sample stage 614. As shown, the cantilevered instrument column 606 extends over a portion of the sample stage 614. As previously described, the stage actuator assembly 618 combines translational and rotational actuation of the sample stage 614 to position substantially any location on the sample stage 614 beneath the optical and mechanical testing instruments 610, 612. As previously described and shown in FIG. 23, the rotational and translational stage actuator assembly 618 minimizes the overall footprint of the automated testing system 600. For instance as shown in FIG. 23, the sample stage 614 is fully accessible by the mechanical and optical testing instruments 612, 610. Stated another way, substantially all locations on the sample stage surface 616 are capable of alignment with the instruments 610, 612. The sample stage 614 is fully accessible by the instruments while presenting a minimal footprint relative to any of the systems 2202, 2204 previously shown in FIGS. 22A-C. As shown in FIG. 23, in one example the automated testing system 600 has a footprint at least partially defined by an X dimension 2300 and a Y dimension 2302. In one example, the X dimension 2300 measures approximately 32 inches and the Y dimension measures approximately 25 inches. As shown, the automated testing system 600 with the stage actuator assembly 618 as described herein thereby has a smaller footprint than either of the testing systems 2202, 2204 shown in FIGS. 22B and 22C. The overall footprint of the automated testing system 600 shown in FIG. 23 is slightly larger than the test system 2200 shown in FIG. 22A. However, the automated testing system 600 shown in FIG. 23 provides full access to substantially all locations (including diagnostic samples, probe change units and the like as previously described herein) on the sample stage 614 with the mechanical and optical testing instruments 612, 610. In contrast, the system 2200 while having a smaller footprint is only able to allow access to approximately one-third of the overall surface area of the stage 2206. The automated testing system 600 including the sample stage 614 and the stage actuator assembly 618 thereby presents a smaller overall footprint than many other testing systems, while at the same time providing full access to substantially all locations of the sample stage 614 including, for instance, large samples such as semiconductor wafers having a diameter of 300 millimeters positioned on the sample stage 614.

Additionally, as previously described, the provision of the stage actuator assembly 618 having combined translational and rotational capabilities minimizes the overall cantilevered length of the instrument column 606 to thereby to provide a supported and stiff assembly for positioning and operation of the mechanical testing instrument 612. Deflection and noise incident on the mechanical testing instrument 612 are minimized according to the minimal cantilevered length of the cantilevered instrument column 606. For example, the range of X stage 620 translation only needs to be long enough to reach half of the wafer (e.g., 150 mm) plus the distance between the farthest optics and indentation positions. The range of Y stage 622 translation only needs to be long enough to cover Y-axis misalignment between the optical instrument 610 and the mechanical testing instrument 612 due to design and assembly variation (e.g., about 5, 10 or 20 mm and the like). Stated another way, the range of Y stage 622 translation, the maximum a northernmost edge of the stage can move up and the maximum a southernmost edge of the stage can move down along the y axis, is coextensive with the first dimension 2101 of the first footprint 2100 (e.g., the sample stage footprint). Similarly, the range of X stage 620 translation, the maximum an easternmost edge of the stage can move to the right and the maximum a westernmost edge of the stage can move to the left along the x axis, is coextensive with the second dimension 2103 of the first footprint 2100. The range of X stage 620 translation is, in this example, greater than the range Y stage 622 translation.

Because the X stage 620 is able to translate the sample stage 614 from a location where the instruments 610, 612 are aligned near the stage center (e.g., near a sample center) to a location where the instruments are aligned with the edge of the stage (e.g., near an edge of the sample), rotation of the rotational stage 624 (e.g., the theta stage) provides access and full coverage of the instruments to all portions of the sample not otherwise available with X stage 620 translation. The rotational stage 624 in combination with the X stage 620 thereby allows the automated testing system 600 to reach the entire surface (e.g., with the footprint 2100) without adding to the machine footprint as required with dual translational actuators having a full range of motion to facilitate access to all locations on the sample. Rather than using a massive granite bridge to straddle the entire wafer for instance with a system having dual translational actuators without a rotational actuator, the cantilevered instrument column 606 (in combination with translational (constrained primarily to the X axis) and rotational stages) has a minimized arm length 902 and must reach only over half of the sample 202.

X, Y, Rotational (Theta) Deskewing/Positioning

Translational and Rotational Stages

Figure 24:
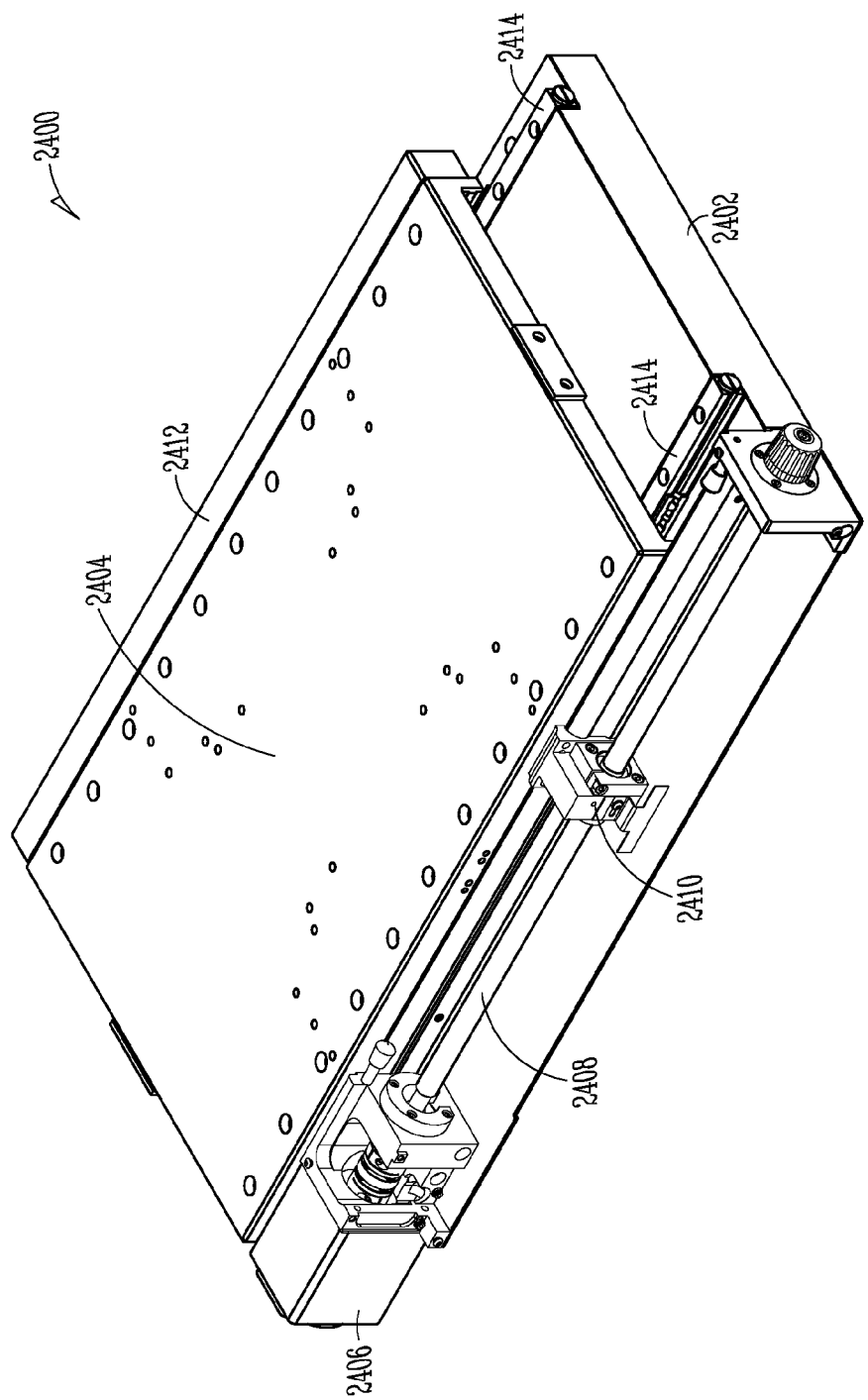
FIG. 24 is a perspective view of one example of a translational stage for use with the sample stage shown in FIG. 6A.

FIG. 24 shows one example of a translational stage 2400. In one example, the translational stage 2400 is used as a one or more of the X and Y-stages 620, 622 previously shown in FIGS. 6A and 6B. As shown in FIG. 24, the translational stage 2400 includes a stage base 2402 and a stage carriage 2404 movably coupled with the stage base 2402. A motor, such as a stepper motor 2406 configured to provide rotational motion, is coupled with one or more of the stage base or stage carriage 2404. The motor 2406 is coupled with a lead screw 2408 extending along one or both of the stage base 2402 and the stage carriage 2404. The lead screw 2408 is in turn engaged with a nut assembly 2410 coupled with one of the stage base 2402 and the stage carriage 2404. In the example shown in FIG. 24, the nut assembly 2410 is associated with the stage carriage 2404 and the motor 2406 and the lead screw 2408 are coupled with the stage base 2402. Rotation of the motor 2406 turns the lead screw 2408 which in turn moves the nut assembly 2410 along the lead screw 2408. Movement of the nut assembly 2410 along the lead screw 2408 correspondingly moves the stage carriage 2404 relative to the stage base 2402.

In one example, bearings 2414 are coupled between the stage base 2402 and the stage carriage 2404. In another example, the bearings 2414 include one or more of roller, ball, needle bearings and the like. In the example shown in FIG. 24, the bearings 2414 include cross roller bearings. In one example, the cross roller bearings 2414 include opposed rollers with each of the rollers being transverse to one another (e.g., rollers that are crossed) to provide surface to surface contact between the rolling surfaces of the bearings and corresponding square or rectangular shaped channels in each of the stage base 2402 and stage carriage 2404.

In another example, the translational stage 2400 includes an encoder, such as an optical encoder 2412, configured to measure and monitor the movement of the stage carriage 2404 relative to the stage base 2402. In one example, the encoder 2412 includes but is not limited to a linear encoder having an encoding resolution configured to measure movement of the translational stage 2400 (e.g., the stage base 2402 or the stage carriage 2404) in approximately 0.1 micron increments.

When discussing the X and Y stages 620, 622 references is made to moving one or more of the stage carriage 2404 relative to the stage base 2402 associated with each of the stages 620, 622. Where the translational stage 2400 is referred to as the X and the Y-stage one or more of the stage base or stage carriage 2402, 2404 of the associated stage is configured to move along one of the X and the Y axes. For instance, as shown in FIG. 6B the X-stage 620 includes a stage carriage 2404 shown in FIG. 24 configured to move to the left and right with respect to the page. In another example, the Y-stage 622 includes a stage carriage 2404 (also shown in FIG. 24) configured to move into and out of the page, for instance, toward and away from the cantilevered instrument column 606.

As previously described herein, in one example, the translational stage 2400 associated with the Y axis (e.g., the Y stage 622) is configured to have a smaller translational range of movement relative to the X stage 620. For instance, the predominant translational movement of the sample stage 614 is conducted by the X stage 620 moving from the left to the right as shown in FIG. 6B. The Y translation of the sample stage 614 is minimized according to a minimal range of motion provided, for instance, between the lead screw 2408 and the nut assembly 2410. As previously described herein, in one example, the Y stage 622 provide a minimal or nonexistent range of translational according to the testing needs for the particular testing system including but not limited to misalignment in the Y dimension between the optical and mechanical testing instruments 610, 612. For instance, the Y stage 622 is configured to move in a limited range of motion, for instance 5, 10, 20 millimeters and the like corresponding to the predicted misalignment in the Y direction between the optical and mechanical testing instruments 610, 612 shown in FIG. 6B. Stated another way, the Y stage 622 provides a minimal increase to the overall footprint of the sample stage 614. That is to say, the sample stage 614 has a footprint along the Y axis substantially similar or identical to the sample stage length of the sample stage 614 (e.g., the length plus a minimal translation range to compensate for an instrument misalignment). For instance, in one example, where the testing system does not include a Y stage 622 the footprint of the sample stage 614 and the Y dimension is substantially equivalent to the length of the sample stage 614 (e.g., its diameter, width, length and the like).

Figure 25:
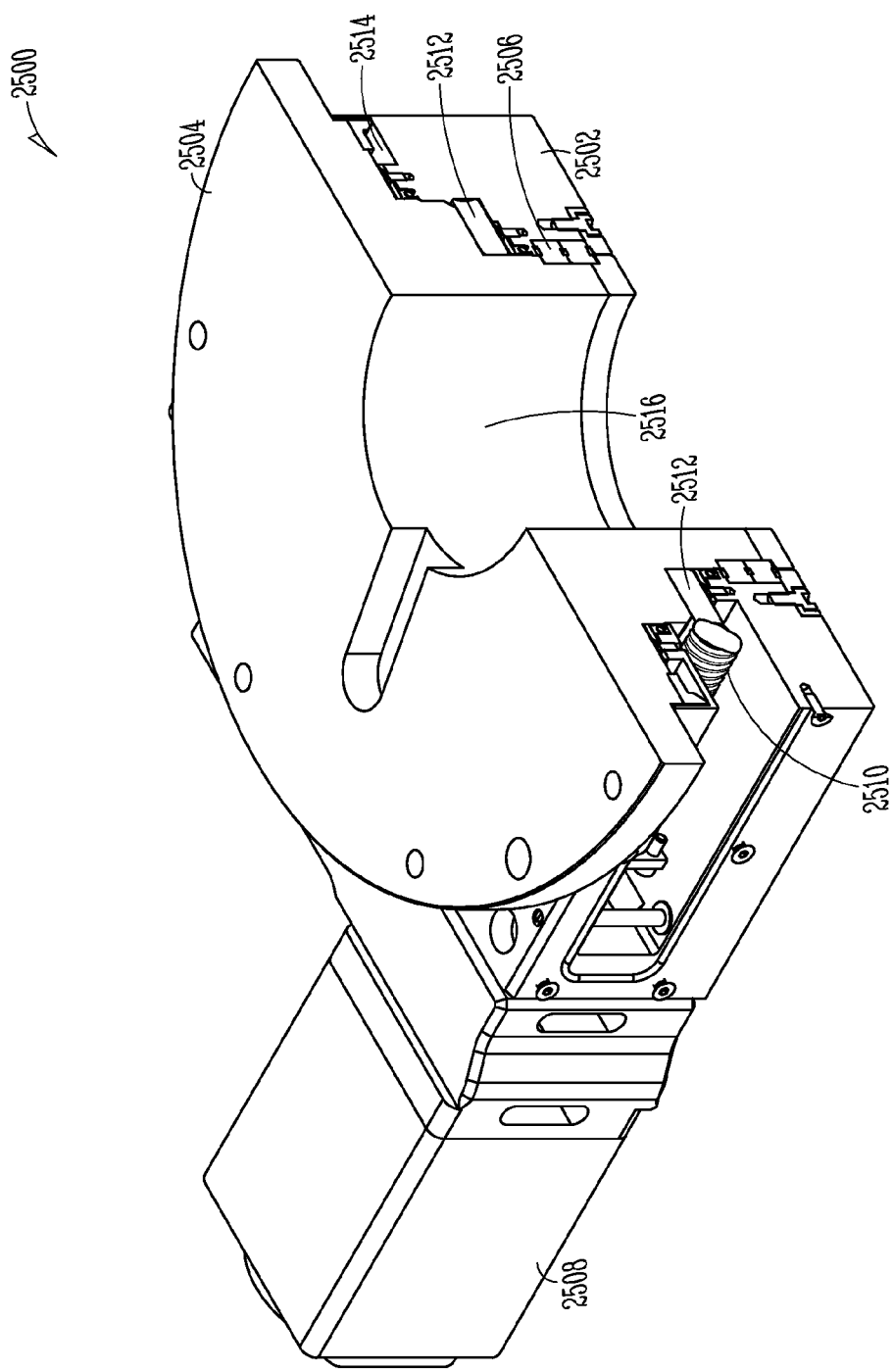
FIG. 25 is a perspective partial sectional view of one example of a rotational stage for use with the sample stage shown in FIG. 6A.

FIG. 25 shows another example of a stage. In the example shown in FIG. 25, the stage 2500 is a rotational stage, such as the rotational stage 624 previously shown in FIGS. 6A and 6B. In one example, the rotational stage 2500 provides movement such as theta movement (e.g., rotational movement around a Z axis extending through the center of the stage) for a sample coupled with the sample stage 614 (FIGS. 6A, B) relative to the remainder of the testing system. For instance, the rotational stage 2500 provides rotation of the sample relative to the optical and mechanical testing instrument 610, 612. The rotational stage 2500 as shown includes a stage base 2502 and a stage carriage 2504 rotatably coupled with the stage base 2502. In one example, a rotary bearing 2506 such as a static bearing, ball bearings, and the like is positioned between the stage base 2502 and the stage carriage 2504. A motor such as a stepper motor 2508 is coupled with one or more of the stage base 2502 and the stage carriage 2504. In the example shown in FIG. 25, the motor 2508 is coupled with the stage base 2502. The motor 2508 is configured to rotate a worm gear 2510 extending adjacent to the stage carriage 2504. As shown in FIG. 25, the stage carriage 2504 includes a ring gear 2512 coupled with the stage carriage 2504. Rotation of the worm gear 2510 through operation of the motor 2508 correspondingly rotates the ring gear 2512 and thereby rotates the stage carriage 2504 relative to the stage base 2502.

In one example, the rotational stage 2500 includes a rotary encoder 2514 such as an optical encoder adjacent to the stage carriage 2504. The rotary encoder 2514 is configured to measure and monitor the rotation of the stage carriage 2504 relative to the stage base 2502. In another example, the rotary encoder has a resolution of around about of 0.000028582 degrees.

In still another example, the rotational stage 2500 includes a utility recess 2516. In one example, the utility recess 2516 is substantially coincident with a center of the stage carriage 2504. The utility recess 2516 is sized and shaped to receive an actuator such as a lift pin actuator therein. In one example, the lift pin actuator is configured to operate one or more of the lift pins 634 shown in FIGS. 10A and 10B.

As previously described herein, in one example, the rotational stage 2500 provides for rotation to the sample stage 614 and the sample coupled thereon to substantially minimize translation in one or more axes to further minimize the overall footprint of the sample stage 614 and the corresponding testing system. For instance, the rotational stage 2500 cooperates with the translational stage 2400 (e.g., an X-stage having a larger translational range relative to a minor or minimal translational range for a Y-stage) to substantially limit the overall footprint of the sample stage 614 according to the translation of the X-stage 620 and the rotation of the rotational stage 624. Stated another way, through rotation with the rotational stage 624 and translation through the X-stage 620 all or nearly all of the locations on the sample stage 614 are fully accessible by the optical and mechanical testing instruments 610, 612 with minimal or no translation along the Y axis, for instance, with the Y stage 622. Minimizing of the translation in at least one axis, for instance, along the Y axis minimizes the overall footprint of the sample stage 614 when operated to position substantially all of the locations of the sample stage 614 underneath one or more of the optical and mechanical testing instruments 610, 612.

Coordinate Systems and Adjusting for Misalignment Between Sample and Stage

Figure 26A:
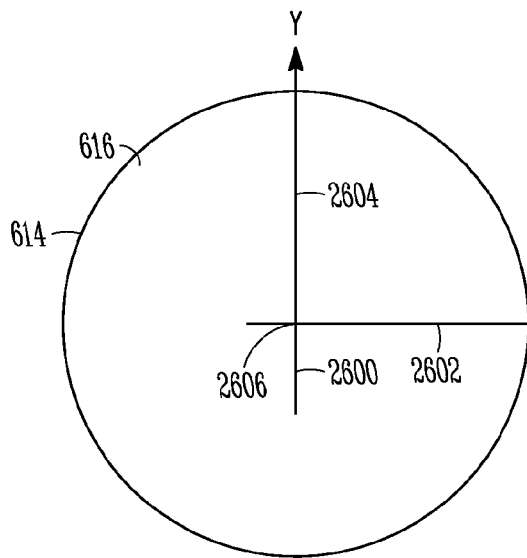
FIG. 26A is a schematic view of one example of the sample stage shown in FIG. 6A including a stage coordinate system.
Figure 26B:
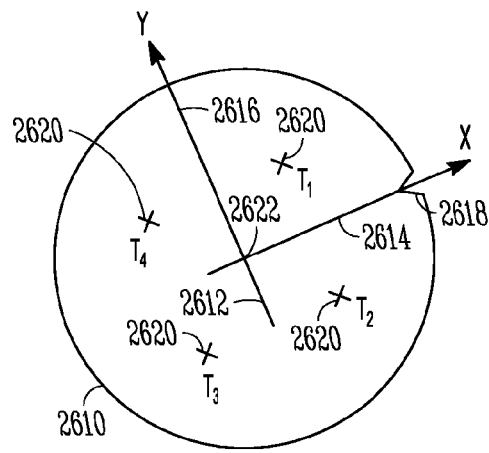
FIG. 26B is a schematic view of one example of a sample including a sample coordinate system and first and second reference marks.
Figure 26C:
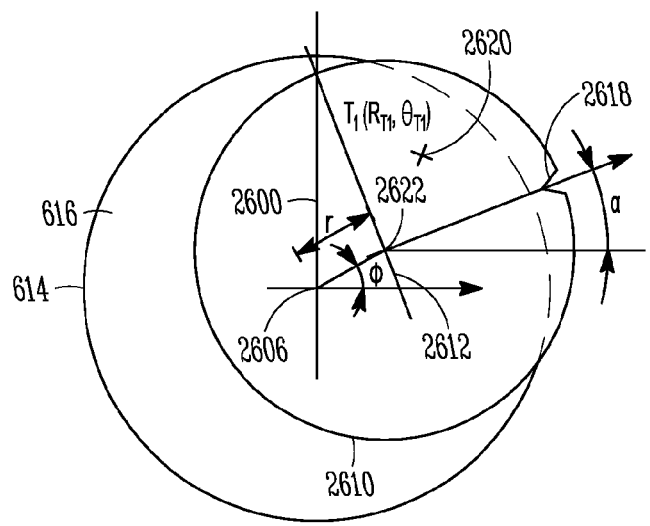
FIG. 26C is a schematic view of the sample shown in FIG. 26B coupled with the sample stage shown in FIG. 26A translational and rotational misalignment exaggerated between the sample and the sample stage.

FIGS. 26A-C show the sample stage 614 and a sample 2610 configured for coupling with the sample stage 614. Referring first to FIG. 26A, the sample stage 614 is shown including a sample stage surface 616. In the example, the sample stage 614 includes a stage coordinate system 2600 centered at a stage center 2606 such as a center of rotation of the stage 614. As shown, the stage coordinate system 2600 includes a stage X axis 2602 and a stage Y axis 2604. The stage coordinate system 2600 is fixed relative to the stage 614. Stated another way, with rotation of the stage 614, for instance through the rotational stage 2500 shown in FIG. 25, the stage coordinate system 2600 moves with the sample stage 614. Additionally, each of the stages 620, 622, 624 moves along its own respective X, Y and Z axis (in the case of the rotational stage actuator the actuator rotates around the Z axis). The respective X, Y and Z axes of the stages are another example of coordinate systems married to each of the stages (e.g., these axes are static relative to the stages).

Referring now to FIG. 26B, one example of the sample 2610 is shown in a misaligned configuration relative to the sample 614. That is to say the sample coordinate system 2612 including a corresponding sample X axis and a sample Y axis 2614, 2616 is rotated relative to the stage coordinate system 2600 shown in FIG. 26A. The sample 2610, includes the sample coordinate system 2612 fixed relative to the sample 2610. That is to say, that the sample coordinate system 2612 including the X and Y axes 2614, 2616 moves with movement of the sample 2616, for instance, in a rotational manner about the sample center 2622.

When describing the centers of the sample stage 614 the sample 2610 and other orientations features of the sample or sample stage reference is made to one or more reference points. When describing the reference points, the points are not necessarily limited to the features described herein, for instance, the reference points as shown in FIGS. 26A and 26B include but are not limited to the stage center 2606 and the sample center 2622 as well as a sample orientation feature 2618 described below. Instead, the reference points are broadly considered to be any position along one or more of the sample stage 614 and the sample 2610 and the methods described herein including the calculations based on the references points are correspondingly adjusted as needed for orienting one location on the sample relative to the sample stage 614. For instance, the sample 2610 or sample stage 614 may include one or more of a non-circular shape or have one or more set reference points that include or do not include the sample or sample stage centers.

Referring again to FIG. 26B, the sample 2610 (for instance, a semi-conductor wafer) includes a sample orientation feature (a second reference point relative to the first reference point or sample center 2622) that provides an orientation marker relative to the sample center 2622 that facilitates the locating and indexing of testing locations to position the testing locations in coincidence with one or more of the mechanical testing and optical instruments 612, 610. As shown in FIG. 26B, in one example, the sample orientation feature 2618 includes a notch formed in a perimeter of the sample 2610. In one convention, the sample orientation feature 2618 is coincident or aligned along the sample X axis 2614. As shown the sample X axis 2614 extends through both the sample orientation feature 2618 and the sample center 2622 (e.g., respective second and first reference points). As will be described in further detail below, the sample orientation feature 2618 as well as the sample center 2622 (or corresponding first and second reference points) are used to determine the alignment or misalignment of the sample 2610 relative to the sample stage 614 and thereby facilitate the accurate and precise locating of testing locations such as the testing locations 2620 (e.g. $T_{1-4}$) shown around the sample 2610.

FIG. 27C shows one example of the sample 2610 coupled over the sample stage 614 with the coordinate systems 2600, 2612 overlaid thereon. As shown the sample 2610 is misaligned (exaggerated for demonstration purposes) to show the relation between each of the coordinate systems 2600, 2612 and the reference points, such as the centers 2606, 2622 and the sample orientation feature 2618. Through detection, indexing and measuring the distances and orientations of each of these reference points accurate locating of each of the testing locations 2620 is ensured through movement of the sample stage 614 even where the sample 2610 is misaligned from the stage 614.

Instrument Offset Determination

Figure 27A:
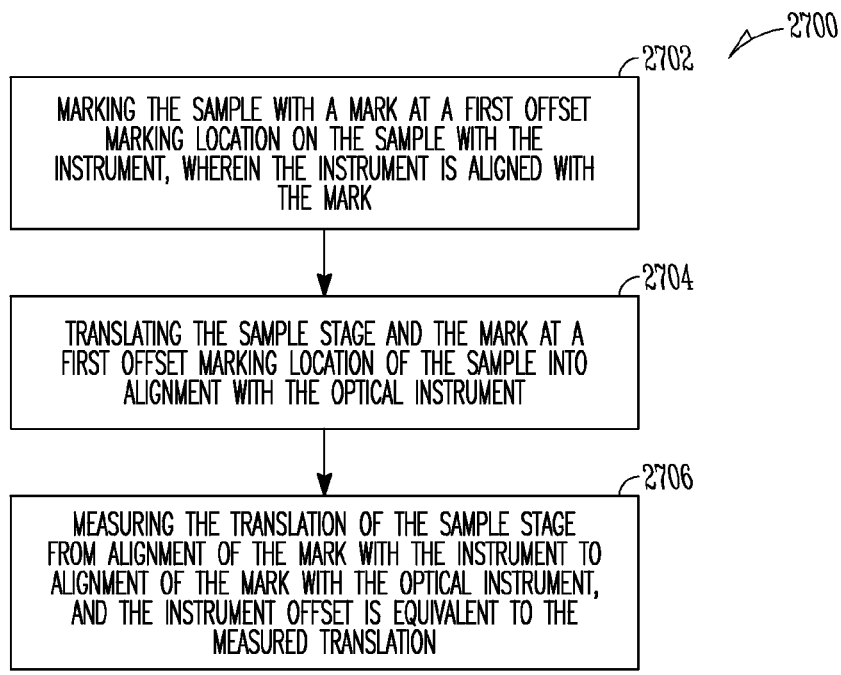
FIG. 27A is a block diagram showing one example of a method for determining an instrument offset between at least two instruments of the testing system.
Figure 27B:
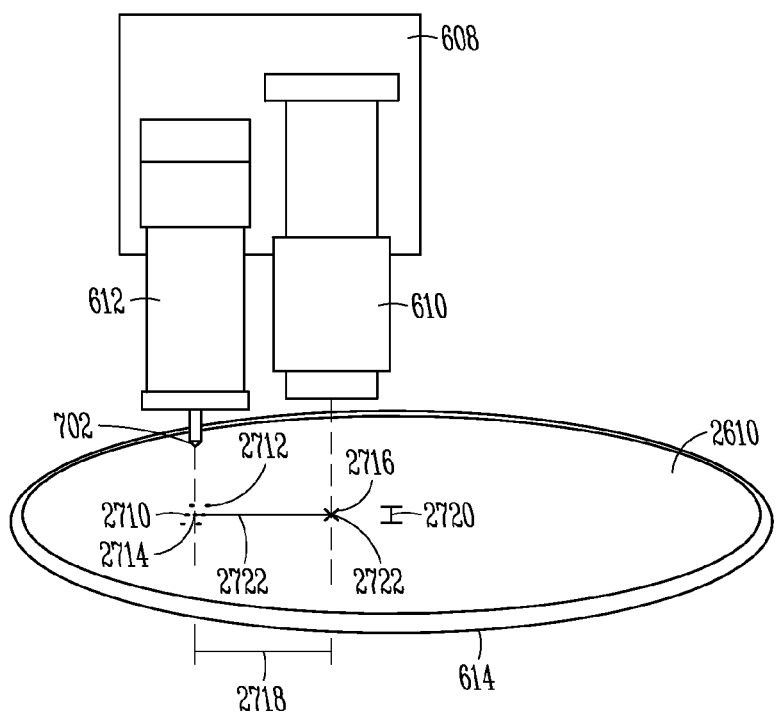
FIG. 27B is a schematic diagram showing one example of a sample stage, an initialization sample and optical and mechanical testing instruments with an instrument offset between the instruments.

FIG. 27A shows one example of a method 2700 for determining an instrument offset, for instance, an offset or lateral displacement of the mechanical testing instrument 612 relative to another instrument, such as the optical instrument 610 shown in FIGS. 6A and 6B. At 2702 the sample, such as the sample 2610 shown in FIGS. 26B and 26C, is marked with a mark such as the marking 2710 shown in FIG. 27B at a first offset marking location on the sample 2610. For instance, the marking 2710 is provided with the mechanical testing instrument 612. As shown in FIG. 27B the mechanical testing instrument 612 is aligned with the marking 2710 (because the mechanical testing instrument 610 formed the marking 2710 on the sample 2610). Optionally, the sample 2610 used for determining the instrument offset is an initialization sample (e.g., aluminum and the like) coupled with the sample stage for initialization of the testing system 600 (e.g., one or more of instrument offset or center of rotation determinations).

At 2704 the sample stage 614 and the sample 2610 are translated and the marking 2710 at the first offset marking location on the sample is moved with the sample stage 614 into alignment with the optical instrument 610. For instance, the marking 2710 and the sample stage 614 including the sample 2610 thereon are translated through one or more of X and Y translation with the X and Y-stages 620, 622 previously shown and described in FIGS. 6A and 6B.

At 2706 the translation of the sample stage 614 is measured from the previous position of alignment of the marking 2710 with the mechanical testing instrument 612 to a position aligning the marking 2710 with the optical instrument 610. The resulting instrument offset is equivalent to the measured translation. In one example the translation of the sample stage is measured according to one or more positional changes of the stage carriages 2404 of the translational stage 2400 shown in FIG. 24. As previously described, the translational stage 2400 is in one example used for each of the X and Y-stages 620, 622. The movement of the stage carriages 2404 are measured with one or more encoders 2412 associated with each of the X and Y-stages 620, 622. Because of the high resolution of the encoders 2412, the instrument offset measured with the method 2700 is configured to provide an accurate instrument offset with a resolution approaching 0.1 microns or better.

FIG. 27B shows one schematic example of the automated testing system 600 configured for determining the instrument offset 2722 as previously described with regard to the method 2700. In the example shown in FIG. 27B, the optical and mechanical testing instruments 610, 612 are coupled with an instrument stage 608, as previously shown in FIGS. 6A and 6B. The probe 702 of the mechanical testing instrument 612 has marked the sample 2610, for instance, with the marking 2710. In one example, the marking 2710 includes an identification notifier 2712, such as additional indentations, markings, or the like provided to the sample 2610. At the center or an easily recognizable location of the marking 2710 is provided a location focus 2714. For instance, in the example shown in FIG. 27B, the location focus 2714 is a single indentation at the center of the "H" pattern of the identification notifier 2712. In another example, the location focus 2714 resides in a different portion of the marking 2710, for instance, at an outlier portion of the notifier, at a point of the identification notifier 2712 and the like. As previously described, after provision of the marking 2710 to the sample 2610, the sample stage 614 including the sample 2610 thereon is translated to align the marking 2710 with the optical testing instrument 610, for instance, an optical working region 2716 of the optical instrument 2610. One example of the optical working region 2716 includes but is not limited to a focal point of the optical instrument 610.

As shown in FIG. 27B, in one example the instrument offset 2722 is a composite of an X instrument offset 2718 and a Y instrument offset 2720. In an example with an instrument offset composite 2722 as shown in FIG. 27B, measurement is performed by each of the stage actuators 620, 622, as previously described with regard to the method 2700. For instance, each of the translational stages 2400 associated with the X and Y-stages 620, 622 includes an encoder 2412 that measures the translation of the respective stages and thereby is able to determine the respective X instrument and Y instrument offsets 2718, 2720. In another example, the mechanical testing instrument 612 and the optical instrument 610 are substantially aligned along one axis, for instance, the X or Y axis. In such a circumstance, the instrument offset 2722 is equivalent to one of the X instrument offset 2718 and the Y instrument offset 2720.

In operation, after provision of the marking 2710, the sample stage 614 is actuated as previously described herein. In one example, the optical instrument 610 is operated manually to ascertain and identify the marking 2710 and focus the optical working region 2716 on the location focus 2714 to accurately and precisely determine the instrument offset composite 2722. In another example, the automated testing system 600 includes pattern recognition software configured to work with the optical instrument 610 to search for and recognize the marking 2710 and further analyze the marking 2710 (e.g., with pattern recognition software) to locate the location focus 2714. With this automated operation, the instrument stage 608 including the mechanical testing instrument 612 and the optical instrument 610 may perform an automated instrument offset determination such as method 2700 without operator input.

Center of Rotation Stage Determination

Figure 28A:
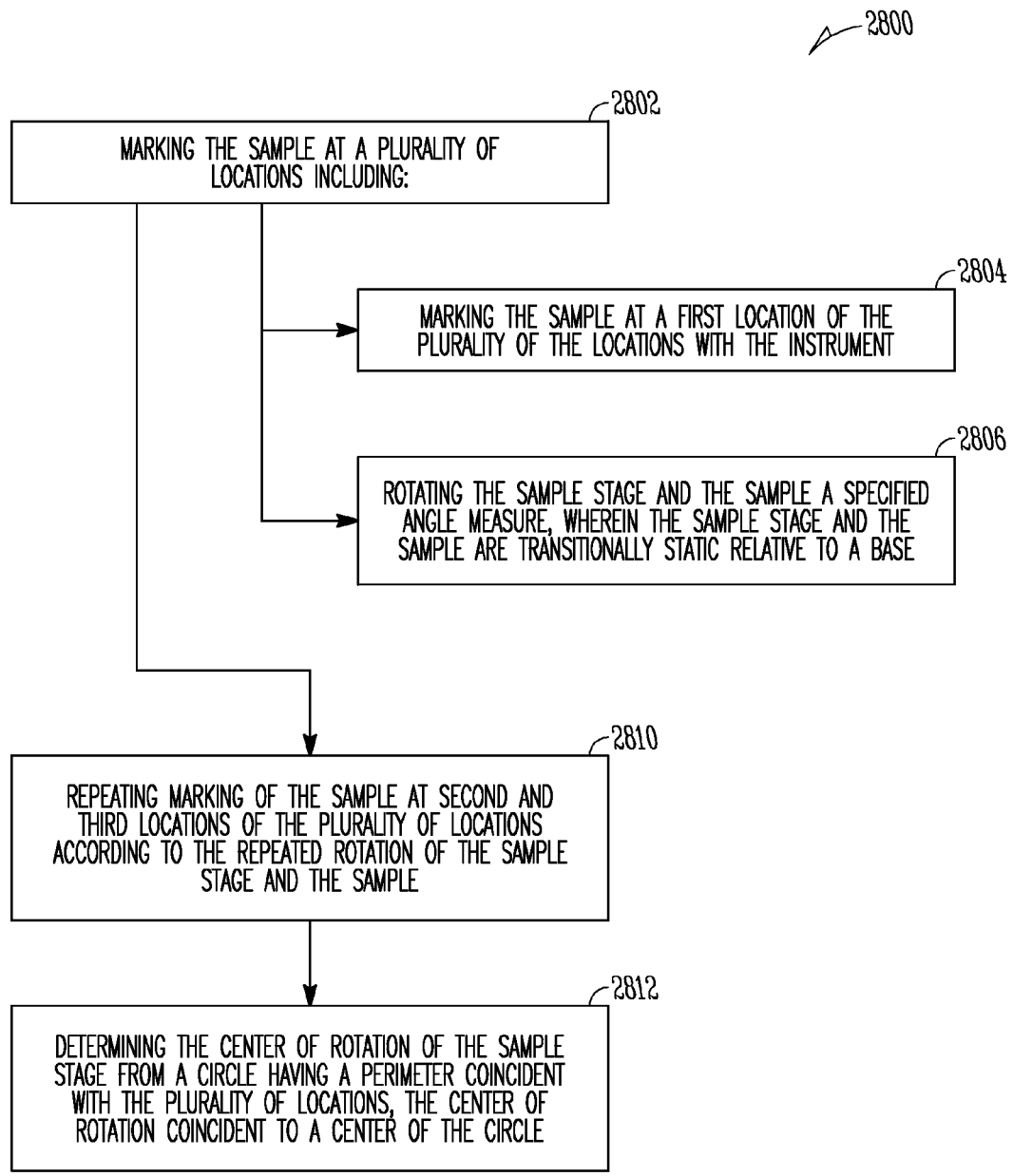
FIG. 28A is a block diagram showing one example of a method for determining a center of rotation of a sample stage of the testing system.

The method 2800 shown in FIG. 28A is one example of a method for determining a center of rotation of the stage, such as the sample stage 614 previously shown in FIGS. 6A and 6B. As will be described in detail below, the determination of the center of the stage assists in accurately locating testing locations 2620 on the sample wherein the sample is coupled along the sample stage 614. Stated another way, the stage center such as the stage center 2606 shown in FIG. 26 provides a reference point for measurement of each of the testing locations relative to the sample stage 614 and thereby allows for the accurate positioning of one or more of the mechanical and optical testing instruments 612, 610 relative to one or more testing locations 2620 on the sample 2610. At 2802, the sample such as the sample 2610 previously shown in FIGS. 26B and 26C is marked at a plurality of locations, for instance, with markings 2710 (e.g., deformations of the sample, indentations, abrasions, scratches, observable marks and the like). As previously described with regard to FIG.

27B, the markings 2710 in one example include identification notifiers 2712 and location foci 2714.

Marking of the sample at a plurality of locations (Step 2802) includes in one example marking the sample 2610 at a first location of a plurality of locations with the mechanical testing instrument 612. As previously described and shown in FIGS. 6A and 6B, the mechanical testing instrument 612 includes a probe tip 702 sized and shaped to mark the sample 2610. In one example the sample 2610 is an initialization sample sized and shaped for positioning on the sample stage 614 but is not otherwise needed for measuring of mechanical characteristics of a sample. Stated another way, the sample 2610 in this example is used primarily for initializing the automated testing system 600. For instance, the initialization sample is used for finding the stage center 2606 and the other reference points, such as reference points needed for accurate translating and rotating of the sample stage 614 and one or more testing locations 2620 into alignment with the instruments 610, 612.

Figure 28B:
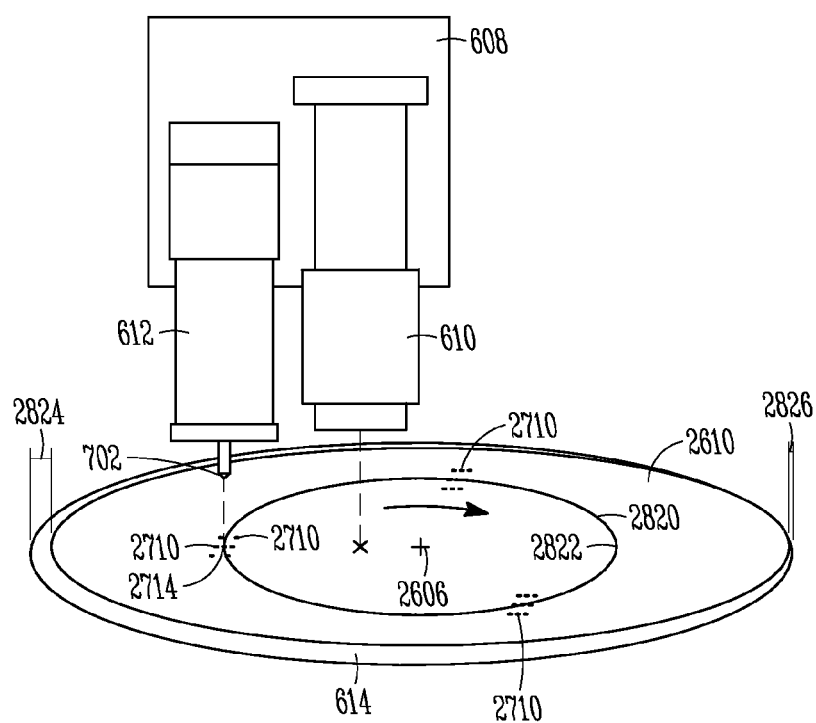
FIG. 28B is a schematic diagram showing one example of a sample stage and an initialization sample with marks at each of a plurality of marking locations on the initialization sample.

As further shown in FIG. 28B, marking the sample at a plurality of locations includes at 2806 rotating the sample stage and the sample 2610 a specified angle measure wherein the sample stage and the sample are translationally static relative to a base, such as the base of the automated testing system (e.g., the granite base or one or more of the testing system, enclosure and the like). In one example, as shown in FIG. 28B, the sample stage 614 is rotated approximately 120 degrees between each of the markings 2710. In still another example, the sample stage 614 is rotated approximately any angle measure between 0 and 360 degrees. As described below, the sample stage 614 is configured to rotate these specified amounts because a circle, such as the stage center circle 2820, will be overlaid on each of the markings 2710, for instance at the location focus centers 2714, to form a circle perimeter 2822 as shown in FIG. 28B. The provision of three or more markings 2710 ensures that the stage center circle 2820 extends around the stage center 2606 and is thereby usable to determine the stage center 2606. Stated another way, through one or more of observation and mathematical analysis of the stage center circle 2820, the stage center 2606 is accurately and reliably positioned at the center of rotation of the sample stage 614. Optionally, the specified angle for rotation includes one or more of varying or arbitrary angles. For instance, where the stage 614 remains translationally static, the provision of three markings 2710 at differing angles through rotation of the stage 614 will provide sufficient points for overlaying of the stage center circle 2820.

As further shown at 2810 in FIG. 28A, marking of the sample 2610 is repeated with at least second and third locations of the plurality of locations according to the repeated rotation of the sample stage and the sample (see Step 2806 previously described above). Stated another way, with the rotation of the sample stage 614 and the initialization sample 2610 provided thereon, a plurality of markings 2710 are provided for the sample 2610 for overlaying of the stage center circle 2820. At 2812, the center of rotation of the sample stage 614 is determined from a circle such as the stage center circle 2820 having a perimeter 2822 coincident with the plurality of locations such as the markings 2710. The center of rotation of the sample stage 614 is coincident to the center of the stage center circle 2820. That is to say, by constraining the sample stage 614 to only rotate relative to the instrument stage 608 including the mechanical testing instrument 612 thereon, providing a plurality of markings 2710 to the sample 2610 ensures that the plurality of markings when overlayed by the stage center circle 2820 determines the stage center 2606.

Turning now to FIG. 28B, a schematic example of the initialization method 2800 for determining the center of rotation of the stage 614 described in FIG. 28A is provided. For instance, a sample 2610, such as an initialization sample 2610, is coupled with the sample stage 614. As shown in one example, the initialization sample 2610 is misaligned relative to the perimeter of the sample stage 614. As shown, for instance, the sample 2610 is offset relative to the stage center 2606 according to first and second sample offsets 2824, 2826 (exaggerated for demonstration purposes). As shown, for instance, in FIG. 28B, the first sample offset 2824 is greater than the second sample offset 2826 thereby showing the sample 2610 is translated (offset) relative to the sample stage 614 at the initial positioning of the sample 2610 on the sample stage 614. The method 2800 as described herein is configured to determine the stage center 2606 corresponding to the center of rotation of the sample stage 614 even with misalignment of the sample 2610 relative to the sample stage 614.

By maintaining the mechanical testing instrument 612 in the static orientation relative to the moving sample stage 614 rotation of the moving sample stage 614 ensures that each of the markings 2710 marked in the sample 2610 are positioned around the stage center 2606 in a circle as shown in FIG. 28B. As previously described, the overlying of the stage center circle 2820 including the circle perimeter 2822 allows for the ready determination of the stage center 2606.

By using the initialization sample 2610 a sample provides a surface for marking by the mechanical testing instrument 612 (in the manner of a blank) to allow for the marking of the sample 2610 without otherwise marring the surface of the sample stage 614. After marking of the sample 2610 with the markings 2710, in one example the optical instrument 610 is used to identify each of the markings 2710, for instance, the location foci 2714, and index each of the foci relative to its position with respect to the other markings 2710. Indexing of the markings 2710 allows for the ready overlaying of the stage center circle 2820.

In one example, the method 2800 with the schematic shown in FIG. 28B includes translating the sample stage 614 and the sample 2610 (such as an initialization sample) between the plurality of locations, for instance, the markings 2710 shown in FIG. 28B. Each of the markings 2710 are observed at the plurality of locations with an optical instrument such as the optical instrument 610. Optionally, the markings 2710 are indents created with the mechanical testing instrument 612. In another example, the markings 2710 include but are not limited to scratches, abrasions, scallops and the like formed in the sample 2610.

As each of the markings 2710 are observed with the optical instrument 610, the markings 2710 are indexed at the plurality locations. For instance, the plurality of markings 2710 and their location on the sample 2610 (and relative to the stage 614) are indexed and recorded within the control station 110 shown in FIG. 1 of the automated testing assembly 100 (e.g., memory device, readable medium, disk and the like). Method 2800 further includes in another example determining the center of rotation of the sample stage (e.g., the center 2606) by forming the stage center circle 2820 having its perimeter 2822 coincident with each of the indexed markings 2710 at the plurality of locations around the sample 2610. The center of rotation of the sample stage 614 is coincident to the center of the stage center circle 2820. In one example, software such as software contained in the control station 110 of the automated testing assembly 100 is configured to overlay the stage center circle 2820 (e.g., a virtual circle) according to the markings 2710 and from the overlayed stage center circle 2820 determine the stage center 2606 through mathematical analysis of the stage center circle 2820.

Translational Deskewing of the Sample

Figure 29A:
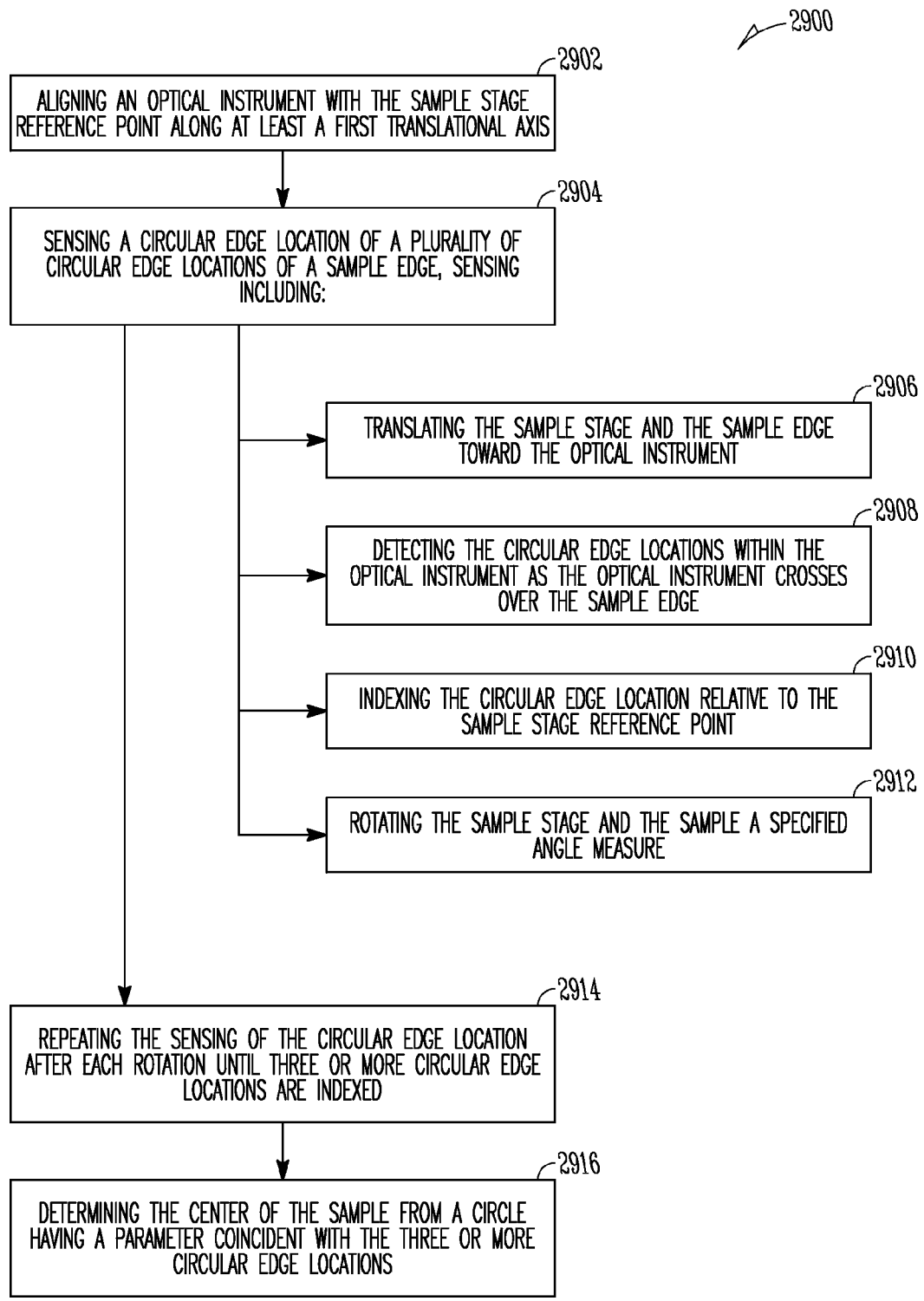
FIG. 29A is a block diagram showing one example of a method for translational deskewing of a sample on a sample stage.

FIG. 29A shows one example of a method 2900 for translational deskewing of the samples such as the sample 2610 positioned on the sample stage 614 as shown in FIG. 26C. As previously described, in some examples the sample 2610 is positioned on the sample stage 614 in a substantially aligned but not perfectly aligned orientation. For instance, one of the centers of either the sample stage 614 or the sample 2610 is offset relative to the other center. Similarly, the orientation of the testing locations on the sample 2610, including the orientation of the sample coordinate system 2612 is tilted or translated and rotated relative to a stage coordinate system, such as the stage coordinate system 2600 shown in FIG. 26A. The following deskewing methods, including translational deskewing and rotational deskewing determine the relative orientation of the sample 2610 relative to the sample coordinate system 2612 of the sample stage 614 to allow for reliable and accurate positioning of the sample 2610, including for instance, testing locations such as the testing locations 2620 shown in FIG. 26B, into alignment or coincidence with one or more working regions of the instruments of the automated testing system 600, such as the optical and mechanical testing instruments 610, 612.

At 2902, an optical instrument 610 is aligned with a sample stage reference point such as the stage center 2606 along at least a first translational axis, for instance, the stage X axis or stage Y axis 2602, 2604. With regard to the method 2900, step 2902 is optional. Although the stage center 2606 has been used as the sample stage reference point herein, in another example different sample stage reference points, such as a predetermined portion of the sample stage 614, may be used. That is to say, in another example, for instance, with a sample stage 614 having a different shape such as a circle, rectangle, square and the like, it may be more convenient for mathematical purposes to use a different sample stage reference point than the stage center 2606. With minor modifications (e.g., to the steps described herein, the corresponding mathematical analysis and the like) the methods described herein are fully applicable to sample stage reference points and first and second reference points of the samples to ensure testing locations on the sample 2610 are accurately positioned relative to the instruments of the automated testing system 600.

Figure 29B:
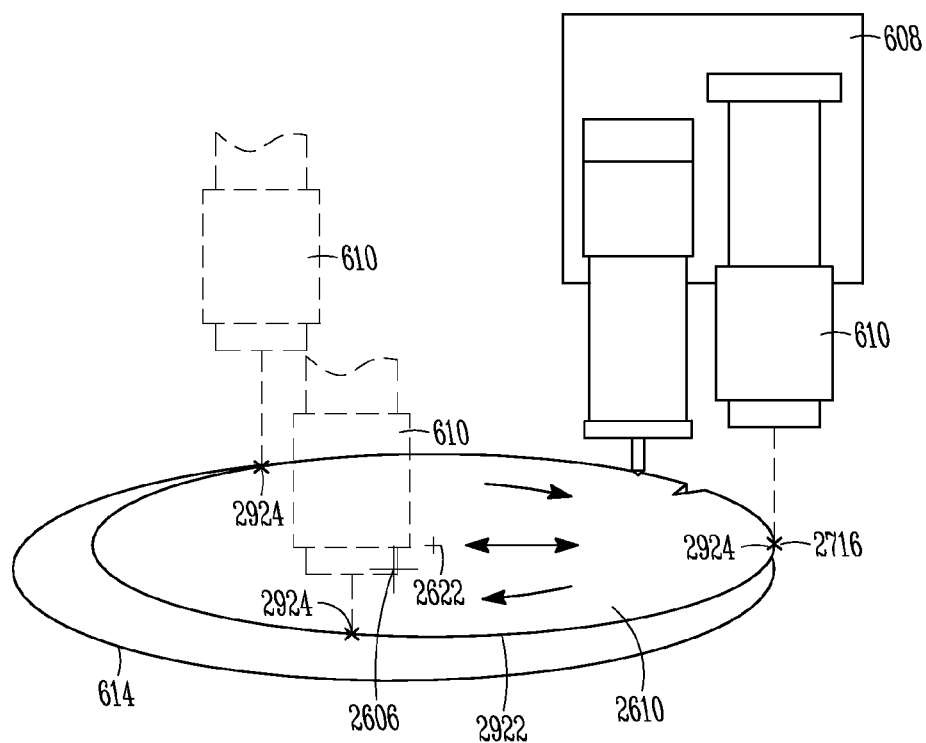
FIG. 29B is a schematic diagram showing one example of a sample coupled with the sample stage and a plurality of detected locations forming the boundaries of a translational deskewing circle, and a first reference point is the center of the circle.

At 2904, a circular edge location of a plurality of circular edge locations is sensed along a sample edge such as the sample edge 2922 of the sample 2610 shown in FIG. 29B.

In one example, sensing the circular edge location includes translating stage 614 and the sample edge 2922 toward the optical instrument 610. As previously described in one example, the sample stage 614 is moveable within the automated testing system 600, for instance, by translation and rotation relative to the optical instrument 610 and mechanical testing instrument 612.

At 2908, the circular edge location such as a sample edge location 2924 shown in FIG. 29B is detected with the optical instrument 610 as the optical instrument 610 crosses over the sample edge 2922. For instance, the control station 110 of the automated testing assembly 100 includes pattern recognition or edge recognition software configured to operate the optical instrument 610 and detect the edge of the sample 6910 as the edge of the sample passes beneath the optical instrument 610. At 2910, the circular edge location is indexed relative to the sample stage reference point such as the stage center 2606 (or any other reference point) previously shown in FIG. 28B and optionally determined with the method 2800 as described herein. At 2912, the sample stage 614 and the sample 2610 are rotated, for instance, a specified angle measure, to facilitate the observing and detecting of another of the sample edge locations 2924 shown in FIG. 29B.

At 2914, the sensing of the circular edge location such as the sample edge location 2924 along the sample edge 2922 is repeated after each of the rotations as shown in Step 2912. The sensing of sample edge locations 2924 is repeated until at least three or more circular edge locations 2924 are indexed from different locations along the sample edge 2922. As described herein, the sample stage 614 is rotated a specified angle measure. In one example, the specified angle measure includes one or more of a set or varied angular measurements such as 120 degrees, 90 degrees, 30 degrees and the like. In another example, the specified angle measure is not a set angle. Instead, three or more sample edge locations 2924 along the sample edge 2922 of the sample 2610 are detected and, as will be described below, the overlying of a circle having a perimeter coincident with each of the three or more circular edge locations will correspondently form a circle with the indexed sample edge locations 2924 that determines the first reference point of the sample 2610, for instance, the sample center 2622 as shown in FIG. 29B. Stated another way, as long as the sample stage 614 is retained in a translationally static orientation (aside from translation for edge detection) and only rotated the detecting and indexing of three or more edge locations 2924 along the sample edge 2922 creates a sufficient number of points for a virtual circle to be laid over the sample edge locations 2924 to thereby enable the easy determination of the sample center 2622, for instance, through mathematical analysis of the circle overlying the sample edge locations 2924 and coincident with the sample edge 2922.

At 2916, the center of the sample 2610 is determined from a circle such as a virtual circle having a perimeter coincident with the three or more circular edge locations 2924 spaced apart around a portion or around the entire perimeter of the sample 2610. For instance, the center of the sample 2622 is determined through mathematical analysis of the virtual circle (or the three or more edge locations 2924).

In one example, the method 2900 includes several options. In one example, translating the sample stage 614 and the sample edge 2922 toward the optical instrument 610 includes, for instance, translating the sample stage 614 and the sample edge 2922 toward the optical instrument along a second translational axis different from the first translational axis. For instance, as described at 2902, the optical instrument is aligned with at least a first translational axis, for instance, the Y axis 2604 extending through the stage center 2606 shown in FIG. 26A. In the example described herein, the sample stage 614 and the sample edge 2922 are then translated along a second translational axis such as the stage X axis 2602, also shown in FIG. 26A. Translation of the sample stage 614 from the first position along the first translational axis such as the stage Y axis 2604 and along the stage X axis 2602 readily allows for the sensing and indexing of one or more of the sample edge locations 2924 with translation of the sample stage 614 along a single axis. Stated another way, translation along two or more axes such as the X and Y axis from a first location is not required, as the translation toward the sample edge 2922 occurs along a single translational axis and allows for ready determination of the translation along the single axis relative to a predetermined point, for instance, coincident with the origin of the stage coordinate system 2600 (at the zero value of the stage Y axis 2604).

As shown in FIG. 29B, the sample 2610 is offset or misaligned relative to the sample stage 614. In practice, the sample 2610 will be more closely aligned with the sample stage 614, for instance, the perimeter of the sample 2610 will be substantially coextensive or aligned with the perimeter of the sample stage 614. That is to say, the centers of the respective sample 2610 and the sample stage 614 will be closely aligned and thereby have minimal or nonexistent offset between the two. Even with precise positioning of the sample 2610 on the sample stage 614, the processes as described herein, for instance, the method 2900 detailing translational deskewing of the sample stage 2610 relative to the sample 614 will be required to ensure accurate positioning of the plurality of testing locations 2620 of the sample 2610 according to the stage coordinate system 2600 of the automated testing system 600 (and the axes of the X and Y stages 620, 622).

Further, the schematic view shown in FIG. 29B shows a plurality of optical instrument 610 in a variety of positions around the sample stage 614, for instance, coincident with multiple sample edge locations 2924 as described herein. The plurality of optical instrument 610 are provided for the convenience of the reader. However, in actual practice, the sample stage 614 is moved as shown in FIG. 29B and the optical instrument 610 will be substantially static as shown in solid lines in FIG. 29B. The optical instrument 610 shown in broken lines are thereby provided to indicate the sample edge locations 2924 and the relative position of the optical instrument 610 relative to the detected edge locations. Stated another way, the sample edge locations 2924 around the sample 2610 are in fact positioned beneath the optical instrument 610 shown in solid lines during operation and performance of the method 2900 for translational deskewing as described herein.

As previously described, the method 2900 shown in FIG. 29A and represented in the schematic figure shown in FIG. 29B is used to determine a first reference point such as the sample center 2622 of the sample 2610. As will be described in further detail below, the sample center 2622 is used in combination with the stage center 2606 to determine the translational position of the sample 2610 relative to the sample stage 614 such as the stage center 2606. Referring to FIG. 26C the position of the sample 2610 for instance the position of the sample center 2622 relative to the stage center 2606 is the "r" measure shown in FIG. 26C. For instance the sample center 2622 has a radius and an angular orientation corresponding to the (measurement shown in FIG. 26C (e.g., a first reference angular offset). Stated another way, the sample center 2622 is a first reference point of the sample stage 2610 and has an angular and radial position relative to the stage coordinate system 2600 including the stage center 2606. As will be described in further detail below this first reference point position relative to the stage center 2606 will be used to transform the locations of the testing locations 2620 shown in FIG. 26B into corresponding rotational and translational movement of the sample stage 614 to ensure alignment of the plurality of testing locations 2620 with one or more of the mechanical and optical testing instrument 612, 610 even where the sample 2610 is misaligned relative to the sample stage 614.

Rotational Deskewing of the Sample

Figure 30A:
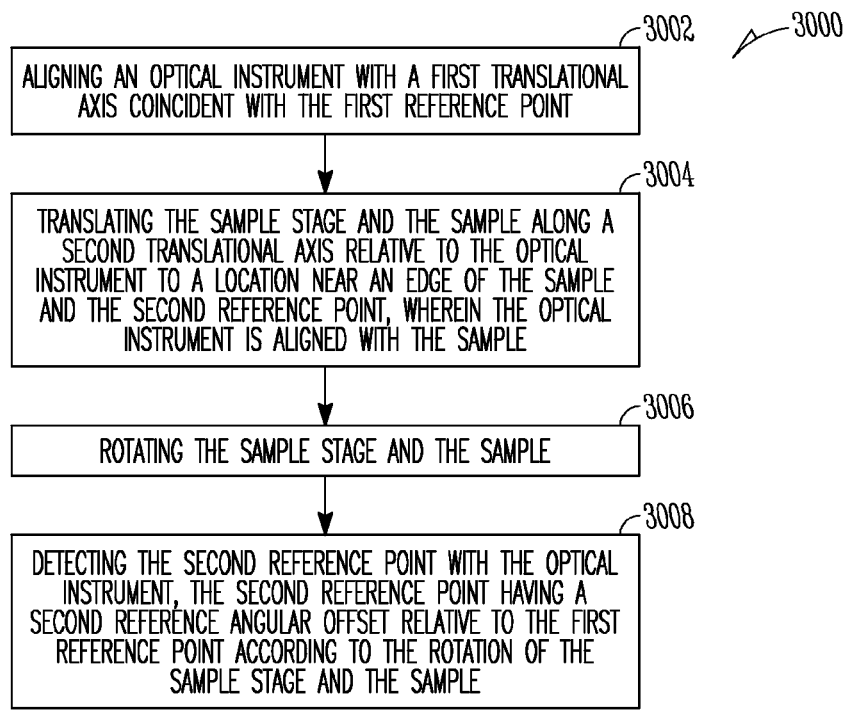
FIG. 30A is a block diagram showing one example of a method for rotational deskewing of a sample on a sample stage.

FIG. 30A shows one example of a method 3000 for rotationally deskewing a sample, such as the sample 2610, relative to the sample stage 614. As previously described in at least some examples, the sample 2610 is positioned on the sample stage 614 and despite efforts to perfectly align the sample 2610 with the sample stage 614 some amount of misalignment may occur between the sample and the sample stage. The rotational deskewing method 3000 provided herein cooperates with the translational deskewing method 2900 previously described to index and orient the sample 2610 relative to the sample stage 614 for accurate positioning of the plurality of testing locations 2620 shown in FIG. 26B relative to the coordinate system of the sample stage 614 for accurate positioning of the testing locations in alignment with one or more of the optical and mechanical testing instruments 610, 612 through operation of the automated testing system, for instance, through operation of the X-stage 620, Y-stage 622 and the rotational stage 624.

At 3002, an optical instrument 610 is aligned with a first translational axis coincident with the first reference point. For instance the optical instrument 610 is aligned with a translational axis such as a Y axis extending through the sample center 2622 and substantially parallel to the stage Y Axis 2604 shown in FIG. 26A. Method step 3002 is optional with regard to the method 3000. For instance, the optical instrument 610 is unaligned with one or more of the Y or X axes at the outset of the method 3000. At 3004, the sample stage and the sample 614, 2610 are translated along a second translational axis relative to the optical instrument 610 to a location near an edge of the sample, for instance, the sample edge 2922. Further the sample stage and the sample 614, 2610 are translated so the sample orientation feature 2618 (e.g., a second reference point) is positioned substantially near the working region of the optical instrument 610. That is to say, the optical instrument 610 is aligned with a portion of the sample, for instance, a portion of the sample 2610 near the sample orientation feature 2618. The optical instrument 610 is positioned in an orientation that allows for ready detection of various portions of the sample orientation feature 2618.

At 3006, the sample stage 614 and the sample 2610 are rotated, for instance around the center of rotation 2606 (e.g., the stage center 2606). Rotation of the sample stage 614 and the sample 2610 where the optical instrument 610 is positioned near the sample orientation feature 2618 allows for the ready examination of various portions of the sample orientation feature 2618. For instance, the sample orientation feature 2618 includes a first feature portion 3020 and a second feature portion 3022. In one example, the sample orientation feature 2618 includes the first and second feature portions 3020, 3022 and each of the portions 3020, 3022 are readily configured for discrimination and identification from one another. At 3008, the sample orientation feature 2618 (the second reference point of the sample) is detected with the optical instrument. The sample orientation feature has a second reference angular offset relative to the first reference point (e.g., the sample center 2622 and an X-axis parallel to the stage X axis 2602) according to the rotation of the sample stage 614 and the sample 2610.

Figure 30B:
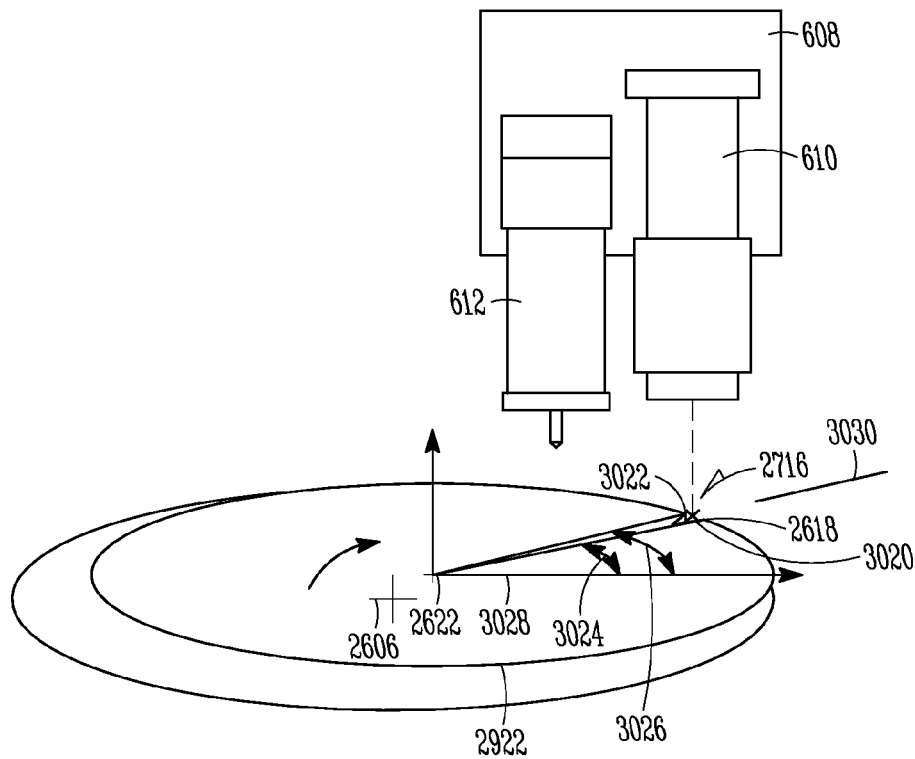
FIG. 30B is a detailed schematic diagram showing one example of a sample having a second reference point at a second reference angular offset to a first reference point.

Optionally, the sample reference point 2618 includes the first and second feature portions 3020 and 3022. The first and second feature portions 3020 and 3022 are detected with the optical instrument 610. The first feature portion 3020 has a first angular measurement 3024 and the second feature portion 3022 has a second angular measurement 3026 different from the first angular measurement 3024. For instance, as shown in FIG. 30B each of the first and second feature portions 3020, 3022 have corresponding first and second angular measurements 3024, 3026 relative to the sample center 2622 and a transposed stage X axis 3028 extending through the sample center 2622 (and parallel to the stage X axis 2602 in FIG. 26A). In one example the first and second angular measurements 3024, 3026 thereby provide an angular measure of the sample orientation feature 2618 relative to the sample center 2622 according to the coordinate system of the sample stage 614.

Optionally, the first and second angular measurements 3024, 3026 are averaged and the average of the first and second angular measurements is the second reference angular offset. In one example, the second reference angular offset indicates the orientation of the sample 2610 relative to the sample center 2622 and correspondingly to the sample stage 614. As shown in FIG. 26B, each of the testing locations 2620 is oriented relative to the stage center 2606 and the sample coordinate system 2612. By determining the orientation of the sample orientation feature 2618 relative to the sample center 2622 the orientation of the sample 2610 is determined to thereby allow for the ready positioning of the sample stage 614 with the sample 2610 thereon for alignment of one or more of the testing locations 2620 with the optical and mechanical testing instruments 610, 612 despite misalignment of the sample 2610 relative to the sample stage 614.

As will be described in further detail below the determination of the stage center 2606, the sample center 2622 (a first reference point of the sample) and the second orientation feature 2618 (a second reference point indicative of the second reference angular offset of the sample 2610 relative to the sample stage 614) allows for the ready positioning and aligning of the testing locations 2620 through mathematical analysis with one or more of the optical and mechanical testing instrument 610, 612 as described herein. Stated another way, with the combination of the features shown in FIG. 26C, for instance the values of r, and a corresponding to the positions and orientations of the stage center 2606 relative to the sample center 2622 and the orientation of the sample orientation feature 2618 relative to the sample center 2622 substantially any position on the sample 2610 (such as the testing locations 2620) may be readily positioned with accuracy and precision relative to the optical and mechanical testing instruments 610, 612.

As described above, the method 3000 optionally includes detecting the first and second feature portions 3020, 3022 of the second reference point, such as the sample orientation feature 2618, for instance with the optical instrument 610. The second feature portion 3022 is in another example spaced from the first feature portion 3020 a specified angle. For instance, the second feature portion 3022 is adjacent to the first feature portion 3020 and is angularly offset from the first feature portion 3020 a known value. Because the second feature portion 3022 is offset a specified amount, in one example averaging the first and second angular measurements uses the measure determined for the first feature portion 3020 for instance through detection with the optical instrument 610 in combination with the specified angular position of the second feature portion 3022 relative to the first feature portion 3020 to determine the second reference angular offset (e.g., the average of the angular measurement of the first feature portion 3020 and the same angle adjusted a known amount for the second feature portion 3022) of the sample orientation feature 2618.

In the example shown in FIG. 30B, the second reference angular offset 3030 is shown as a bisecting line extending between the first and second angular measurements 3024, 3026 (i.e. the second reference angular offset 3030 is the average of the first and second angular measurements 3024, 3026). In yet another example the sample orientation feature 2618 shown in FIG. 30B for instance is a marking point and the easily recognizable by the optical instrument 610. For instance, the second orientation feature 2618 in one example is similar to the marking 2710 shown in FIG. 27B. For instance the marking 2710 includes an identification notifier 2712 to make the marking readily identifiable and further includes a location focus 2714 to provide an exact position for the sample orientation feature 2618 as it relates to the sample center 2622. In such an example a single angular measurement is needed from the location focus 2714 relative to the sample center 2622 to determine the orientation of the sample orientation feature 2618 relative to the sample center 2622. In such an example, the method 3000 shown in FIG. 30A includes rotating the sample stage 614 so the sample orientation feature 2618 is aligned with the optical instrument 610. In this example a single angle is measured in place of measuring multiple angles as described in one example herein.

Aligning an Instrument with One or More Test Locations

Figure 31A:
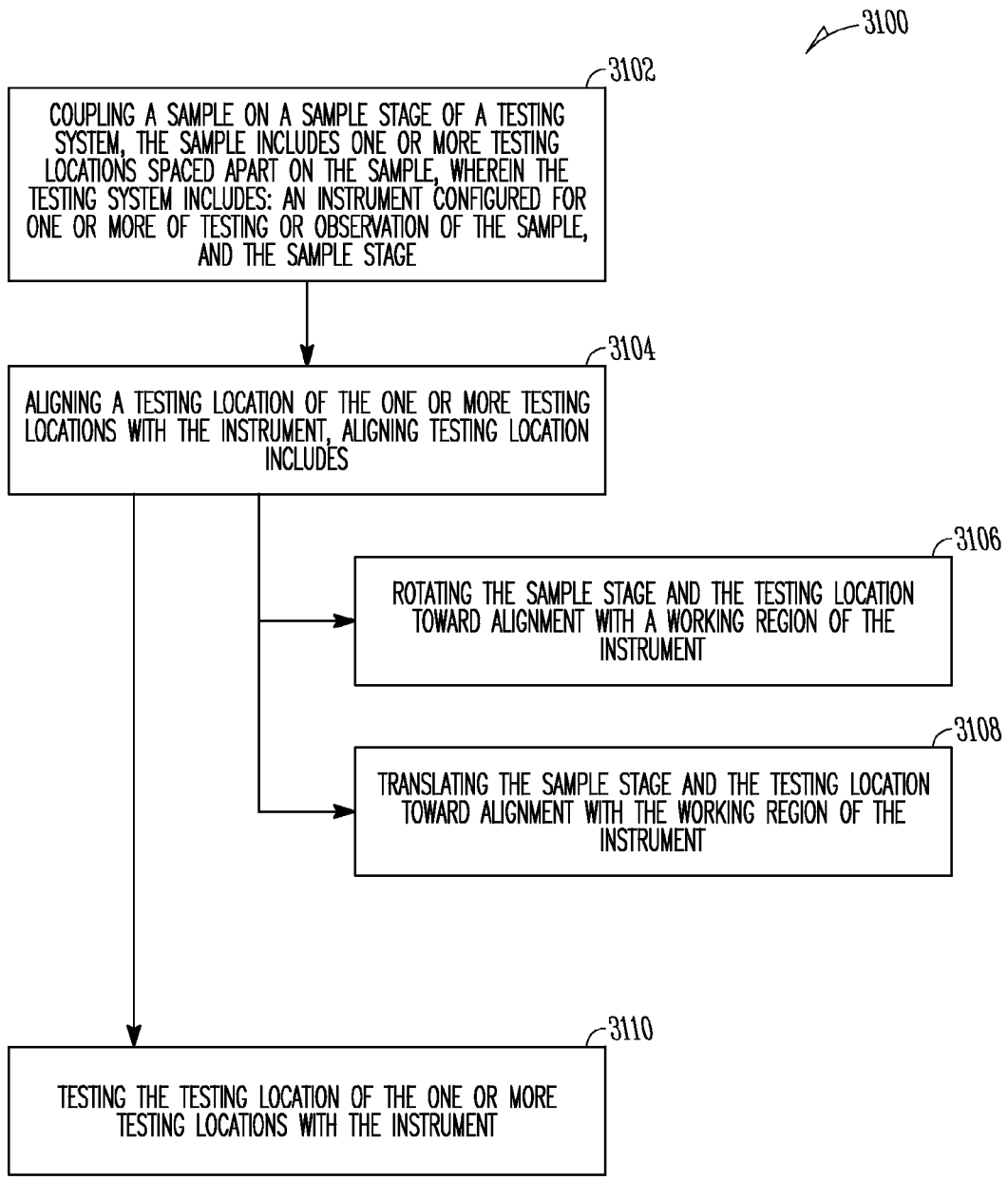
FIG. 31A is a block diagram showing one example of a method for aligning an instrument with one or more test site locations of a sample.

Referring now to FIG. 31A one example of a method 3100 for aligning one or more testing locations with an instrument is provided. At 3102 a sample such as the sample 2610 is coupled on a sample stage, such as the sample stage 614 of a testing system 600. The sample 2610 includes one or more testing locations 2620 spaced apart on the sample 2610. In one example, the testing system 600 includes an instrument, such as an optical or mechanical testing instrument 610, 612 configured for one or more of testing or observation of the sample 2610 on the sample stage 614. In another example, the testing system 600 includes the features shown for the testing system 600 provided in FIGS. 6A and 6B.

At 3104 a testing location such as one or more of the testing locations 2620 shown in FIGS. 26B, C is aligned with the instrument such as the mechanical testing or optical instrument 612, 610. In one example, aligning the testing location 2620 includes, at 3106, rotating the sample stage 614 and the testing location 2620 position on the sample 2610 toward alignment with a working region of the instrument such as a probe tip 702 or an optical working region 2716 of the optical instrument 610. In another example, aligning the testing location of the 2620 of the one or more testing locations with the instrument includes, at 3108, translating the sample stage 614 and the testing location 2620 toward alignment with the working region of the testing instrument (again, for instance the optical working region 2716 or the probe tip 702).

At 3110 the testing location 2620 is tested with one or more of the instruments 610, 612. For instance, in the example of the mechanical testing instrument 612, the mechanical testing instrument 612 is configured to indent, scratch, abrade, delaminate or provide any one of a plurality of mechanical testing operations at the testing location 2620. In another example the optical instrument 610 includes but is not limited to one or more of an optical instrument, a microscope, scanner and the like configured to observe and detect (whether through visible light detection, electron scanning or transmission, observation with other light wavelengths and the like) various features of the sample 2610 at the testing location 2620.

Several options for the method 3100 follow. In one example, testing includes one or more of mechanical testing or observation at micron or less scale with the instrument, such as one or more of the mechanical and optical testing instruments 612, 610. For instance, the mechanical testing instrument 612 is configured to provide an indentation, deformation or other marking to the sample 2610 at a micron (e.g., up to a multiple micron scale). In another example, the mechanical testing instrument 612 is configured to provide an indentation at less than a micron scale, for instance at a nano scale. In yet another example, the optical testing instrument 610 is similarly configured to observe mechanical characteristics and features of the sample 2610 at micron (e.g., up to a plurality of micron scale) and at the nano scale.

In yet another example, the method 3100 includes translating the sample stage as previously described herein. In one option translating the sample stage includes translating the sample stage 614 along an X axis such as an X axis provided by the X-stage 620. In another example, translating the sample stage includes constraining translation (e.g., limiting) of the sample stage 614 along another axis such as the Y axis for instance an axis aligned with the movement direction of the Y-stage 622 previously shown in FIGS. 6A and 6B. In one example the Y axis of the Y stage 622 is substantially parallel to a cantilevered instrument arm 607 as previously described herein.

In another example, constrained translation of the sample stage 614 along the Y axis includes translating the sample stage along the Y axis between the instrument and another instrument for instance according to the instrument offset as previously described herein and shown for instance in FIG. 27B and determined by way of the method 2700 shown in FIG. 27A. That is to say, the Y stage 622 is configured to move the sample stage 614 in a manner substantially constrained or limited according to the instrument offset composite 2722 (e.g., the Y instrument offset 2720) shown in FIG. 27B. The sample stage 614 thereby provides a sample stage footprint substantially similar to the length or width of the sample stage 614 along the Y axis. In other words, the sample stage footprint along the Y axis is only slightly larger than a dimension of the sample stage, such as length, according to the instrument offset.

In yet another example, aligning the testing location 2620 of the one or more testing locations with the instrument includes rotating the sample stage 614 and the testing location 2620 into coincidence with the X axis for instance the X axis of the X stage 620 where the testing location has an original non-zero Y location relative to the Y axis. For instance referring to FIG. 26A, the stage X axis 2602 is substantially aligned with the movement axis of the X stage 620 previously shown and described in FIGS. 6A and 6B. In one example where a testing location such as one of the testing locations 2620 in its original position is not aligned with the stage X axis 2602, the stage 614 is rotated to position the testing location 2620 in coincidence with the X axis (linear movement axis) of the X-stage 620.

By moving the testing location 2620 into coincidence with the X axis of the stage 620 (the linear movement axis of the X-stage 620) Y translation, for instance along the Y axis of the Y stage 622 (the linear movement axis of the Y-stage 622), is thereby substantially minimized or entirely eliminated. Instead, translation for instance with the X stage 620, is used to move the testing location 620 into coincidence or alignment with one or more of the instruments such as the mechanical and optical testing instrument 612, 610.

In yet another example aligning the testing location with the instrument includes translating and rotating the sample stage 2610 and the sample 614 within the sample stage footprint 2100 (see FIG. 21A) hounded by the outermost perimeter surfaces of the sample stage relative to the instrument (e.g., 610, 612) in a plurality of orientations configured to selectively align the instrument with substantially the entire surface area of the sample stage. For instance, as shown in FIG. 21A the optical instrument 610 is provided at the center of the first footprint 2100 (e.g., the sample stage footprint 2100). As shown, the sample stage footprint or first footprint 2100 is bounded by the outermost perimeter surfaces and the sample stage 614 according to translation of the sample stage 614 along the X axis (linear movement axis of the X-stage 620) and rotation of the sample stage with the rotational stage 624. As shown, the Y component 2101 of the first footprint 2100 is substantially minimized through the combination of X translation and rotation of the sample stage 614. Stated another way, each of the target locations shown in FIG. 21A (for instance at the outermost and innermost portions of the stage) are positionable in alignment with the optical and mechanical testing instruments 610, 612 with the stage 614 moved into one or more orientations within the first footprint 2100 shown in FIG. 21A. Optionally, the sample stage footprint 2100 is within a testing system footprint including the sample stage footprint 2100 and a column footprint bounded by a column base 605 (shown in FIG. 9). As shown in FIG. 9 the column base 605 is a portion of the cantilevered instrument column 606 coupled with the instrument 610, 612.

Transformation of Sample Based Testing Location Coordinates

As previously described herein, the first and second reference points of the sample 2610, for instance the sample center 2622 and the location and orientation of the sample orientation feature 2618 are used in combination with the stage reference feature (a sample stage reference point, such as the stage center) 2606 to accurately position one or more of the plurality of testing locations 2620 in coincidence or alignment with one or more instruments such as the optical and mechanical testing instruments 610, 612. As shown for instance in FIG. 26C, the orientation of each of these features relative to each other provides positional coordinates shown for instance with the variables r, $\phi$, and $\alpha$ where r is the radius of the sample center 2622 from the stage center 2606, $\phi$ is the angle measurement of the sample center 2622 relative to the stage X axis 2602 and the stage center 2606 and $\alpha$ is the angle measure of the sample orientation feature 2618, for instance the second reference angular offset 3030 shown in FIG. 30B. Each of these values is used in one example to mathematically determine the position of the testing locations 2620 according to the stage coordinate system 2600 for positioning by the X, Y and rotational stages 620, 622, 624 of the automated testing system 600. Stated another way, these values facilitate the accurate positioning of each of the testing locations 2620 relative to one or more of the optical and mechanical testing instrument 610, 612 despite misalignment between the sample 2610 and the sample stage 614.

Figure 31B:
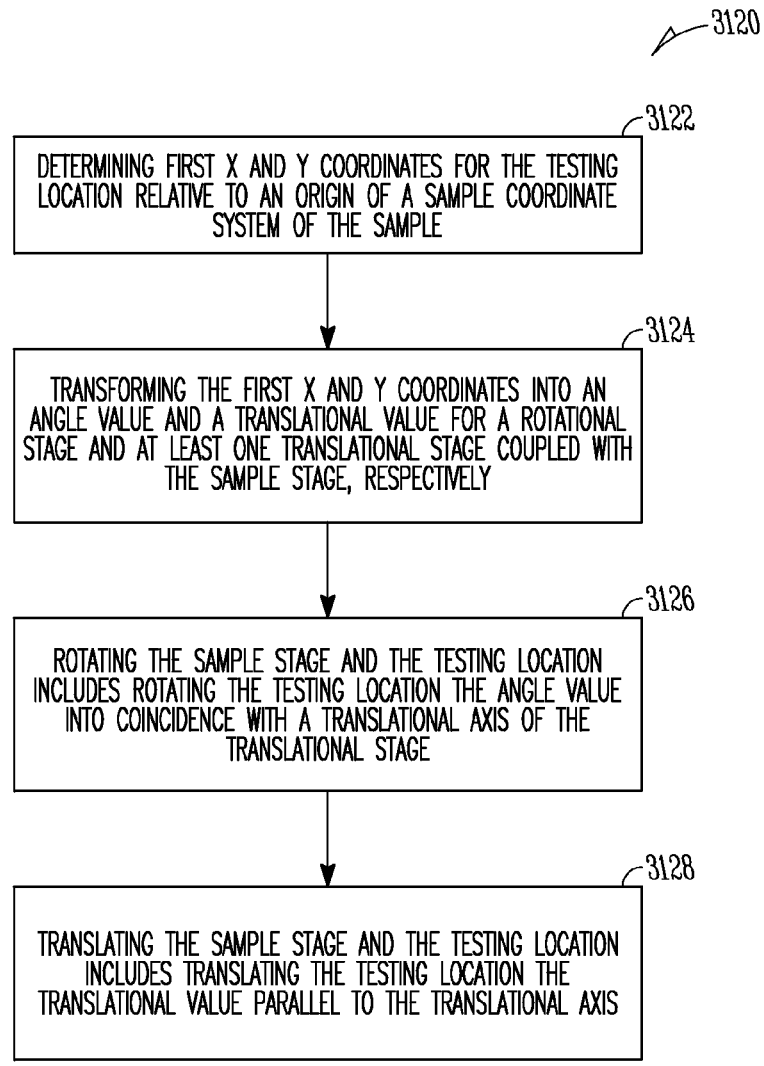
FIG. 31B is a block diagram showing one example of a method for aligning an instrument with one or more test site locations of a sample based on a coordinate system of the sample.

For instance, referring to FIG. 31B, one example of a method 3120 for aligning the testing location 2620 of the one or more testing locations with the instrument (e.g., one or more of the instruments 610, 612) includes determining the first X and Y coordinates for the testing location 2620 relative to an origin such as the sample center 2622 of the sample 2610. As previously described the sample coordinate system 2612 is in one example centered or has an origin at the sample center 2622 as shown in FIG. 26B. At 3124 the first X and Y coordinates of the testing location 2620 (e.g., $T_1$) are transformed into an angle value $\Theta_{T1}$ and a translational value $R_{T1}$ for a rotational stage and at least one translational stage (e.g., stages 624, 620) respectively coupled with the sample stage 614 as shown by the coordinates for $T_1$ in FIG. 26C.

With the rotational and translational values determined at 3126 the sample stage 614 and the testing location 2620 on the sample 2610, are rotated. In one example, the testing location 2620 is rotated according to the angle value $\Theta_{T1}$ into coincidence with a translational axis such as the X axis of the X-stage 620 (e.g., the testing location is on a line parallel to the linear movement axis of the stage). At 3128, the sample stage 614 and the testing location 2620 are translated according to the translational value $R_{T1}$ parallel to the translational axis described above. That is to say, the testing location is translated along a line parallel to the translation axis of the stage, such as the X-stage 620, the translational value $R_{T1}$.

In another example, the method 3120 includes first translating the sample stage 614 along a translational axis parallel to the movement axis of the translational stage such as the X-stage 620. Thereafter the sample stage 614 is rotated to bring the testing location 2620 into coincidence with the X-stage translational axis.

In another example the method 3120 includes rotating the sample stage 614 and each of the one or more testing locations 2620 (e.g., $T_1$-$T_4$) into respective coincidence with the translational axis of the translational stage, such as the X stage 620. Stated another way, the plurality of testing locations are separately positioned along a line parallel to the linear movement axis of the X-stage 620. In yet another example, rotating the sample stage 614 and each of the one or more testing locations respective angle values (e.g., $\Theta_{T1-4}$) into respective coincidence with the translational axis of the translational stage includes moving the testing locations 2620 into coincidence with a translational axis aligned or coincident with the working region (the focal point or probe tip) of the instruments 610, 612 and parallel to a movement axis of one of the translation stages 620, 622. By rotating the testing locations into alignment with a single translational axis extending through the working region, translational movement with, for instance the X-stage 620, is able to move the testing location 2620 into coincidence with the instrument 610, 612.

The testing locations 2620 in coincidence with the translational axis (e.g., on a line parallel to the translational axis) are translated R values, such as $R_{T1-4}$, to move the testing locations 2620 into alignment or coincidence with the working regions (e.g., region 2716 or the probe tip 702 shown in FIG. 27B) of the optical and mechanical testing instruments 612, 610. Rotating of the sample stage 614 and the testing location 2620 of interest for the testing procedure into coincidence with the translational axis substantially eliminates translation along a second translational axis different from the first translational axis (such as the Y axis of the Y-stage 622). For instance, the testing locations 2620 positioned away from the stage and sample X and Y axes 2602, 2604 and 2614, 2616 are positioned along the translational axis (i.e., the linear axis of movement) of the X-stage 620 to substantially eliminate translation of the sample stage 614 and the testing locations 2620 of the sample 2610 for instance along another translation axis such as the axis of the Y-stage 622. Optionally, the stage 614 is translated first according to the $R_{T1-4}$ of each of the testing locations 2620 and thereafter rotated according to the $\Theta_{T1-4}$ of each of the locations.

A prophetic example is provided below that determines the coordinates and relative positions of the first and second reference points 2622 and 2618 of the sample 2610 as well as the sample stage reference point 2606 (in one example the center of the stage 614) and then uses corresponding values (r, ϕ, α and the like) to determine the translational and angular coordinates for one or more testing locations 2620. The prophetic example is conducted according to the methods described herein and shown in the Figures. The prophetic example is provided as a series of steps. It will be apparent that many of the steps in the prophetic example may be rearranged or modified and continue to come within the umbrella of methods and apparatus described herein. Modifications of the sample stage shape, specified reference points (i.e., non-center points) and the like will modify the steps and corresponding mathematical analysis used herein, and such modifications are fully within the scope of the disclosure.

Machine Setup/Initialization

1. Home the X-stage 620, Y-stage 622, Z1—first instrument stage 608, Z2—second instrument stage 608 and the Theta stage 624.
2. Perform a Tip to Optics Calibration—This procedure allows the machine to make a mark on a sample and then move the mark precisely under the optics for viewing by the operator.
   a. Attach a Sample (e.g., an initialization sample) such as Polycarbonate to the stage 614. Optionally, may used one of the diagnostic samples 1106 at the stage receptacles 628 on the stage receptacle flange 630.
   b. Use the GUI (e.g., the control station 110) to manually move the X, Y, Theta, and Z1 stages so the sample is located under the optical instrument 610 and the optics are focused on the sample.
   c. Perform an H-Pattern marking 2710 (or other similar pattern to assist in calibration) for the Tip to Optics Calibration including:
      i. The automated testing system 600 will move the X and Y-stages 620, 622 the nominal offset distance between the tip and optics (e.g., the mechanical testing instrument 612 and the optical instrument 610) so the tip 702 is approximately over the same sample location that was viewed with the optics. The Theta stage 624 is static.
      ii. The GUI control station 110 will instruct the operator to manually move the Z1 stage 608 down until the tip 702 is within about 1 mm of the sample height.
      iii. The GUI control station 110 will slowly (e.g., at a slower pace than the initial approach) continue to move the Z1 stage 608 down until it detects contact with the sample.
      iv. The mechanical testing instrument 612 will perform a series of indents in the shape of an H to form the marking 2710.
      v. The automated testing system 600 will return the X, Y, and Z1 stages 620, 622 and 608 to the original optics position.
      vi. The GUI control station 110 will instruct the operator to move the X and Y-stages 620, 622 until the center of the H pattern marking 2710 (e.g., the location focus 2714) is aligned with reticle in the camera. Optionally, pattern recognition software instructs and controls the optical instrument 610 in a similar manner to find the location focus 2714.
      vii. The automated testing system 600 will calculate and record the exact X, Y, and Z1 displacement between the tip and the optics locations (e.g., the instrument offset composite 2722 between the mechanical testing and optical instruments 612, 610).
3. Perform a Center of Rotation Calibration—This procedure assists in achieving accurate alignment of testing locations 2620 on the sample 2610 with one or more instruments. This procedure locates the center of rotation of the stage 614 within a tolerance of around about 1 micron.
   a. Mount a sample such as a Polycarbonate initialization sample or another material on the stage 614 that covers the center of rotation of the stage 614 (e.g., the axis of rotation provided by the rotational stage 624).
   b. Use the GUI control station 110 to manually move the X, Y, and Z1 stages 620, 622 and 608 to position the center of rotation of the stage 614 approximately under the optical instrument 610 with the optical instrument focused on the sample.

c. Implement the Center of Rotation Location Calibration with the control station 110.

i. The automated testing system 600 moves the X, Y, and Z1 stages 620, 622, 608 the Tip to Optics offset determined above to move the mechanical testing instrument 612 over the location focused on with the optical instrument 610.

ii. The automated testing system 600 marks the sample with a marking 2710 (e.g., an H pattern of indents) at the location.

iii. The rotational stage 624 rotates the sample stage 614 120 degrees and the mechanical testing instrument 612 provides another marking 2710 (e.g., another H pattern). The X and Y-stages 620, 622 are static.

iv. The rotational stage 624 rotates the sample stage 614 120 more degrees (240 degrees total) and provides a third marking 2710.

v. The X, Y, Theta, and Z1 instrument stages 620, 622, 624, 608 are returned to their original positions to position the first marking 2710 under the optical instrument 610 and in focus. The first marking 2710 is centered under the reticle of the optical instrument 610.

vi. The GUI control station 110 prompts the user to locate the other two markings 2710 (e.g., H-patterns of indents) by manually operating the X and Y-stages 620, 622. The rotational stage 624 is static. Optionally, the control station 110 includes pattern recognition software to detect and index the markings 2710 or the each of the markings 2170 are indexed as they are marked on the sample.

vii. The user (or software control algorithm) moves the stages 620, 622 until the location focus 2714 of each marking 2710 is aligned with the camera reticle of the optical instrument 610. The automated testing system 600 will record (e.g., index) the X and Y stage coordinates of the center of each H-pattern: $X_0, Y_0; X_{120}, Y_{120}; X_{240}, Y_{240}$. Optionally, the control station 110 includes pattern recognition software to detect and index the markings 2710 or the each of the markings 2170 are indexed as they are marked on the sample.

viii. The automated testing system 600 fits a circle (e.g., a stage center circle 2820) to the three sets of X and Y coordinates corresponding to the markings 2710. The center of the fit circle is the X-Y stage coordinates for the center of rotation 2606 of the sample stage 614. The center of rotation coordinates are $(X_{center}, Y_{center})$. The analysis below provides one example of mathematical equations for determining the center of rotation 2606 from the coordinates of the markings 2710. "r" is the radius of the stage center circle 2820.

$$(X_0 - X_C)^2 + (Y_0 - Y_C)^2 = r^2$$

$$(X_{120} - X_C)^2 + (Y_{120} - Y_C)^2 = r^2$$

$$(X_{240} - X_C)^2 + (Y_{240} - Y_C)^2 = r^2$$

$$X_0^2 - 2X_0 X_C + X_C^2 + Y_0^2 - 2Y_0 Y_C + Y_C^2 =$$
$$X_{120}^2 - 2X_{120}X_C + X_C^2 + Y_{120}^2 - 2Y_{120}Y_C + Y_C^2$$

$$X_{240}^2 - 2X_{240}X_C + X_C^2 + Y_{240}^2 - 2Y_{240}Y_C + Y_C^2 =$$
$$X_{120}^2 - 2X_{120}X_C + Y_{120}^2 - 2Y_{120}Y_C + Y_C^2$$

$$X_0^2 - 2X_0 X_C + Y_0^2 - 2Y_0 Y_C = X_{120}^2 - 2X_{120}X_C + Y_{120}^2 - 2Y_{120}Y_C$$

$$X_{240}^2 - 2X_{240}X_C + Y_{240}^2 - 2Y_{240}Y_C = X_{120}^2 - 2X_{120}X_C + Y_{120}^2 - 2Y_{120}Y_C$$

$$X_C = \frac{X_{120}^2 + Y_{120}^2 - 2Y_{120}Y_C - X_0^2 - Y_0^2 + 2Y_0 Y_C}{2(X_{120} - X_0)}$$

$$X_C = \frac{X_{120}^2 + Y_{120}^2 - 2Y_{120}Y_C - X_{240}^2 - Y_{240}^2 + 2Y_{240}Y_C}{2(X_{120} - X_{240})}$$

$$X_C = \frac{X_{120}^2 + Y_{120}^2 - 2Y_{120}Y_C - X_0^2 - Y_0^2 + 2Y_0 Y_C}{2(X_{120} - X_0)} =$$
$$\frac{X_{120}^2 + Y_{120}^2 - 2Y_{120}Y_C - X_{240}^2 - Y_{240}^2 + 2Y_{240}Y_C}{2(X_{120} - X_{240})}$$

$$\frac{X_{120}^2 + Y_{120}^2 - X_0^2 - Y_0^2}{2(X_{120} - X_0)} + \frac{2Y_0 Y_C - 2Y_{120}Y_C}{2(X_{120} - X_0)} =$$
$$\frac{X_{120}^2 + Y_{120}^2 - X_{240}^2 - Y_{240}^2}{2(X_{120} - X_{240})} + \frac{2Y_{240}Y_C - 2Y_{120}Y_C}{2(X_{120} - X_{240})}$$

$$\frac{X_{120}^2 + Y_{120}^2 - X_0^2 - Y_0^2}{(X_{120} - X_0)} - \frac{X_{120}^2 + Y_{120}^2 - X_{240}^2 - Y_{240}^2}{(X_{120} - X_{240})} =$$
$$\frac{2Y_{240}Y_C - 2Y_{120}Y_C}{(X_{120} - X_{240})} - \frac{2Y_0 Y_C - 2Y_{120}Y_C}{(X_{120} - X_0)}$$

$$(X_{120}^2 + Y_{120}^2 - X_0^2 - Y_0^2)(X_{120} - X_{240}) -$$
$$(X_{120}^2 + Y_{120}^2 - X_{240}^2 - Y_{240}^2)(X_{120} - X_0) =$$
$$(2Y_{240}Y_C - 2Y_{120}Y_C)(X_{120} - X_0) - (2Y_0 Y_C - 2Y_{120}Y_C)(X_{120} - X_{240})$$

$$Y_C = \frac{(X_{120}^2 + Y_{120}^2 - X_0^2 - Y_0^2)(X_{120} - X_{240}) - (X_{120}^2 + Y_{120}^2 - X_{240}^2 - Y_{240}^2)(X_{120} - X_0)}{(2Y_{240} - 2Y_{120})(X_{120} - X_0) - (2Y_0 - 2Y_{120})(X_{120} - X_{240})}$$

Deskewing

1. The robotic handling system 200 pulls a sample 2610 from the storage module 104.

a. The sample 2610 is roughly centered on the handling fork 404.

b. The sample 2610 is roughly oriented with its sample orientation feature 2618 (e.g., a notch) in a known direction.

2. The robotic handling system 200 loads the sample 2610 onto the sample stage 614. The elevation pins 634 lower the sample 2610 on to the sample stage surface 616. Optionally, vacuum ports 632 vacuum couple the sample 2610 to the sample stage 614.

3. Implement the Procedure to Determine the First Reference Point of the Sample (Translational Deskewing)—This procedure locates the sample 2610 for the automated testing system 600 within a linear tolerance of around about 1 micron. Finding the first reference point of the sample 2610, such as the center 2622 improves the accuracy of automated test site location.

a. The Y-stage 622 moves so the Y coordinate of the center of rotation of the stage 614 is aligned with the Y location of the reticle in the optical instrument 610 (e.g., the optical working region 2716).

b. Optionally, the Z1 stage 608 moves to focus the optical instrument 610 on the sample 2610.

c. The rotational stage 624 moves to three different positions approximately 120 degrees apart including positions on the sample 2610 that avoid positioning the wafer orientation feature 2618 (e.g., a notch or flat) within the optical instrument working region 2716.

d. At each of the three different rotational positions (e.g., 0, 120 and 240 degrees), starting at a position where the optical instrument 610 is focused on the sample 2610, the X-stage 620 moves in a direction that will eventually move the sample 2610 out from the optical working region 2716.

e. At each of the three rotational positions, an edge detecting vision algorithm (e.g. provided in the control station 110) records the exact translation value of the X-stage 620 where the edge 2922 of the sample 2610 lines up with the optical instrument 610 corresponding to the sample edge locations 2924.

f. These three translational and rotational coordinates of the sample edge (X, and Theta measurements of, for instance 0, 120 and 240 degrees) are used to calculate the r, φ location of the center 2622 of the sample 2610 relative to the center of rotation 2606 of the stage 614. See FIGS. 26C and 29B. The φ value is the first reference angular offset of the sample center relative to the stage center of rotation 2606.

4. Implement the Procedure to Determine the Second Reference Point of the Sample (Rotational Deskewing)—This procedure determines the orientation of the sample orientation feature 2618 relative to the sample stage 614 (by way of the sample center 2622). The procedure determines the sample 2610 orientation to within a tolerance on the order of around about 0.001 degrees.

a. The X, Y, and rotational stages 620, 622, 624 move to focus the optical instrument working region 2716 on a position near the sample edge 2922 of the sample 2610 and in the general vicinity of the sample orientation feature 2618 (e.g., the theta angle).

b. The Y-stage 622 is operated to position the center 2622 of the sample 2610 in alignment with the optical instrument 610.

$$Y_{sample\ center} = Y_{center} + r^*\sin(\phi + theta)$$

c. The X-stage 620 is operated to position the center 2622 of the sample 2610 just inside the sample edge 2922 of the sample. In one example, the sample 2610 is a 150 mm radius semi-conductor wafer.

$$X_{sample\ edge} = X_{center} + 149 + r^*\cos(\phi + theta)$$

d. The rotational stage 624 is operated to rotate sample 2610. An edge detecting vision algorithm is used with the optical instrument 610 to detect the angular measures of both feature portions 3020, 3022 (e.g., the edges of the notch or flat) of the sample orientation feature 2618.

e. The average of the two angular measures, for instance $theta_1$ and $theta_2$, is the α value (e.g., the second reference angular offset) for the actual orientation of the wafer.

Automated Test Site Location

1. The coordinates of one or more testing locations 2620 are input (e.g., read from instructions, hand keyed and the like) according to the sample coordinate system 2612 ($x_w$, $y_w$ including for instance the X and Y coordinates for $T_{1-4}$ shown in FIG. 26B). Optionally, the coordinates are input at the control station 110. In another example, all testing locations for that type of sample (e.g., a semiconductor wafer with a diameter of 300 mm) will be stored in the measurement recipe in the control station 110.

2. One or more of the control station 110 or the automated testing system 600 calculates the stage coordinates (X, Y, Θ) from the sample coordinates based on the sample coordinate system 2612 needed to place the optical instrument 610 or the mechanical testing instrument 612 over each of the testing locations 2620 according to the following equations that incorporate the previously determined values for r, φ and α:

$$\Theta = A\ TAN\ 2(y_w, x_w) + \alpha$$

The Θ value is used to rotate the sample 2610 with the rotational stage 624 so the desired testing location 2620 is in line with the Y-location of the center of the optics. In other words, the testing location is on a line through the center of the sample and parallel to the Y translational axis of the Y-stage 622 after the Θ rotation.

$$X = X_{center} + r^*\cos(\Theta + \phi) + x_w^*\cos(\alpha + \Theta) - y_w^*\sin(\alpha + \Theta)$$

The X value is used to translate the sample 2610 with the X-stage 620 so the desired testing location 2620 is aligned with one of the optical and mechanical testing instruments 610, 612.

$$Y = Y_{center} + r^*\sin(\Theta + \phi)$$

The Y value is used to optionally translate the sample 2610 with the Y-stage 622 so the desired testing location 2620 is aligned with one of the optical and mechanical testing instruments 610, 612. Translation according to the Y value is in one example optional. For instance, where there is a misalignment between the optical and mechanical testing instruments 610, 612 along the Y axis of the Y-Stage 622, the Y value corrects for this misalignment and positions the testing location in alignment with either of the instruments.

3. Where the X, Y and Θ coordinates are used to position the desired testing location 2620 in alignment with the optical instrument, the X and Y stages 620, 622 are operated to move the desired testing location 2620 into alignment with the mechanical testing instrument 610 (e.g., the location of the probe 702) according to the Tip to Optics calibration offset (e.g., the instrument offset composite 2722 including one or more of the Y and Y instrument offsets 2718, 2720).

The combination of x-y-theta (rotational) positioning (as opposed to x, y positioning alone) described in the example above and herein, allows for the minimal cantilevering of the instruments on the cantilevered instrument column. Stated another way, through a combination of x, y positioning along with rotation, all portions of a 300 mm wafer are positionable beneath the mechanical testing instrument with an arm configured to position the instrument across the radius of the wafer (e.g., 150 mm). An X-Y only system would require at least 300 mm of cantilever or a bridge structure having a large mass, footprint, and in some cases a natural frequency that is not cooperative with the frequencies of the automated testing system 100 but is dictated by the mass of the bridge.

Further, the x-y-theta stage includes an X stage with a larger range of translation available than the Y stage. This allows the X stage to have sufficient travel to move at least one radius of the wafer (150 mm) under the optics and transducer heads (an additional 150 mm) The Y travel is long enough to accommodate the small difference in Y positions between the optics and transducer heads (several millimeters).

The x-y-theta positioning of the sample stage 614 thereby correspondingly minimizes the length of the cantilevered arm of the instrument column 606. The system with the short cantilevered arm (e.g., the cantilevered instrument column 606 in FIG. 6A) is thereby more resistant to mechanical noise (has a high stiffness without an extensive arm that is prone to deflection). Deflections of cantilevers increase with the cube of the cantilever length so reducing the cantilever length by a factor of 2 reduces the deflections by a factor of 8 for the same beam cross section and loading.

The footprint of the system 600 (See FIG. 6A) with the short arm and the compactly moving stage is minimal. In other words, a compact cantilevered arm 606 in combination with a compact x-y-theta stage system 614 fits within a smaller enclosure (e.g., the automated testing enclosure 108) and assumes less space on the factory floor. Conventional support structures, such as a bridge or arch assembly extending to either side of the sample stage with corresponding support legs and x-y stage assemblies (and corresponding enlarged footprints) are not needed.

Conclusion

The systems and methods described herein provide a rapid and accurate method for testing multiple samples with multiple testing locations directly or near directly from production. Each of the systems and methods further provide one or more of functions and benefits provided herein. For instance, the systems provide an orderly and efficient process for conducting micro- and nanomechanical testing on a series of samples with a minimum of system downtime between sample tests. Additionally, the systems and methods facilitate high throughput testing that acquires greater and more accurate statistical sampling data on the tested materials.

Further, the systems and methods described herein provide a system that minimizes surface contamination of material samples prior and subsequent to conducting micro- and nanomechanical testing in order to achieve accurate test data even where the samples are taken immediately from production or are in-line with production.

Further still, the systems and methods described herein precisely move and control the material samples into and out of a nanomechanical testing instrument in order to minimize damage or breakage of nanomechanical testing system components as well as material samples.

Moreover, the systems and methods significantly reduce the average, per-test costs associated with testing a relatively high volume of material samples and reduce yield loss. Further, the systems and methods reduce measurement error through, for instance, operator interaction. By reducing operation interaction labor costs are reduced and facilities are efficiently used, including eliminating the cost and labor for maintaining a smaller clean room environment. For instance, the indexing of samples relative to the coordinate systems and instruments of the automated testing system through the analysis of each sample as positioned on the sample stage allows for accurate and precise positioning of one of more testing locations (e.g., specified testing locations of a heterogeneous sample) relative to the instruments. Further still, the provision of the probe change assembly (or assemblies), diagnostic samples, methods for analyzing the probe, calibrating the automated testing system according to the characteristics of the probe and the like further minimize operator interaction and decrease system downtime.

The systems and methods described herein collect, manage and monitor quality control data relative to tested samples and enable long-term tracking of material sample data, to utilize material sample data to identify real-time production line problems and to correlate this data to long-term material and/or device performance.

Further, in another example, the systems and methods automatically identify test locations on the material surface prior to conducting micro- and nanomechanical testing to achieve accurate test data on the region of interest.

The non-limiting examples shown in the figures and description herein can be combined in any permutation or combination. That is to say, the features shown in any one example (figure, passage and the like) are combinable with other examples described herein alone or with other features. Further, features found in various claims whether dependent or independent claims may be combined with other examples, claims and the like by themselves or in combination with other claimed and unclaimed features described herein. Furthermore, any reference to numbered elements in the descriptions of the methods is not intended to be limited to the numbered elements described. Instead, the numbered elements are provided for exemplary purposes only. The numbered elements are intended to include all similar elements described herein as well as their equivalents.

Various Notes & Examples

Example 1 can include a testing system including a multiple degree of freedom stage for aligning a sample with an instrument configured for mechanical testing at micron or less scale, the testing system comprising a instrument column including a column base and an instrument arm extending from the column base; an instrument coupled with the instrument arm; a multiple degree of freedom sample stage assembly including: a sample stage, and a stage actuator assembly including at least one translational actuator and a rotational actuator, and the stage actuator assembly is configured to selectively align substantially all locations between the instrument and the sample stage with the instrument through actuation of the at least one of the translational actuator and the rotational actuator.

Example 2 can include, or can optionally be combined with the subject matter of Example 1, to optionally include wherein the instrument arm is cantilevered and extends from the column base less than a sample stage length of the sample stage.

Example 3 can include, or can optionally be combined with the subject matter of one or any combination of Examples 1 or 2 to optionally include wherein the sample stage includes a sample stage footprint based on the range of translation and rotation provided by the at least one translational actuator and the rotational actuator, and at least a first dimension of the sample stage footprint is substantially similar to a sample stage length.

Example 4 can include, or can optionally be combined with the subject matter of one or any combination of Examples 1 through 3 to optionally include wherein a testing system footprint of the testing system includes: the sample stage footprint, and a column footprint of the instrument column bounded by the column base.

Example 5 can include, or can optionally be combined with the subject matter of one or any combination of Examples 1 through 4 to optionally include wherein the at least one translational actuator includes an X-stage actuator and a Y-stage actuator, the X and Y-stage actuators are respectively configured to translate the sample stage along X and Y axes, and a Y-axis translation range of the sample stage is coextensive with the first dimension of the sample stage footprint.

Example 6 can include, or can optionally be combined with the subject matter of one or any combination of Examples 1 through 5 to optionally include wherein an X-axis translation range of the sample stage is coextensive with a second dimension of the sample stage footprint, and the X-axis translation range is greater than the Y-axis translation range.

Example 7 can include, or can optionally be combined with the subject matter of one or any combination of Examples 1 through 6 to optionally include wherein the instrument includes an instrument footprint smaller than a sample stage footprint, and the stage actuator assembly is configured to selectively align substantially all locations of the sample stage with the instrument footprint.

Example 8 can include, or can optionally be combined with the subject matter of one or any combination of Examples 1 through 7 to optionally include an instrument actuator configured for moving the instrument orthogonally relative to the sample stage.

Example 9 can include, or can optionally be combined with the subject matter of one or any combination of Examples 1 through 8 to optionally include wherein the at least one translational actuator includes an X-stage actuator and a Y-stage actuator, the X and Y-stage actuators are respectively configured to translate the sample stage along X and Y axes.

Example 10 can include, or can optionally be combined with the subject matter of one or any combination of Examples 1 through 9 to optionally include a method for selectively aligning and testing one or more testing locations with an instrument, the method comprising coupling a sample on a sample stage of a testing system, the sample includes one or more testing locations spaced apart on the sample, wherein the testing system includes: an instrument configured for one or more of testing or observation of the sample, and the sample stage; aligning a testing location of the one or more testing locations with the instrument, aligning the testing location includes: rotating the sample stage and the testing location toward alignment with a working region of the instrument, and translating the sample stage and the testing location toward alignment with the working region of the testing instrument; and testing the testing location of the one or more testing locations with the instrument.

Example 11 can include, or can optionally be combined with the subject matter of one or any combination of Examples 1 through 10 to optionally include wherein testing includes one or more of mechanical testing or observation at micron or less scale with the instrument.

Example 12 can include, or can optionally be combined with the subject matter of one or any combination of Examples 1 through 11 to optionally include wherein translating the sample stage includes: translating the sample stage along an X axis, and constraining translation of the sample stage along a Y axis substantially parallel to a cantilevered instrument arm coupled with the instrument.

Example 13 can include, or can optionally be combined with the subject matter of one or any combination of Examples 1 through 12 to optionally include wherein constraining translation of the sample stage along the Y axis includes translating the sample stage along the Y axis between the instrument and another instrument.

Example 14 can include, or can optionally be combined with the subject matter of one or any combination of Examples 1 through 13 to optionally include wherein aligning the testing location of the one or more testing locations with the instrument includes rotating the sample stage and rotating the testing location into coincidence with the X axis where the testing location has an original non-zero Y location relative to the Y axis.

Example 15 can include, or can optionally be combined with the subject matter of one or any combination of Examples 1 through 14 to optionally include aligning the testing location with the instrument includes translating and rotating the sample stage and the sample within a sample stage footprint bounded by outermost perimeter surfaces of the sample stage relative to the instrument in a plurality of orientations configured to selectively align the instrument with substantially the entire surface area of the sample stage.

Example 16 can include, or can optionally be combined with the subject matter of one or any combination of Examples 1 through 15 to optionally include wherein aligning the testing location with the instrument includes translating and rotating the sample stage and the sample within the sample stage footprint, and the sample stage footprint is within a testing system footprint including the sample stage footprint and a column footprint bounded by a column base of a cantilevered instrument column coupled with the instrument.

Example 17 can include, or can optionally be combined with the subject matter of one or any combination of Examples 1 through 16 to optionally include wherein aligning the testing location of the one or more testing locations with the instrument includes: determining first X and Y coordinates for the testing location relative to an origin of a sample coordinate system of the sample, transforming the first X and Y coordinates into an angle value and a translational value for a rotational stage and at least one translational stage coupled with the sample stage, respectively, rotating the sample stage and the testing location includes rotating the testing location the angle value into coincidence with a translational axis of the translational stage, and translating the sample stage and the testing location includes translating the testing location the translational value parallel to the translational axis.

Example 18 can include, or can optionally be combined with the subject matter of one or any combination of Examples 1 through 17 to optionally include wherein aligning the testing location of the one or more testing locations includes aligning at least one of an X and Y axis of the sample coordinate system with the instrument.

Example 19 can include, or can optionally be combined with the subject matter of one or any combination of Examples 1 through 18 to optionally include rotating the sample stage and the each of the one or more testing locations respective angle values into respective coincidence with the translational axis of the translational stage, and rotating the sample stage eliminates translation along a second translational axis different from the translational axis because of differing Y coordinates of a plurality of testing locations where the one or more testing locations includes the plurality of testing locations.

Example 20 can include, or can optionally be combined with the subject matter of one or any combination of Examples 1 through 19 to optionally include indexing and deskewing the sample with the one or more testing locations, indexing and deskewing including: indexing the position and orientation of the sample relative to the sample stage, the sample includes first and second reference points and the sample stage includes a sample stage reference point, indexing including: determining a first reference position of the first reference point relative to the sample stage reference point, and determining a second reference angular offset of the second reference point relative to the first reference point.

Example 21 can include, or can optionally be combined with the subject matter of one or any combination of Examples 1 through 20 to optionally include wherein determining the first reference position of the first reference point includes: determining a radius of the first reference point from the sample stage reference point, and determining a first reference angular offset of the first reference point relative to the sample stage reference point.

Example 22 can include, or can optionally be combined with the subject matter of one or any combination of Examples 1 through 21 to optionally include determining the first reference point of the sample, wherein the first reference point is a center of the sample, and the sample is circular, determining the first reference point including: sensing a circular edge location of a plurality of circular edge locations of a sample edge, sensing including: translating the sample stage and the sample edge toward the optical instrument, detecting the circular edge location with the optical instrument as the optical instrument crosses over the sample edge, indexing the circular edge location relative to the sample stage reference point, and rotating the sample stage and the sample a specified angle measure; repeating the sensing of the circular edge location after each rotation until three or more circular edge locations are indexed; and determining the center of the sample from a circle having a perimeter coincident with the three or more circular edge locations.

Example 23 can include, or can optionally be combined with the subject matter of one or any combination of Examples 1 through 22 to optionally include aligning an optical instrument with the sample stage reference point along at least a first translational axis;

Example 24 can include, or can optionally be combined with the subject matter of one or any combination of Examples 1 through 23 to optionally include wherein translating the sample stage and the sample edge toward the optical instrument includes translating the sample stage along a second translational axis different from the first translational axis.

Example 25 can include, or can optionally be combined with the subject matter of one or any combination of Examples 1 through 24 to optionally include wherein determining the second reference angular offset of the second reference point includes: translating the sample stage and the sample along a first translational axis relative to the optical instrument to a location near an edge of the sample and the second reference point, wherein the optical instrument is aligned with the sample, rotating the sample stage, detecting the second reference point with the optical instrument, the second reference point having a second reference angular offset relative to the first reference point according to the rotation of the sample stage and the sample.

Example 26 can include, or can optionally be combined with the subject matter of one or any combination of Examples 1 through 25 to optionally include aligning an optical instrument with a second translational axis coincident with the first reference point, the second translational axis is orthogonal to the first translational axis, Example 27 can include, or can optionally be combined with the subject matter of one or any combination of Examples 1 through 26 to optionally include wherein detecting the second reference point includes detecting first and second portions of the second reference point, wherein each of the first and second portions includes respective first and second angular measurements.

Example 28 can include, or can optionally be combined with the subject matter of one or any combination of Examples 1 through 27 to optionally include wherein detecting the second reference point includes averaging the first and second angular measurements and the average of the first and second angular measurements is the second reference angular offset.

Example 29 can include, or can optionally be combined with the subject matter of one or any combination of Examples 1 through 28 to optionally include determining an instrument offset between an optical instrument and the instrument, determining the instrument offset including: marking the sample with a mark at a first offset marking location on the sample with the instrument, wherein the instrument is aligned with the mark, translating the sample stage and the mark at the first offset marking location of the sample into alignment with the optical instrument, and measuring the translation of the sample stage from alignment of the mark with the instrument to alignment of the mark with the optical instrument, and the instrument offset is equivalent to the measured translation.

Example 30 can include, or can optionally be combined with the subject matter of one or any combination of Examples 1 through 29 to optionally include determining the center of rotation of the sample stage including: marking the sample at a plurality of locations including: marking the sample at a first location of the plurality of locations with the instrument, and rotating the sample stage and the sample a specified angle measure, wherein the sample stage and the sample are translationally static relative to a base; repeating marking of the sample at second and third locations of the plurality of locations according to the repeated rotation of the sample stage and the sample; and determining the center of rotation of the sample stage from a circle having a perimeter coincident with the plurality of locations, the center of rotation coincident to a center of the circle.

Example 31 can include, or can optionally be combined with the subject matter of one or any combination of Examples 1 through 30 to optionally include translating the sample stage and the sample between the plurality of locations; observing each of the marks at the plurality of locations with an optical instrument, wherein the marks are indents; indexing the marks at the plurality of locations; and determining the center of rotation of the sample stage includes forming the circle having the perimeter coincident with each of the indexed marks at the plurality of locations, the center of rotation coincident to the center of the circle.

Example 32 can include, or can optionally be combined with the subject matter of one or any combination of Examples 1 through 31 to optionally include a method for automatically examining an instrument probe coupled with a mechanical testing instrument configured to performing mechanical testing at micron scale or less, the method comprising determining if an instrument probe use threshold is achieved, the instrument probe is coupled with a transducer, and the transducer is configured to move the instrument probe, measure an instrument probe indentation depth and measure force applied to the instrument probe through the transducer; and conducting a probe check operation once the instrument probe use threshold is achieved, the probe check operation includes: aligning the instrument probe with a diagnostic sample, indenting the instrument probe into the diagnostic sample, measuring one or more of the indentation depth, indentation force or a sample mechanical parameter with the transducer, and determining the instrument probe requires one of calibration or replacement if one or more of the measured indentation depth, the measured indentation force or the sample mechanical parameter are outside of an indentation threshold range, an indentation force threshold range or a sample mechanical parameter threshold range of the diagnostic sample, respectively.

Example 33 can include, or can optionally be combined with the subject matter of one or any combination of Examples 1 through 32 to optionally include wherein determining if the instrument probe use threshold is achieved includes: counting the number of transducer operations, and determining if the number of transducer operations are greater than a transducer operation count threshold.

Example 34 can include, or can optionally be combined with the subject matter of one or any combination of Examples 1 through 33 to optionally include wherein determining if the transducer operation count threshold is achieved includes adjusting the transducer operation count threshold according to one or more of the material tested with the instrument probe and the force applied to the probe through the transducer.

Example 35 can include, or can optionally be combined with the subject matter of one or any combination of Examples 1 through 34 to optionally include wherein determining if the transducer operation count threshold is achieved includes adjusting the transducer operation count threshold according to a specified accuracy range.

Example 36 can include, or can optionally be combined with the subject matter of one or any combination of Examples 1 through 35 to optionally include wherein determining if the instrument probe use threshold is achieved includes: measuring one or more of the instrument probe indentation depth, force applied to the instrument probe through the transducer or a sample mechanical parameter of a sample, and determining the instrument probe use threshold is met if one or more of the instrument probe indentation depth, force applied to the instrument or the sample mechanical parameter is outside of one or more of a specified indentation depth threshold range, a specified force threshold range or a specified sample mechanical parameter threshold range of the sample.

Example 37 can include, or can optionally be combined with the subject matter of one or any combination of Examples 1 through 36 to optionally include wherein aligning the instrument probe with the diagnostic sample includes moving the diagnostic sample beneath the instrument probe.

Example 38 can include, or can optionally be combined with the subject matter of one or any combination of Examples 1 through 37 to optionally include wherein moving the diagnostic sample beneath the instrument probe includes one or more of translating and rotating a sample stage surface, wherein the sample stage surface includes a stage receptacle flange housing one or more diagnostic samples.

Example 39 can include, or can optionally be combined with the subject matter of one or any combination of Examples 1 through 38 to optionally include wherein moving the diagnostic sample includes translating the sample stage surface along an X-axis and a Y-Axis.

Example 40 can include, or can optionally be combined with the subject matter of one or any combination of Examples 1 through 39 to optionally include wherein moving the diagnostic sample includes rotating the sample stage surface around a Z-axis.

Example 41 can include, or can optionally be combined with the subject matter of one or any combination of Examples 1 through 40 to optionally include wherein moving the diagnostic sample beneath the instrument probe includes a combination of translating and rotating a sample stage surface from a first sample location where the instrument probe is aligned with the first sample location to a second diagnostic location where the instrument probe is aligned with the diagnostic sample.

Example 42 can include, or can optionally be combined with the subject matter of one or any combination of Examples 1 through 41 to optionally include conducting a probe calibration if one or more of the measured indentation depth, the measured indentation force or the sample mechanical parameter are outside of the indentation threshold range, the indentation force threshold range or the sample mechanical parameter threshold range, respectively, the probe calibration including: performing one or more indentations with the instrument probe against the diagnostic sample, each of the one or more indentations are conducted according to a specified array of one of indentation depths or indentation forces, each of the indentation depths and indentations forces are different; measuring one of the indentation force or the indentation depth of each of the one or more indentations according to the specified array of indentation depths or indentation forces; associating the respective measured indentation forces or the measured indentation depths with the corresponding indentation depths or indentation forces of the specified array; calculating a probe area function for the instrument probe according to the relationship between the associated indentation forces or indentation depths with the indentation depths or indentation forces of the specified array; and calibrating functions for generating one or more of modulus and hardness values for a sample according to the probe area function.

Example 43 can include, or can optionally be combined with the subject matter of one or any combination of Examples 1 through 42 to optionally include conducting the probe check operation after calculation of the probe area function, and determining the instrument probe requires replacement if one or more of the measured indentation depth, the measured indentation force or the sample mechanical parameter are outside of the indentation threshold range, the indentation force threshold range or the sample mechanical parameter threshold range of the diagnostic sample, respectively.

Example 44 can include, or can optionally be combined with the subject matter of one or any combination of Examples 1 through 43 to optionally include a method for automatically examining a transducer response of a mechanical testing instrument configured to perform mechanical testing at micron scale or less, the method comprising: determining if a transducer operation threshold is achieved, the transducer is coupled with an instrument probe, and the transducer is configured to move the instrument probe, measure the instrument probe movement and measure the force applied to the instrument probe through the transducer; and conducting a space indentation operation with the transducer once the transducer operation threshold is achieved, the space indentation operation includes: moving the instrument probe into a position where the instrument probe will not engage a surface during the space indentation, applying a specified voltage to the transducer, measuring the movement of the instrument probe caused by the application of the specified voltage, and determining the transducer requires one or more of calibration or service if the movement is outside of a specified movement threshold for the specified voltage.

Example 45 can include, or can optionally be combined with the subject matter of one or any combination of Examples 1 through 44 to optionally include wherein determining if the transducer operation threshold is achieved includes: counting the number of transducer operations, and determining if the number of transducer operations are greater than a transducer operation count threshold.

Example 46 can include, or can optionally be combined with the subject matter of one or any combination of Examples 1 through 45 to optionally include wherein determining if the transducer operation threshold is achieved includes adjusting the transducer operation count threshold according to one or more of the material tested with the instrument probe and the force applied to the probe through the transducer.

Example 47 can include, or can optionally be combined with the subject matter of one or any combination of Examples 1 through 46 to optionally include wherein determining if the transducer operation threshold is achieved includes adjusting the transducer operation count threshold according to a specified accuracy range.

Example 48 can include, or can optionally be combined with the subject matter of one or any combination of Examples 1 through 47 to optionally include wherein determining if the transducer operation threshold is achieved includes determining that the transducer operation threshold is achieved if the transducer measures a force outside of a normal operating force range.

Example 49 can include, or can optionally be combined with the subject matter of one or any combination of Examples 1 through 48 to optionally include a testing system including a probe changing assembly for coupling and decoupling a probe of a mechanical testing instrument configured for mechanical testing at micron or less scale, the probe changing assembly comprising: a probe magazine housing a plurality of probes, the probes are configured for mechanical testing at micron scale or less; at least one probe change unit configured to: grasp one of the plurality of probes housed in the probe magazine, couple one of the plurality of probes with a probe receptacle of a mechanical testing instrument, and decouple one of the plurality of probes from the probe receptacle of the mechanical testing instrument; and an actuator coupled with the at least one probe change unit, and the actuator is configured to move and align the at least one probe change unit with the probe magazine and the probe receptacle of the mechanical testing instrument.

Example 50 can include, or can optionally be combined with the subject matter of one or any combination of Examples 1 through 49 to optionally include a mechanical testing instrument including: a transducer, and a probe receptacle coupled with the transducer, the probe receptacle is configured to couple with at least one of the plurality of probes.

Example 51 can include, or can optionally be combined with the subject matter of one or any combination of Examples 1 through 50 to optionally include wherein the actuator includes a multiple degree of freedom stage, the multiple degree of freedom stage includes: an X-stage configured to linearly move the at least one probe change unit along an X-axis, and a Y-stage configured to linearly move the at least one probe change unit along a Y-axis.

Example 52 can include, or can optionally be combined with the subject matter of one or any combination of Examples 1 through 51 to optionally include wherein the actuator includes a theta stage coupled with at least one of the X and Y-stages, the theta stage is configured to rotate the at least one probe change unit about a Z-axis.

Example 53 can include, or can optionally be combined with the subject matter of one or any combination of Examples 1 through 52 to optionally include wherein the actuator includes a multiple degree of freedom stage, the multiple degree of freedom stage includes: a sample stage surface, a stage receptacle flange coupled with the sample stage surface, and one or more stage receptacles, each of the one or more stage receptacles are sized and shaped to house one of the at least one probe change units.

Example 54 can include, or can optionally be combined with the subject matter of one or any combination of Examples 1 through 53 to optionally include at least one diagnostic sample, the diagnostic sample is coupled with the actuator, and the actuator is configured to move and align the at least one diagnostic unit with the probe receptacle of the mechanical testing instrument.

Example 55 can include, or can optionally be combined with the subject matter of one or any combination of Examples 1 through 54 to optionally include wherein the at least one probe change unit includes: a mirror arm, and a mirror coupled with the mirror arm, the mirror is directed toward one or more of identification and calibration information on one of the plurality of probes, where the probe is grasped by the at least one probe change unit.

Example 56 can include, or can optionally be combined with the subject matter of one or any combination of Examples 1 through 55 to optionally include an optical instrument coupled with the base, and the actuator is configured to move and align the mirror with the optical instrument.

Example 57 can include, or can optionally be combined with the subject matter of one or any combination of Examples 1 through 56 to optionally include wherein the base includes a cantilevered instrument column extending over the actuator.

Example 58 can include, or can optionally be combined with the subject matter of one or any combination of Examples 1 through 57 to optionally include wherein the at least one probe change unit is configured to couple a decoupled one of the plurality of probes with the probe magazine (i.e., replace it in the probe magazine).

Example 59 can include, or can optionally be combined with the subject matter of one or any combination of Examples 1 through 58 to optionally include a probe change unit for changing instruments probes used in mechanical testing at micron scale or less, the probe change unit comprising: a motor; a drive shaft coupled with the motor; a spindle coupled with the drive shaft; a rotary clutch assembly coupled with the spindle; a probe changing tool coupled with the spindle, wherein the rotary clutch is configured to provide locking rotary engagement between the probe changing tool and the spindle in a probe decoupling rotational direction and selective slipping engagement between the probe changing tool and the spindle in a probe installing rotational direction; and wherein the probe changing tool is sized and shaped to non-rotatably couple with an instrument probe configured for mechanical testing at micron scale or less.

Example 60 can include, or can optionally be combined with the subject matter of one or any combination of Examples 1 through 59 to optionally include a drive cap interposed between the probe changing tool and the spindle, the drive cap is engaged with the probe changing tool and rotatably coupled with the spindle.

Example 61 can include, or can optionally be combined with the subject matter of one or any combination of Examples 1 through 60 to optionally include wherein the rotary clutch includes: at least one pawl, the at least one pawl includes a pawl head and a pawl tail, and the head is hingedly coupled with the spindle, and a biasing element configured to bias the tail away from the spindle.

Example 62 can include, or can optionally be combined with the subject matter of one or any combination of Examples 1 through 61 to optionally include wherein the drive cap includes: at least one pawl receiver sized and shaped to receive the pawl tail where the spindle is rotated in the probe decoupling rotational direction, and a slipping engagement surface extending along the drive cap, and in the probe installing rotational direction the slip engagement surface and the at least one pawl cooperate to statically fix the drive cap and the probe changing tool with the spindle at or below a torque threshold and to rotatably couple the drive cap and the probe changing tool relative to the spindle above the torque threshold.

Example 63 can include, or can optionally be combined with the subject matter of one or any combination of Examples 1 through 62 to optionally include wherein the biasing element is an elastomeric band received within a biasing element housing of the spindle.

Example 64 can include, or can optionally be combined with the subject matter of one or any combination of Examples 1 through 63 to optionally include wherein the at least one pawl includes a first pawl and a second pawl, and a pawl boss extends between the first and second pawls, the pawl boss is engaged with the biasing element.

Example 65 can include, or can optionally be combined with the subject matter of one or any combination of Examples 1 through 64 to optionally include a slipping interface between the drive cap and a rotational bearing coupled with the spindle.

Example 66 can include, or can optionally be combined with the subject matter of one or any combination of Examples 1 through 65 to optionally include wherein the slipping interface includes a wave washer.

Example 67 can include, or can optionally be combined with the subject matter of one or any combination of Examples 1 through 66 to optionally include a mirror arm, and a mirror directed toward one or more of identification and calibration information on an instrument probe where the instrument probe is coupled with the probe changing tool.

Example 68 can include, or can optionally be combined with the subject matter of one or any combination of Examples 1 through 67 to optionally include wherein the probe changing tool includes an access port, and one or more of the identification and calibration information are visible through the access port where the instrument probe is coupled with the probe changing tool.

Example 69 can include, or can optionally be combined with the subject matter of one or any combination of Examples 1 through 68 to optionally include an optical instrument coupled with the base, and the actuator is configured to move and align the mirror with the optical instrument.

Example 70 can include, or can optionally be combined with the subject matter of one or any combination of Examples 1 through 69 to optionally include a method for installing an instrument probe with a mechanical testing instrument configured for performing mechanical testing at micron scale or less, the method comprising: aligning an instrument probe coupled with a probe change unit with a probe receptacle of the mechanical testing instrument; moving one or more of the instrument probe or the probe receptacle into engagement with the other of the probe receptacle or the instrument probe; coupling the instrument probe with the probe receptacle; and disengaging the instrument probe from the probe change unit.

Example 71 can include, or can optionally be combined with the subject matter of one or any combination of Examples 1 through 70 to optionally include wherein aligning the instrument probe with the probe receptacle includes one or more of X-axis and Y-axis translating of the probe change unit.

Example 72 can include, or can optionally be combined with the subject matter of one or any combination of Examples 1 through 71 to optionally include wherein aligning the instrument probe with the probe receptacle includes rotating the probe change unit around a Z-axis.

Example 73 can include, or can optionally be combined with the subject matter of one or any combination of Examples 1 through 72 to optionally include wherein aligning the instrument probe with the probe receptacle includes actuating a multiple degree of freedom stage configured to translate in the X and Y-axes and rotate around a Z-axis, the multiple degree of freedom stage includes: a sample stage surface, a stage receptacle flange coupled with the sample stage surface, and one or more stage receptacles in the stage receptacle flange, each of the one or more stage receptacles are sized and shaped to house the probe change unit.

Example 74 can include, or can optionally be combined with the subject matter of one or any combination of Examples 1 through 73 to optionally include wherein moving one or more of the instrument probe or the probe receptacle into engagement with the other of the probe receptacle or the instrument probe includes translating the probe receptacle along a Z-axis with an instrument stage coupled with the mechanical testing instrument.

Example 75 can include, or can optionally be combined with the subject matter of one or any combination of Examples 1 through 74 to optionally include wherein coupling the instrument probe with the probe receptacle includes rotating the instrument probe with the probe change unit.

Example 76 can include, or can optionally be combined with the subject matter of one or any combination of Examples 1 through 75 to optionally include wherein rotating the instrument probe with the probe change unit includes rotating a probe changing tool in a probe installing rotational direction, the probe changing tool is coupled with a spindle with a rotary clutch providing a selectively slipping engagement between the probe changing tool and the spindle.

Example 77 can include, or can optionally be combined with the subject matter of one or any combination of Examples 1 through 76 to optionally include wherein coupling the instrument probe with the probe receptacle includes: initially rotating the instrument probe with the probe change unit in a probe decoupling rotational direction; measuring the force incident on a transducer of the mechanical testing instrument; arresting rotation of the probe in the probe decoupling rotational direction where the measured force incident on the transducer decreases below a thread interface force threshold; and rotating the instrument probe with the probe change unit in a probe installing rotational direction after arresting rotation of the probe in the probe decoupling rotational direction.

Example 78 can include, or can optionally be combined with the subject matter of one or any combination of Examples 1 through 77 to optionally include wherein coupling the instrument probe with the probe receptacle includes counting steps of a step motor of the probe change unit, and arresting operation of the step motor when a step count threshold is achieved.

Example 79 can include, or can optionally be combined with the subject matter of one or any combination of Examples 1 through 78 to optionally include checking coupling of the instrument probe with the probe receptacle including: measuring the force on a transducer of the mechanical testing instrument after coupling of the instrument probe; and determining the instrument probe is coupled with the probe receptacle if the transducer measures a force corresponding with an instrument probe weight.

Example 80 can include, or can optionally be combined with the subject matter of one or any combination of Examples 1 through 79 to optionally include mounting the instrument probe in the probe change unit.

Example 81 can include, or can optionally be combined with the subject matter of one or any combination of Examples 1 through 80 to optionally include wherein mounting the instrument probe in the probe change unit includes: aligning the probe change unit with the instrument probe in a probe magazine; moving one or more of the instrument probe or the probe change unit into engagement with the other of the probe change unit or the instrument probe; and coupling the instrument probe with the probe change unit.

Example 82 can include, or can optionally be combined with the subject matter of one or any combination of Examples 1 through 81 to optionally include decoupling a previously installed probe from the probe receptacle before coupling of the instrument probe with the probe receptacle.

Example 83 can include, or can optionally be combined with the subject matter of one or any combination of Examples 1 through 82 to optionally include wherein decoupling the previously installed probe from the probe receptacle includes: aligning the probe change unit with the previously installed probe; coupling the previously installed probe with the probe change unit; and decoupling the previously installed probe from the probe receptacle of the mechanical testing instrument.

Example 84 can include, or can optionally be combined with the subject matter of one or any combination of Examples 1 through 83 to optionally include loading the previously installed probe within a probe magazine.

Example 85 can include, or can optionally be combined with the subject matter of one or any combination of Examples 1 through 84 to optionally include wherein decoupling the previously installed probe from the probe receptacle includes rotating the previously installed probe with the probe change unit.

Example 86 can include, or can optionally be combined with the subject matter of one or any combination of Examples 1 through 85 to optionally include wherein rotation of the previously installed probe with the probe change unit includes rotating a probe changing tool in a probe decoupling rotational direction, the probe changing tool is coupled with a spindle with a rotary clutch providing a locking rotary engagement between the probe changing tool and the spindle.

Example 87 can include, or can optionally be combined with the subject matter of one or any combination of Examples 1 through 86 to optionally include reading one or more of identification data or calibration data from the instrument probe.

Example 88 can include, or can optionally be combined with the subject matter of one or any combination of Examples 1 through 87 to optionally include wherein reading one or more of the identification data or the calibration data includes: aligning a mirror with an optical instrument, wherein the mirror is directed toward one or more of identification or calibration data on the instrument probe; reading one or more of the identification or calibration data by way of the reflection of the mirror toward the optical instrument.

Example 89 can include, or can optionally be combined with the subject matter of one or any combination of Examples 1 through 88 to optionally include calibrating the one or more of the mechanical testing instrument or the control or measurement functions for the mechanical testing instrument according to the read calibration data.

Example 90 can include, or can optionally be combined with the subject matter of one or any combination of Examples 1 through 89 to optionally include a method for initializing a testing system comprising: positioning a sample coupled with a sample stage in alignment with an instrument, wherein the sample stage is configured for translational and rotational movement relative to a base; deformably marking the sample with marks at at least first, second and third marking locations with the instrument; rotating the sample a specified angle measure between each marking of the sample at the first, second and third marking locations, wherein the sample stage and the sample are translationally static relative to the base; and determining the center of rotation of the sample stage from a circle having a perimeter coincident with at least the markings at the first, second and third marking locations, the center of rotation coincident to a center of the circle.

Example 91 can include, or can optionally be combined with the subject matter of one or any combination of Examples 1 through 90 to optionally include translating the sample stage and the sample between at least the first, second and third marking locations, wherein the sample stage and the sample are rotationally static; observing each of the marks at the first, second and third marking locations with an optical instrument; indexing the marks at the first, second and third marking locations; and wherein determining the center of rotation of the sample stage includes determining the center of rotation from the circle having a perimeter coincident with the indexed marks.

Example 92 can include, or can optionally be combined with the subject matter of one or any combination of Examples 1 through 91 to optionally include setting the center coordinates of the sample stage at the center of rotation.

Example 93 can include, or can optionally be combined with the subject matter of one or any combination of Examples 1 through 92 to optionally include wherein positioning the sample coupled with the sample stage in alignment with the instrument includes: positioning the sample and the sample stage in alignment with an optical instrument at the first marking location, and translating the sample and the sample stage according to an instrument offset to align the first marking location with the mechanical testing instrument, wherein the sample and the sample stage are rotationally static relative to the base.

Example 94 can include, or can optionally be combined with the subject matter of one or any combination of Examples 1 through 93 to optionally include determining an instrument offset between an optical instrument and the instrument, determining the instrument offset including: deformably marking the sample with an offset marking at a first offset marking location on the sample with the instrument, wherein the instrument is aligned with the offset marking at the first offset marking location, translating the sample stage and the marking at the first offset marking location of the sample into alignment with the optical instrument, and measuring the translation of the sample stage from alignment of the marking with the instrument to alignment of the marking with the optical instrument, and the instrument offset is equivalent to the measured translation.

Example 95 can include, or can optionally be combined with the subject matter of one or any combination of Examples 1 through 94 to optionally include wherein deformably marking the sample at at least the first, second and third marking locations includes marking a specified pattern into the sample at at least one of the first, second and third indenting locations, the specified pattern including: an identification notifier, and a location focus including the marking therein, wherein the identification notifier is larger than the location focus.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the disclosure should be determined with reference to the appended claims, along with the full scope of equivalents to which such claims are entitled.

What is claimed is:

1. A testing system including a probe changing assembly for coupling and decoupling a probe of a mechanical testing instrument configured for mechanical testing at micron or less scale, the probe changing assembly comprising:
    a probe magazine housing a plurality of probes, the probes are configured for mechanical testing at micron scale or less;
    at least one probe change unit configured to:
        grasp one of the plurality of probes housed in the probe magazine,
        couple one of the plurality of probes with a probe receptacle of a mechanical testing instrument, and
        decouple one of the plurality of probes from the probe receptacle of the mechanical testing instrument; and
    an actuator coupled with the at least one probe change unit, and the actuator is configured to move and align the at least one probe change unit with the probe magazine and the probe receptacle of the mechanical testing instrument.

2. The testing system including the probe changing assembly of claim 1, wherein the actuator includes a multiple degree of freedom stage, the multiple degree of freedom stage includes:
    an X-stage configured to linearly move the at least one probe change unit along an X-axis,
    a Y-stage configured to linearly move the at least one probe change unit along a Y-axis, and
    optionally a theta stage coupled with at least one of the X and Y-stages, the theta stags configured to rotate the at least one probe change unit about a Z-axis.

3. The testing system including the probe changing assembly of claim 1, wherein the actuator includes a multiple degree of freedom stage, the multiple degree of freedom stage includes:
    a sample stage surface,
    a stage receptacle flange coupled with the sample stage surface, and
    one or more stage receptacles, each of the one or more stage receptacles are sized and shaped to house one of the at least one probe change units.

4. The testing system including the probe changing assembly of claim 1, wherein the at least one probe change unit includes:
    a mirror arm, and
    a mirror coupled with the mirror arm, the mirror is directed toward one or more of identification and calibration information on one of the plurality of probes, where the probe is grasped by the at least one probe change unit; and
    comprising an optical instrument coupled with a base, and the actuator is configured to move and align the mirror with the optical instrument.

5. A probe change unit for changing instruments probes used in mechanical testing at micron scale or less, the probe change unit comprising:
    a motor;
    a drive shaft coupled with the motor;
    a spindle coupled with the drive shaft;
    a rotary clutch assembly coupled with the spindle;
    a probe changing tool coupled with the spindle, wherein the rotary clutch is configured to provide locking rotary engagement between the probe changing tool and the spindle in a probe decoupling rotational direction and selective slipping engagement between the probe changing tool and the spindle in a probe installing rotational direction, and selective slipping engagement includes:

engagement of the spindle with the probe changing tool and transmission of rotation from the spindle to the probe changing tool for probe installation, and sliding of the spindle along the probe changing tool after probe installation; and wherein the probe changing tool is sized and shaped to non-rotatably couple with an instrument probe configured for mechanical testing at micron scale or less.

6. The probe change unit of claim 5, comprising a drive cap interposed between the probe changing tool and the spindle, the drive cap engaged with the probe changing tool and rotatable coupled with the spindle, and wherein the rotary clutch includes:
at least one pawl, the at least one pawl includes a pawl head and a pawl tail, and the head is hingedly coupled with the spindle, and
a biasing element configured to bias the tail away from the spindle.

7. The probe change unit of claim 6, wherein the drive cap includes:
at least one pawl receiver sized and shaped to receive the pawl tail where the spindle is rotated in the probe decoupling rotational direction, and
a slipping engagement surface extending along the drive cap, and in the probe installing rotational direction the slipping engagement surface and the at least one pawl cooperate to statically fix the drive cap and the probe changing tool with the spindle at or below a torque threshold and to rotatably couple the drive cap and the probe changing tool relative to the spindle above the torque threshold.

8. The probe change unit of claim 5 comprising a slipping interface between a drive cap and a rotational bearing coupled with the spindle, the drive cap interposed between the probe changing tool and the spindle, and the drive cap is engaged with the probe changing tool and rotatably coupled with spindle.

9. The probe change unit of claim 5 comprising:
a mirror arm, and
a mirror directed toward one or more of identification and calibration information on an instrument probe where the instrument probe is coupled with the probe changing tool, and
optionally an optical instrument coupled with a base, and the actuator is configured to move and align the mirror with the optical instrument.

10. A method for installing an instrument probe with a mechanical testing instrument configured for performing mechanical testing at micron scale or less, the method comprising:
aligning an instrument probe coupled with a probe change unit with a probe receptacle of the mechanical testing instrument;
moving one or more of the instrument probe or the probe receptacle into engagement with the other of the probe receptacle or the instrument probe;
coupling the instrument probe with the probe receptacle, coupling including rotating the instrument probe in probe installing rotational direction with a probe changing tool of the probe change unit, and the probe changing tool is coupled with a spindle with a rotary clutch providing slipping engagement between the probe changing tool and the spindle, slipping engagement including:
engagement of the spindle with the probe changing tool and transmission of rotation from the spindle to the probe changing tool for probe installation, and sliding of the spindle along the probe changing tool after probe installation; and disengaging the instrument probe from the probe change unit.

11. The method of claim 10, wherein aligning the instrument probe with the probe receptacle includes one or more of X-axis and Y-axis translating of the probe change unit.

12. The method of claim 11, wherein aligning the instrument probe with the probe receptacle includes rotating the probe change unit around a Z-axis.

13. The method of claim 10, wherein aligning the instrument probe with the probe receptacle includes actuating a multiple degree of freedom stage configured to translate in the X and Y-axes and rotate around a Z-axis, the multiple degree of freedom stage includes:
a sample stage surface,
a stage receptacle flange coupled with the sample stage surface, and
one or more stage receptacles in the stage receptacle flange, each of the one or more stage receptacles are sized and shaped to house the probe change unit.

14. The method of claim 10, wherein coupling the instrument probe with the probe receptacle includes:
initially rotating the instrument probe with the probe change unit in a probe decoupling rotational direction;
measuring the force incident on a transducer of the mechanical testing instrument;
arresting rotation of the probe in the probe decoupling rotational direction where the measured force incident on the transducer decreases below a thread interface force threshold; and
rotating the instrument probe with the probe change unit in a probe installing rotational direction after arresting rotation of the probe in the probe decoupling rotational direction.

15. The method of claim 10 comprising checking coupling of the instrument probe with the probe receptacle including:
measuring the force on a transducer of the mechanical testing instrument after coupling of the instrument probe; and
determining the instrument probe is coupled with the probe receptacle if the transducer measures a force corresponding with an instrument probe weight.

16. The method of claim 10 comprising mounting the instrument probe in the probe change unit including:
aligning the probe change unit with the instrument probe in a probe magazine;
moving one or more of the instrument probe or the probe change unit into engagement with the other of the probe change unit or the instrument probe; and
coupling the instrument probe with the probe change unit.

17. The method of claim 10, comprising decoupling a previously installed probe from the probe receptacle before coupling of the instrument probe with the probe receptacle, decoupling including
aligning the probe change unit with the previously installed probe;
coupling the previously installed probe with the probe change unit;
decoupling the previously installed probe from the probe receptacle of the mechanical testing instrument; and
optionally loading the previously installed probe within a probe magazine.

18. The method of claim 17, wherein decoupling the previously installed probe from the probe receptacle includes rotating the previously installed probe with the probe change unit.

19. The method of claim 10 comprising reading one or more of identification data or calibration data from the instrument probe.

20. The method of claim 19, wherein reading one or more of the identification data or the calibration data includes:
- aligning a mirror with an optical instrument, wherein the mirror is directed toward one or more of identification or calibration data on the instrument probe;
- reading one or more of the identification or calibration data by way of the reflection of the mirror toward the optical instrument; and
- comprising calibrating the one or more of the mechanical testing instrument or the control or measurement functions for the mechanical testing instrument according to the read calibration data.

* * * * *

UNITED STATES PATENT AND TRADEMARK OFFICE
CERTIFICATE OF CORRECTION

PATENT NO. : 8,770,036 B2
APPLICATION NO. : 13/962865
DATED : July 8, 2014
INVENTOR(S) : Vodnick et al.

It is certified that error appears in the above-identified patent and that said Letters Patent is hereby corrected as shown below:

In the Claims

Column 86, line 30, Claim 2, delete "stags" and insert --stage is--, therefor

Column 88, line 55, Claim 17, after "including", insert --:--, therefor

Signed and Sealed this
Eleventh Day of November, 2014

Michelle K. Lee
*Deputy Director of the United States Patent and Trademark Office*